United States Patent
Devalaraja et al.

(10) Patent No.: US 11,384,143 B2
(45) Date of Patent: Jul. 12, 2022

(54) METHODS FOR TREATING IL-6 MEDIATED INFLAMMATION WITHOUT IMMUNOSUPPRESSION

(71) Applicant: Novo Nordisk A/S, Bagsværd (DK)

(72) Inventors: Madhav N. Devalaraja, Acton, MA (US); Michael H. Davidson, Highland Park, IL (US); Rahul Kakkar, Weston, MA (US)

(73) Assignee: NOVO NORDISK A/S, Bagsvaerd (DK)

( * ) Notice: Subject to any disclaimer, the term of this patent is extended or adjusted under 35 U.S.C. 154(b) by 0 days.

(21) Appl. No.: 16/396,378

(22) Filed: Apr. 26, 2019

(65) Prior Publication Data

US 2019/0248886 A1    Aug. 15, 2019

Related U.S. Application Data

(63) Continuation of application No. 16/240,670, filed on Jan. 4, 2019, now abandoned.

(60) Provisional application No. 62/614,134, filed on Jan. 5, 2018.

(51) Int. Cl.
| | |
|---|---|
| *C07K 16/24* | (2006.01) |
| *A61K 39/00* | (2006.01) |
| *A61P 13/12* | (2006.01) |
| *A61P 37/02* | (2006.01) |
| *A61P 19/02* | (2006.01) |

(52) U.S. Cl.
CPC ............ *C07K 16/248* (2013.01); *A61P 13/12* (2018.01); *A61P 19/02* (2018.01); *A61P 37/02* (2018.01); *A61K 2039/505* (2013.01); *A61K 2039/545* (2013.01); *A61K 2039/55* (2013.01); *C07K 2317/52* (2013.01); *C07K 2317/76* (2013.01)

(58) Field of Classification Search
CPC ........ A61K 2039/505; A61K 2039/545; A61K 39/395; C07K 16/248
See application file for complete search history.

(56) References Cited

U.S. PATENT DOCUMENTS

| | | | |
|---|---|---|---|
| 5,856,135 A | 1/1999 | Tsuchiya et al. | |
| 5,888,510 A | 3/1999 | Kishimoto et al. | |
| 6,083,501 A | 7/2000 | Miyata et al. | |
| 6,121,423 A | 9/2000 | Tsuchiya et al. | |
| 6,663,864 B1 | 12/2003 | Kink et al. | |
| 7,083,784 B2 | 8/2006 | Dall'Acqua et al. | |
| 7,291,721 B2 | 11/2007 | Giles-Komar et al. | |
| 7,414,024 B2 | 8/2008 | Blay et al. | |
| 7,560,112 B2 | 7/2009 | Chen et al. | |
| 7,612,182 B2 | 11/2009 | Giles-Komar et al. | |
| 7,658,921 B2 | 2/2010 | Dall'Acqua et al. | |
| 7,833,755 B2 | 11/2010 | Chen et al. | |
| 8,153,128 B2 | 4/2012 | Bowers et al. | |
| 8,198,414 B2 | 6/2012 | Cruwys et al. | |
| 8,277,804 B2 | 10/2012 | Smith | |
| 8,945,560 B1 | 2/2015 | Clube | |
| 9,005,620 B2 | 4/2015 | Cruwys et al. | |
| 9,017,678 B1 | 4/2015 | Clube | |
| 9,187,562 B1 | 11/2015 | Clube | |
| 9,303,089 B2 | 4/2016 | Clube | |
| 9,394,568 B2 | 7/2016 | Clube | |
| 9,428,578 B2 | 8/2016 | Clube | |
| 9,439,963 B2 | 9/2016 | Clube | |
| 2001/0001663 A1 | 5/2001 | Kishimoto et al. | |
| 2004/0039826 A1 | 2/2004 | Lee | |
| 2004/0185507 A1 | 9/2004 | Giles-Komar et al. | |
| 2004/0197324 A1 | 10/2004 | Liu et al. | |
| 2006/0078533 A1 | 4/2006 | Omoigui | |
| 2006/0240012 A1 | 10/2006 | Sugimura et al. | |
| 2006/0257407 A1 | 11/2006 | Chen et al. | |
| 2006/0275294 A1 | 12/2006 | Omoigui | |
| 2007/0154481 A1 | 7/2007 | Gelinas et al. | |
| 2007/0178098 A1 | 8/2007 | Way et al. | |
| 2007/0218063 A1 | 9/2007 | Skurkovich et al. | |
| 2007/0243189 A1 | 10/2007 | Yoshizaki et al. | |
| 2008/0075726 A1 | 3/2008 | Smith et al. | |
| 2008/0090847 A1 | 4/2008 | Moe et al. | |
| 2008/0145367 A1 | 6/2008 | Bove et al. | |
| 2008/0156807 A1 | 7/2008 | Faraday | |
| 2008/0181887 A1 | 7/2008 | Dall'Acqua et al. | |
| 2008/0188401 A1 | 8/2008 | Cruwys et al. | |
| 2008/0279851 A1 | 11/2008 | Coyle et al. | |
| 2008/0312172 A1 | 12/2008 | Giles-Komar et al. | |
| 2009/0104187 A1 | 4/2009 | Kovacevich et al. | |
| 2009/0148446 A1 | 6/2009 | Skurkovich et al. | |

(Continued)

FOREIGN PATENT DOCUMENTS

| | | |
|---|---|---|
| AU | 2016302768 A1 | 2/2018 |
| AU | 2018214554 A1 | 9/2019 |

(Continued)

OTHER PUBLICATIONS

Bowie et al. Science, 1990, 247:1306-1310 (Year: 1990).*
Burgess et al. J. Cell Biol. 111:2129-2138,1990 (Year: 1990).*
Lazar et al. Mol. Cell. Biol., 8:1247-1252, 1988 (Year: 1988).*
Bork. Genome Research, 2000, 10:398-400 (Year: 2000).*
Vajdos et al. J Mol Biol. Jul. 5, 2002;320(2):415-28 (Year: 2002).*
Brown et al. J Immunol. May 1996; 156(9):3285-91 (Year: 1996).*
University of Colorado. A Study of Patients with Chronic Kidney Disease to Assess the Safety of a Single Dose of COR-001 (COR-001-SC1). Available from https://clinicaltrials.gov/ct2/show/NCT03126318). NLM identifier: NCT03126318. First posted Apr. 24, 2017 (Year: 2017).*

(Continued)

*Primary Examiner* — Vanessa L. Ford
*Assistant Examiner* — Sandra E Dillahunt
(74) *Attorney, Agent, or Firm* — Rosemarie R. Wilk-Orescan

(57) ABSTRACT

The disclosure provides methods of treating inflammation without inducing immune suppression. The method comprises administering a therapeutically effective amount of an IL-6 antagonist at a dose sufficient to reduce inflammation without causing immune suppression.

12 Claims, 6 Drawing Sheets

Specification includes a Sequence Listing.

(56) References Cited

U.S. PATENT DOCUMENTS

| | | |
|---|---|---|
| 2009/0202520 A1 | 8/2009 | Lupher, Jr. et al. |
| 2009/0239258 A1 | 9/2009 | Chen et al. |
| 2009/0263384 A1 | 10/2009 | Okada et al. |
| 2009/0269335 A1 | 10/2009 | Nakashima et al. |
| 2009/0238825 A1 | 11/2009 | Kovacevich et al. |
| 2009/0291077 A1 | 11/2009 | Smith et al. |
| 2009/0291082 A1 | 11/2009 | Smith |
| 2009/0297535 A1 | 12/2009 | Kolkman et al. |
| 2010/0015145 A1 | 1/2010 | Sheriff et al. |
| 2010/0129354 A1 | 5/2010 | Merchiers et al. |
| 2010/0129357 A1 | 5/2010 | Garcia-Martinez et al. |
| 2010/0150829 A1 | 6/2010 | Garcia-Martinez et al. |
| 2010/0158859 A1 | 6/2010 | Smith et al. |
| 2010/0203009 A1 | 8/2010 | Weaver et al. |
| 2010/0215654 A1 | 8/2010 | Bove et al. |
| 2010/0285011 A1 | 11/2010 | Morichika et al. |
| 2011/0002936 A1 | 1/2011 | Ferlin et al. |
| 2011/0171241 A1 | 7/2011 | Dix et al. |
| 2012/0034212 A1* | 2/2012 | Bowen ............... A61P 19/08 424/133.1 |
| 2012/0097565 A1 | 4/2012 | Dix et al. |
| 2012/0189621 A1 | 7/2012 | Dean et al. |
| 2012/0225060 A1 | 9/2012 | Lee et al. |
| 2012/0253016 A1 | 10/2012 | Igawa et al. |
| 2012/0301462 A1 | 11/2012 | Cruwys |
| 2013/0017575 A1 | 1/2013 | Garcia-Martinez et al. |
| 2013/0224109 A1 | 8/2013 | Strom et al. |
| 2013/0280266 A1 | 10/2013 | Rajpal et al. |
| 2014/0141013 A1 | 5/2014 | Giles-Komar et al. |
| 2014/0302058 A1 | 10/2014 | Bowen et al. |
| 2015/0125468 A1 | 5/2015 | Schmidt et al. |
| 2015/0140011 A1 | 5/2015 | Blanchetot et al. |
| 2015/0197568 A1 | 7/2015 | Cruwys et al. |
| 2015/0203574 A1 | 7/2015 | Rajpal et al. |
| 2015/0239970 A1 | 8/2015 | Bee et al. |
| 2015/0246092 A1 | 9/2015 | Wilson et al. |
| 2015/0337036 A1 | 11/2015 | Garcia-Martinez et al. |
| 2016/0017032 A1 | 1/2016 | Westerman et al. |
| 2016/0017056 A1 | 1/2016 | Clube |
| 2016/0130340 A1 | 5/2016 | Smith |
| 2016/0159896 A1 | 6/2016 | Clube |
| 2016/0168243 A1 | 6/2016 | Smith |
| 2016/0176956 A1 | 6/2016 | Cong et al. |
| 2016/0355584 A1 | 12/2016 | Wagner et al. |
| 2017/0029499 A1* | 2/2017 | Kakkar ............... C12Q 1/6886 |
| 2019/0241650 A1 | 8/2019 | Devalaraja et al. |
| 2019/0248886 A1 | 8/2019 | Devalaraja et al. |
| 2020/0079846 A1 | 3/2020 | Testani et al. |
| 2021/0292405 A1 | 9/2021 | Kakkar et al. |

FOREIGN PATENT DOCUMENTS

| | | |
|---|---|---|
| AU | 2019268074 A1 | 12/2019 |
| CA | 2991637 A1 | 2/2017 |
| CA | 3051865 A1 | 8/2018 |
| CN | 101883588 A | 1/2010 |
| CN | 101641374 A | 2/2010 |
| CN | 108026582 A | 5/2018 |
| CN | 110913900 A | 3/2020 |
| EA | 201890185 A1 | 7/2018 |
| EP | 0399429 A1 | 11/1990 |
| EP | 0410813 B1 | 1/1996 |
| EP | 1536012 A1 | 1/2005 |
| EP | 1977763 A1 | 10/2008 |
| EP | 1715891 B1 | 4/2010 |
| EP | 3329018 A1 | 6/2018 |
| EP | 3576790 A1 | 12/2019 |
| EP | 3888752 | 10/2021 |
| HK | 1249923 A1 | 7/2018 |
| IN | 201817000037 A | 3/2018 |
| IN | 201917034989 A | 8/2019 |
| JP | H10-66582 | 3/1998 |
| JP | 2005-501514 A | 1/2005 |
| JP | 2007-524602 A | 8/2007 |
| JP | 2007-528691 | 10/2007 |
| JP | 2008-538931 A | 11/2008 |
| JP | 2010-510795 A | 4/2010 |
| JP | 2012-516158 A | 7/2012 |
| JP | 2014-001216 A | 1/2014 |
| JP | 2018529756 A | 10/2018 |
| JP | 2020-506190 | 2/2020 |
| KR | 20180058708 A | 6/2018 |
| MX | 2018000778 A | 8/2018 |
| NZ | 739392 A | 10/2019 |
| RU | 2195960 C2 | 1/2003 |
| RU | 2318829 C2 | 3/2008 |
| SG | 11201906852X A | 8/2019 |
| TW | 201832780 A | 9/2018 |
| TW | 1653339 B | 3/2019 |
| TW | 201928063 A | 7/2019 |
| WO | WO 2003/055979 A3 | 10/2003 |
| WO | WO 2004/003019 | 1/2004 |
| WO | WO 2004/039826 A1 | 5/2004 |
| WO | WO 2004/045507 A2 | 6/2004 |
| WO | WO 2004/020633 A1 | 11/2004 |
| WO | WO 2005/028514 A1 | 3/2005 |
| WO | WO 2005/080429 A2 | 9/2005 |
| WO | WO 2006/072954 A2 | 7/2006 |
| WO | WO 2006/119115 A3 | 11/2006 |
| WO | WO 2006/122825 A2 | 11/2006 |
| WO | WO 2006/130834 A2 | 12/2006 |
| WO | WO 2007/066082 A2 | 6/2007 |
| WO | WO 2007/106811 A2 | 9/2007 |
| WO | WO 2008/065378 A2 | 6/2008 |
| WO | WO 2008/086395 A2 | 7/2008 |
| WO | WO 2008/144763 A2 | 11/2008 |
| WO | WO 2008/156807 A2 | 12/2008 |
| WO | WO 2009/003019 A1 | 12/2008 |
| WO | WO 2009/026158 A2 | 2/2009 |
| WO | WO 2009/140348 A2 | 11/2009 |
| WO | WO 2010/065072 A1 | 6/2010 |
| WO | WO 2010/088444 A1 | 8/2010 |
| WO | WO 2011/066369 A2 | 6/2011 |
| WO | WO 2002/060919 A2 | 8/2012 |
| WO | WO 2014/066468 A1 | 5/2014 |
| WO | WO 2014/074823 A1 | 5/2014 |
| WO | WO 2018/144773 A1 | 8/2018 |

OTHER PUBLICATIONS

Nakamura et al. Blockade of Interleukin 6 Signaling Induces Marked Neutropenia in Patients with Rheumatoid Arthritis. Journal of Rheumatology, 2009; 32(2):459 (Year: 2009).*
AstraZeneca. Study to assess the safety and tolerability of MEDI5117 in rheumatoid arthritis patients. Available from https://clinicaltrials.gov/ct2/history/NCT01559103?A=9&B=9&C=merged#StudyPageTop). NLM identifier: NCT01559103. Submitted Feb. 19, 2015) (Year: 2015).*
University of Colorado. A Study of Patients with Chronic Kidney Disease to Assess the Safety of a Single Dose of COR-001 (COR-001-SCI). Available from https://clinic3ltriais.Rov/ct2/show/NCT03126318). NLM identifier: NCT03126318. First posted Apr. 24, 2017 (Year: 2017).*
Huizinga, T.W.J et al., "Sarilumab, a Fully Human Monoclonal Antibody Against IL-6Ra in with Rheumatoid Arthritis and an Inadequate Response to Methotrexate: Efficacy and Safety Results from the Randomised SARIL-RA-MOBIUTY Part A trial," Annals of the Rheumatic Diseases, Dec. 2, 2013, vol. 73, No. 9, pp. 1626-1634.
Illei et al. "Tocilizuman in Systemic Lupus Erythematosus—Safety, Preliminary Efficacy, and Impact on Circulating Plasma Cells," Arthritis and Rheumatism, Feb. 1, 2010, vol. 62, No. 2, pp. 542-552.
PCT International Search Report and Written Opinion, PCT Application No. PCT/US2019/012430, dated May 3, 2019, 14 pages.
Ahmad T. et al., Charting a Roadmap for Heart Failure Biomarker Studies. JACC: Heart Failure, 2014, pp. 477-888, vol. 2, No. 5.
Alegre, M-L. et al., "A Non-Activating "Humanized" Anti-CD3 Monoclonal Antibody Retains Immunosuppresive Properties in Vivo," Transplantation, 1994, pp. 1537-1543, vol. 57.
Andrews, N.C., "Anemia of Inflammation: The Cytokine-Hepcidin Link," The Journal of Clinical Investigation, May 2004, pp. 1251-1253, vol. 113, No. 9.

(56) References Cited

OTHER PUBLICATIONS

Armour, K.L. et al., "Recombinant Human IgG Molecules Lacking Fcy Receptor I Binding and Monocyte Triggering Activities," Eur. J. Immunol., 1999, pp. 2613-2624, vol. 29.
Asperti, M. et al., "High Sulfation and a High Molecular Weight are Important for Anti-Hepcidin Activity of Heparin," Frontiers in Pharmacology, Jan. 2016, pp. 1-6, vol. 6, Article 316.
Barany, P. et al., "High C-reactive Protein is a Strong Predictor of Resistance to Erythropoietin in Hemodialysis Patients," American Journal of Kidney Diseases, Apr. 1997, pp. 565-568, vol. 29, No. 4.
Bataille, R. et al., "Biologic Effects of Anti-Interleukin-6 Murine Monoclonal Antibody in Advanced Multiple Myeloma", Blood, 1995, pp. 685-691, vol. 86, No. 2.
Bayliss, T.J. et al., "A Humanized Anti-IL-6 Antibody (ALD518) in Non-Small Cell Lung Cancer," Expert Opin. Biol Ther., Dec. 2011, pp. 1663-1668, vol. 11, No. 12.
Bell, S. J. et al., "Review Article: The Clinical Role of Anti-TNF. Alpha. Antibody Treatment in Crohn's Disease", Aliment Pharmacol. Ther., 2000, pp. 501-514, vol. 14.
Bendig, M. M., "Humanization of Rodent Monocolonal Antibodies by CDR Grafting," Methods: A Companion to Methods in Enzymology, 1995, pp. 83-93, vol. 8.
Benyamin, B. et al., "Common Variants in TMPRSS6 are Associated with Iron Status and Erythrocyte Volume," Nature Genetics, Nov. 2009, pp. 1173-1175, vol. 41, No. 11.
Besarab, A. et al., "The Effects of Normal as Compared with Low Hematocrit Values in Patients with Cardiac Disease Who Are Receiving Hemodialysis and Epoetin," New England Journal of Medicine, Aug. 27, 1998, pp. 584-590, vol. 339, No. 9.
Blay, J.-Y. et al., "Role of lnterleukin-6 in the Paraneoplastic Inflammatory Syndrome Associated With Renal-Cell Carcinoma," Int. J. Cancer, 1997, pp. 424-430, vol. 72.
Bongartz, L.G. et al., "The Severe Cardiorenal Syndrome: 'Guyton revisited'," European Heart Journal, 2005, pp. 11-17, vol. 26.
Boulanger, M.J. et al., "Hexameric Structure and Assembly of the lnterleukin-6/IL-6 .alpha.-Receptor/gp130 Complex," Science, 2003, pp. 2101-2104, vol. 300.
Braam, B. et al., "Cardiorenal Syndrome—Current Understanding and Future Perspectives," Nature Reviews Nephrology, Jan. 2014, pp. 48-55, vol. 10.
Bradel-Tretheway, B.G. et al., "Effects of Codon-Optimization on Protein Expression by the Human Herpesvirus 6 and 7 U51 Open Reading Frame," Journal of Virological Methods, 2003, pp. 145-156, vol. 111.
Brakenhoff Just P. J. et al., "Development of a Human lnterleukin-6 Receptor Antagonist", The Journal of Biological Chemistry, 1994, pp. 86-93, vol. 269, No. 1.
Brakenhoff, Just P. J et al., "Structure-Function Analysis of Human IL-6 Epitope Mapping of Neutralizing Monoclonal Antibodies with Amino-and Carboxyl-Treatment Deletion Mutants," The Journal of Immunology, 1990, pp. 561-568, vol. 145, No. 2.
Brands, M.W. et al., "Interleukin 6 Knockout Prevents Angiotensin II Hypertension: Role of Renal Vasoconstriction and Janus Kinase 2/Signal Transducer and Activator of Transcription 3 Activation," Hypertension, Nov. 2010, pp. 879-884, vol. 56.
Brochier, J. et al., "Immunomodulating IL-6 Activity by Murine Monoclonal Antibodies", Int. J. Immunopharm, 1995, pp. 41-48, vol. 17, No. 1.
Brorson, K. et al., "Mutational Analysis of Avidity and Fine Specificity of Anti-Levan Antibodies," J. Immunol., 1999, pp. 6694-6701, vol. 163.
Brummell, D.A. et al., "Probing the Combining Site of an Anti-Carbohydrate Antibody by Saturation-Mutagenesis: Role of the Heavy-Chain CDR3 Residues," Biochemistry, 1993, pp. 1180-1187, vol. 32.
Burks, E.A. et al., "In Vitro Scanning Saturation Mutagenesis of an Antibody Binding Pocket," Proc.Natl. Acad. Sci., Jan. 1997, pp. 412-417, vol. 94.

Calabrese, L.H. et al., "The New and Evolving Science of IL-6 in Rheumatoid Arthritis: The Contributions of IL-6 to Disease Manifestations of RA," 2015, Sanofi and Regeneron Pharmaceuticals, Inc., 16 pages.
Caldas, C. et al., "Humnization of the Anti-CD18 Antibody 6.7: An Unexpected Effect of a Framework Residue in Binding to Antigen," Mol. Immunol., May 2003, pp. 941-952, vol. 39, No. 15.
Casadevall, A. et al., "Immunoglobulin Isotype Influences Affinity and Specificity," Proceedings of the National Academy of Sciences, Jul. 31, 2012, pp. 12272-12273, vol. 109, No. 31.
Casanovas, G. et al., "A Multi-Scale Mode of Hepcidin Promoter Regulation Reveals Factors Controlling Systemic Iron Homeostasis," PLOS Computational Biology, Jan. 2014, pp. 1-13, vol. 10, Issue 1, e1003421.
Casper, C. et al., "Analysis of Inflammatory and Anemia-Related Biomarkers in a Randomized, Double-Blind, Placebo-Controlled Study of Siltuximab (Anti-IL6 Monoclonal Antibody) in Patients with Multicentric Castleman Disease," Clinical Cancer Research, Oct. 1, 2015, pp. 4294-4304, vol. 21, No. 19.
Casset, F. et al., "A Peptide Mimetic of an Anti-CD4 Monoclonal Antibody by Rational Design," Biochemical and Biophysical Research Communications, 2003, pp. 198-205, vol. 307.
Castagna, A. et al., "Hepcidin Assay in Serum by SELDI-TOF-MS and Other Approaches," Journal of Proteomics, 2010, pp. 527-536, vol. 73.
Chambers, J.C. et al., "Genome-Wide Association Study Identifies Variants in TMPRSS6 Associated with Hemoglobin Levels," Nature Genetics, Nov. 2009, pp. 1170-1172, vol. 41, No. 11.
"Chapter 4: Hospitalization," United States Renal Data System, 2017 USRDS Annual Data Report, ESRD in the United States, 2017, pp. 321-336, vol. 2. May be viewed at<URL: www.usrds.org/2017/view/v204.aspx>.
Chaouat, A. et al., "Role for the lnterleukin-6 in COPD-Related Pulmonary Hypertension," Chest, 2009, pp. 678-687, vol. 136, No. 3.
Chen, Y. et al., "Selection and Analysis of an Optimized Anti-VEGF Antibody: Crystal Structure of an Affinity-Matured Fab in Complex with Antigen," J. Mol. Bio., 1999, pp. 865-881, vol. 293.
Chien, N.C. et al., "Significant Structural and Functional Change of an Antigen-Binding Site by a Distant Amino Acid Substitution: Proposal of a Structural Mechanism," Proc. Natl. Acad. Sci. USA. Jul. 1989, pp. 5532-5536, vol. 86, No. 14.
Chonchol, M., "Neutrophil Dysfunction and Infection Risk in End-Stage Renal Disease," Seminars in Dialysis, Jul.-Aug. 2006, pp. 291-296, vol. 19, No. 4.
Choy, E., "Clinical experience with inhibition of interluekin-6", Rheumatic Disease Clinics of North America, 2004, pp. 405-415, vol. 30.
Clementi, A. et al., "Cardiorenal Syndrome Type 4: A Review," CardioRenal Medicine, 2013, pp. 63-70, vol. 3.
Colman P. M., "Effects of Amino Acid Sequence Changes on Antibody—Antigen Interactions," Research in Immunology, 1994, pp. 33-36, vol. 145.
Colombo, P.C et al., "Inflammatory Activation: Cardiac, Renal, and Cardio-Renal Interactions in Patients with the Cardiorenal Syndrome," Heart Fail Rev., 2012, pp. 177-190, vol. 17.
Constantinou, A. et al., "Site-specific polysialylation of an antitumor single-chain Fv fragment," Bioconjug. Chem., 2009, vol. 20, pp. 924-931.
Coyne, D.W. et al., DRIVE Study Group, "Ferric Gluconate is Highly Efficacious in Anemic Hemodialysis Patients with High Serum Ferritin and Low Transferrin Saturation: Results of the Dialysis Patients' Response to IV Iron with Elevated Ferritin (DRIVE) Study," Journal of the American Society of Nephrol 2007, pp. 975-984, vol. 18,No. 3.
Dall'Acqua, W. F. et al., "Increasing the Affinity of a Human IgG1 for the Neonatal Fc Receptor: Biological Consequences," The Journal of Immunology, 2002, pp. 5171-5180, vol. 169.
Dall'Acqua, W. F. et al., "Properties of Human IgG1s Engineered for Enhanced Binding itothe Neonatal Fc Receptor (FcRn)," Journal of Biological Chemistry, 2006, pp. 23514-23524, vol. 281, No. 33.

(56) References Cited

OTHER PUBLICATIONS

Damman, K. et al., "Worsening Renal Function and Prognosis in Heart Failure: Systematic Review and Meta-Analysis," Journal of Cardiac Failure, 2007, pp. 599-608, vol. 13, No. 8.

Datta-Mannan, A. et al., "Humanized $IgG_1$ Variants with Differential Binding Properties to the Neonatal Fc Receptor: Relationship to Pharmacokinetics in Mice and Primates," Drug Metabolism and Disposition, 2007, pp. 86-94, vol. 35, No. 1.

Datta-Mannan, A. et al., "Monoclonal Antibody Clearance: Impact of Modulating The Interaction of IgG With the Neonatal Fc Receptor", Journal of Biological Chemistry, 2007, pp. 1709-1717, vol. 282, No. 3.

Davies, J. et al., "Affinity Improvement of Single Antibody VH Domains: Residues in all Three Hypervariable Regions Affect Antigen Binding", Immunotechnology, 1996, pp. 169-179, vol. 2.

De Francisco et al. Inflammation and its impact on anemia in chronic kidney disease: from haemoglobin variability to hyporesponsiveness. NOT Plus. Jan. 2009; 2(Suppl 1 ): i18-i26.

De Pascalis, R. et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, 2002, pp. 3076-3084, vol. 169, No. 6.

Desgeorges, A. et al., "Concentrations and Origins of Soluble Interleukin 6 Receptor-.alpha, in Serum and Synovial Fluid", The Journal of Rheumatology, 1997, pp. 1510-1516, vol. 24.

Duncan, A.R. et al., "Localization of the Binding Site for the human High-Affinity Fc Receptor on IgG," Nature, Apr. 7, 1988, pp. 563-564, vol. 332.

Eddahibi, S. et al., "lnterleukin-6 Gene Polymorphism Confers Susceptibility to Pulmonary Hypertension in Chronic Obstructive Pulmonary Disease," Proceedings of the American Thoracic Society, 2006, pp. 475-476, vol. 3, No. 6.

Eickhoff, P. et al., "Determinants of Systemic Vascular Function in Patients with Stable Chronic Obstructive Pulmonary Disease," American Journal of Respiratory and Critical Care Medicine, 2008, pp. 1211-1218, vol. 178, No. 12.

Emilie, D. et al., "Administration of an Anti-lnterleukin-6 Monoclonal Antibody to Patients With Acquired Immunodeficiency Syndrome and Lymphoma: Effect on Lymphoma Growth and on B Clinical Symptoms", Blood, 1994, pp. 2472-2479, vol. 84, No. 8.

Ernst, M. et al., "Acquiring signalling specificity from the cytokine receptor gp130", Trends in Genetics, 2004, pp. 23-32, vol. 20, No. 1.

Fagnani, R. et al., "Altered pharmacokinetic and tumour localization properties of Fab'fragments of a murine monoclonal anti-CEA antibody by covalent modification with low molecular weight dextran," Nuclear medicine communications, 1995, vol. 16, No. 5, pp. 362-369.

Fasshauer, M. et al., "Interleukin (IL)-6 mRNA Expression is Stimulated by Insulin, Isoproterenol, Tumour Necrosis Factor Alpha, Growth Hormone, and IL-6 in 3T3-L1 Adipocytes", Horm Metab Res, 2003, pp. 147-152, vol. 35.

Finberg, K.E. et al., "Mutations in TMPRSS6 Cause Iron-Refractory Iron Deficiency Anemia (IRIDA), Nature Genetics, May 2008, pp. 569-571, vol. 40, No. 5.

Finch, D.K. et al., "Whole-Molecule Antibody Engineering: Generation of a High-Affinity Anti-IL-6 Antibody with Extended Pharmacokinetics," Journal of Molecular Biology, 2011, pp. 791-807, vol. 411.

Fishbane, S. et al., "Mechanism of Increased Mortality Risk with Erythropoietin Treatment to Higher Hemoglobin Targets," Clin J Am Soc Nephrol, 2007, pp. 1274-1282, vol. 2.

Fulciniti, M. et al., "A High-Affinity Fully Human Anti-IL-6 mAb, 1339, for the Treatment of Multiple Myeloma," Clin Cancer Res., Dec. 1, 2009, pp. 7144-7152, vol. 15, No. 23.

Fung, E. et al., "Manipulation of the Hepcidin Pathway for Therapeutic Purposes," Haematologica, Nov. 2013, pp. 1667-1676, vol. 98, No. 11.

Gabriel A.S. et al., "IL-6 Levels in Acute and Post Myocardial Infarction: Their Relation to CRP Levels, Infarction Size, Left Ventricular Systolic Function, and Heart Failure" European Journal of Internal Medicine, Dec. 2004, pp. 523-528, vol. 15, No. 8.

Ganz, T. et al., "Hepcidin and Iron Regulation, 10 Years Later," Blood, Apr. 28, 2011, pp. 4425-4433, vol. 117, No. 17.

Ganz, T. et al., "Iron Homeostatis in Host Defence and Inflammation," Nature Reviews, Aug. 2015, pp. 500-510, vol. 15.

Ghetie, V. et al., "Increasing the Serum Persistence of an IgG Fragment by Random Mutagenesis," Nature Biotechnology, Jul. 1997, pp. 637-640, vol. 15, No. 7.

Giusti, A.M. et al., "Somatic Diversification of S107 from an Antiphosphocholine to an Anti-DNA Autoantibody is Due to a Single Base Change in its Heavy Chain Variable Region," Proc. Natl. Acad. Sci. USA, May 1987, pp. 2926-2930, vol. 84, No. 9.

Golembeski, S.M. et al., "lnterleukin-6 Causes Mild Pulmonary Hypertension and Augments Hypoxia-Induced Pulmonary Hypertension in Mice," Chest, 2005, p. 572S-573S, vol. 128 (6 Suppl).

Groenewegen, K.H. et al., "Longitudinal Follow-Up of Systemic Inflammation After Acute Exacerbations of COPD," Respiratory Medicine, 2007, pp. 2409-2415, vol. 1 OJ, No. 11.

Guillen, C. et al., "The Interleukin-6/Soluble Interleukin-6 Receptor System Induces Parathyroid Hormone-Related Protein in Human Osteoblastic Cells", Calcified Tissue International, 2004, pp. 153-159, vol. 75.

Gussow, D. et al., "Humanization of Monoclonal Antibodies," Methods in Enzymology,1991, pp. 99-121, vol. 203.

Haddad, E. et al., "Treatment of B-Lymphoproliferative Disorder with a Monoclonal Anti-lnterleukin-6 Antibody in 12 Patients: A Multicenter Phase 1-2 Clinical Trial," Blood, 2001, pp. 1590-1597, vol. 97, No. 6.

Hanberg, J. et al., "Hypochloremia and Diuretic Resistance in Heart Failure: Mechanistic Insights," Circulation: Heart Failure, Aug. 2016, vol. 9, Issue 8, pp. 1-12.

Hashizume, M. et al., "Tocilizumab, a Humanized Anti-lnterleukin-6 Receptor Antibody, Improved Anemia in Monkey Arthritis by Suppressing IL-6-Induced Hepcidin Production," Rheumatology International, Jul. 29, 2009, pp. 917-923, vol. 30, No. 7.

Heinrich, P. C., et al., "Principles of Interleukin (IL)-6-Type Cytokine Signalling and its Regulation", Biochem. J., 2003, pp. 1-20, vol. 374.

Hentze, M.W. et al., "Balancing Acts: Molecular Control of Mammalian Iron Metabolism," Cell, Apr. 30, 2004, pp. 285-297, vol. 117.

Hentze, M.W. et al., "Two to Tango: Regulation of Mammalian Iron Metabolism," Cell, Jul. 9, 2010, pp. 24-38, vol. 142.

Heymans, S. et al., "Inflammation as a Therapeutic Target in Heart Failure? A Scientific Statement from the Translational Research Committee of the Heart Failure Association of the European Society of Cardiology," European Journal of Heart Failure, 2009, pp. 119-129, vol. 11.

Hibi, M. et al., "Molecular Cloning and Expression of an IL-6 Signal Transducer, gp130," Cell, Dec. 21, 1990, pp. 1149-1157, vol. 63.

Hinton, P. R et al., "An Engineered Human IgGl Antibody with Longer Serum Half-Life", The Journal of Immunology, 2006, pp. 346-356, vol. 176.

Hinton, P. R. et al., "Engineered Human IgG Antibodies with Longer Serum Half-Lives in Primates*", The Journal of Biological Chemistry, 2004, pp. 6213-6216, vol. 279, No. 8.

Hirano, T. et al., "Complementary DNA for a novel human interleukin (BSF-2) that induces B lymphocytes to produce immunoglobulin", Nature, 1986, pp. 73-76, vol. 324.

Hirata, Y. et al., "Characterization of IL-6 Receptor Expression by Monoclonal and Polyclonal Antibodies", The Journal of Immunology, 1989, pp. 2900-2906, vol. 143.

Holm, P. et al., "Functional Mapping and Single Chain Construction of the Anti-Cytokeratin 8 Monoclonal Antibody TS1," Molecular Immunology Feb. 2007, pp. 1075-1084, vol. 44, No. 6.

Holt L.J. et al., "Domain Antibodies: Proteins for Therapy", Trends in Biotechnology, 2003, pp. 484-490, vol. 21, No. 11.

(56) References Cited

OTHER PUBLICATIONS

Hou, H. et al., "Association of lnterleukin-6 Gene Polymorphism with Coronary Artery Disease: an Updated Systematic Review and Cumulative Meta-Analysis," Inflamm. Res., Sep. 2015, pp. 707-720, vol. 64, No. 9.

Hung, AM., et al., "IL-1B Receptor Antagonist Reduces Inflammation in Hemodialysis Patients," J Am Soc Nephrol, 2011, pp. 437-442. vol. 22.

Hutchins et al., "Improved Biodistribution, Tumor Targeting, and Reduced Immunogenicity in Mice with a γ4 Variant of Campath-1 H," Proc Natl. Acad Sci USA, Dec. 1995, pp. 11980-11984, vol. 92.

Idusogie et al., "Engineered Antibodies with Increased Activity to Recruit Complement," The Journal of Immunology, 2001, pp. 2571-2575, vol. 166.

Idusogie et al., "Mapping of the C1q Binding Site on Rituxan, a Chimeric Antibody with a Human IgG1 Fc," The Journal of Immunology, 2000, pp. 4178-4184, vol. 164.

Illman, J., et al. "Are Inflammatory Cytokines the Common Link Between Cancer-Associated Cachexia and Depression?" The Journal of Supportive Oncology, 2005, pp. 37-50, vol. 3, No. 1.

Isaacs, J.D. et al., "Effect of Tocilizumab on Haematological Markers Implicates Interleukin-6 Signalling in the Anaemia of Rheumatoid Arthritis," Arthritis Research & Therapy, 2013, 6 pages, vol. 15, No. R204.

Jang, Y.-J. et al., "The Structural Basis for DNA Binding by an Anti-DNA Autoantibody," Molecular Immunology, 1998, pp. 1207-1217, vol. 35.

Jefferis, R. et al., "Interaction Sites on Human IgG-Fc for FcγR: Current Models," Immunology Letters, 2002, pp. 57-65, vol. 82.

Jefferis, R. et al., "Modulation of FCγR and Human Complement Activation by IgG3-Core Oligosaccharide Interactions," Immunology Letters, 1996, pp. 101-104, vol. 54.

Jefferis, R. et al., "Recognition Sites on Human IgC for Feγ Receptors: the Role of Glycosylation," Immunology Letters, 1995, pp. 111-117, vol. 44.

Johnston, R.A. et al., "Role of the lnterleukin-6 in Murine Airway Responses to Ozone," Am. J.Physiol. Lung Cell Mol. Physiol., 2005, pp, L390-L397, vol. 288, No. 2.

Jones S. A. et al., "The Soluble Interleukin 6 Receptor: Mechanisms of Production and Implications in Disease", FASEB J., 2001, pp. 43-48, vol. 15.

Jones, S.A. et al., "Therapeutic Strategies for the Clinical Blockade of IL-6/gp 130 Signaling," The Journal of Clinical Investigation, pp. Sep. 2011, pp. 3375-3383, vol. 121, No. 9.

Julian, M. et al., "Efficient Affinity Maturation of Antibody Variable Domains Requires Co-Selection of Compensatory Muttions to Maintain Thermodynamic Stability," Scientific Reports, Mar. 28, 2017, pp. 1-13.

Kalai, M. et al., "Analysis of the Human Interleukin-6/Human lnterleukin-6 Receptor Binding Interface at the Amino Acid Level: Proposed Mechanism of Interaction", Blood, 1997, pp. 1319-1333, vol. 89, No. 4.

Kalai, M. et al., "Analysis of the Mechanism of Action of Anti-Human lnterleukin-6 and Anti-Human Tnterleukin-6 Receptor-Neutralising Monoclonal Antibodies", Eur. J. Biochem., 1997, pp. 690-700, vol. 249.

Kalai, M. et al., "Participation of Two Ser-Ser-Phe-Tyr Repeats in lnterleukin-6 (IL-6)-Binding Sites of the Human IL-6 Receptor", Eur. J. Biochem., 1996, pp. 714-723, vol. 238.

Kalantar-Zadeh, K. et al., "Effect of Malnutrition-Inflammation Complex Syndrome on EPO Hyporesponsiveness in Maintenance Hemodialysis Patients," American Journal of Kidney Diseases, Oct. 2003, pp. 761-773, vol. 42.

Kalantar-Zadeh, K. et al., "Time-Dependent Associations Between Iron and Mortality in Hemodialysis Patients," Journal ofthe American Society of Nephrology, Oct. 2005, pp. 3070-3080, vol. 16, No. 10.

Kawano, M. et al., "Autocrine Generation and Requirement of BSF-2/IL-6 for Human Multiple Myelomas", Nature, 1988, pp. 83-85, vol. 332.

Keller, E. T. et al., "Molecular and Cellular Biology of lnterleukin-6 and Its Receptor", Frontiers in Bioscience, 1996, pp. 340-357, vol. 1.

Kharagjitsingh, AV. et al., "Incidence of Recombinant Erythropoietin (EPO) Hyporesponse, EPO-Associated Antibodies, and Pure Red Cell Aplasia in Dialysis Patients," Kidney International, 2005, pp. 1215-1222, vol. 68, No. 3.

Kielar, M.L. et al., "Maladaptive Role of IL-6 in Ischemic Acute Renal Railure," Journal ofthe American Society of Nephrology, 2005, pp. 3315-3325, vol. 16.

Kilpatrick, R.D. et al., "Greater Epoetin Alfa Responsiveness is Associated with Improved Survival in Hemodialysis Patients," Clinical Journal of the American Society of Nephrology, 2008, pp. 1077-1083, vol. 3, No. 4.

Kim, G.W. et al., "IL-6 Inhibitors for Treatment of Rheumatoid Arthritis: Past, Present and Future," Arch. Pharm. Res., Feb. 2015, pp. 575-584, vol. 38.

Kim, G.W., "Table 2: Tocilizumab and Investigational IL-6 Inhibitors," Springer, Feb. 2015, p. 580.

Kim, H-R. et al., "Serum Pro-Hepcidin Could Reflect Disease Actvity in Patients with Rhematoid Arthritis," J. Korean Med. Sci., 2010, pp. 348-352, vol. 25.

Kishimoto, T., "lnterleukin-6:Discovery of a Pleiotropic Cytokine", Arthritis Research & Therapy, 2006, , pp. Suppl.2:S2:1-6, vol. 8.

Kishimoto, T., "The Biology of Interleukin-6", Blood, 1989, pp. 1-10, vol. 74, No. 1.

Klouche, M. et al., "Novel Path to Activation of Vascular Smooth Muscle Cells: Up-Regulation of gp130 Creates an Autocrine Activation Loop by IL-6 and Its Soluble Receptor", The Journal of Immunology, 1999, pp. 4583-4589, vol. 163.

Kobayashi, H. et al., "Tryptophan H33 Plays an Important Role in Pyrimidine (6-4) Pyrimidine Photoproduct Binding by a High-Affinity Antibody," Protein Engineering, 1999, pp. 879-844, vol. 12.

Kovac, S. et al., "Anti-Hemojuvelin Antibody Corrects Anemia Caused by Inappropriately High Hepcidin Levels," Haematologica, 2016, 4 pages, vol. 101, No. e173.

Kumar, S. et al., "Molecular Cloning and Expression ofthe Fabs of Human Autoantibodies in *Escherichia coli*," The Journal of Biological Chemistry, 2000, pp. 35129-35136, vol. 275.

Lang, J.E et al., "Effect of Obesity on Pulmonary Inflammation Induced by Acute Ozone Exposure: Role of the lnterleukin-6," Am. J.Physiol. Lung Cell Mol. Physiol., 2008, pp. L1013-L1020, vol. 294, No. 5.

Levey, A,S, et al., "A New Equation to Estimate Glomerular Filtration Rate," Annals of Internal Medicine, May 5, 2009, pp. 604-612, vol. 150, No. 9.

Li, K. et al., "Interleukin-6 Stimulates Epithelial Sodium Channels in Mouse Cortical Collecting Duct Cells," Am J Physiol Regul Integr Comp Physiol, 2010, pp. R590-R595, vol. 299.

Lu, Z.R. et al., "Polymerizable Fab' antibody fragments for targeting of anticancer drugs," Nature Biotechnology, 1999, vol. 17, pp. 1101-1104.

Lu, Z. Y. et al., "Measurement of Whole Body Interleukin-6 (IL-6) Production: Prediction of the Efficacy of Anti-IL-6 Treatments", Blood, 1995, pp. 3123-3131, vol. 86, No. 8.

Lu, Z.Y. et al., "High Amounts of Circulating Interleukin (IL)-6 in the Form of Monomeric Immune Complexes During Anti-IL-6 Therapy. Toward a New Methodology for Measuring Overall Cytokine Production in Human in vivo," Eur. J. Immunol., 1992, pp. 2819-2824, vol. 22.

Lund, J. et al., "Human FcγRI and FCγRII Interact with Distinct but Overlapping Sites on Human IgG[1]," The Journal of Immunology, Oct. 15, 1991, pp. 2657-2662, vol. 147, No. 8.

Lund, J. et al., "Multiple Binding Sites on the CH2 Domain of IgG for Mouse FcγR11," Molecular Immunology, 1992, pp. 53-59, vol. 29, No. 1.

Lund, J. et al., "Multiple Interactions of IgG with Its Core Oligosaccharide Can Modulate Recognition by Complement and Human Fcγ Receptor I and Influence the Synthesis of Its Oligosaccharide Chains," The Journal of Immunology, Dec. 1, 1996, pp. 4963-4969, vol. 157, No. 11.

(56) References Cited

OTHER PUBLICATIONS

Lund, J. et al., "Oligosaccharide-Protein Interactions in IgG Can Modulate Recognition by Fcγ Receptors," The FASEB Journal, Jan. 1995, pp. 115-119, vol. 9, No. 1.

MacCallum, R.M. et al., "Antibody-Antigen Interactions: Contact Analysis and Binding Site Topography," J. Mol. Biol., 1996, pp. 732-745, vol. 262.

MacDougall, I.C. et al., "Hyporesponsiveness to Erythropoietic Therapy Due to Chronic Inflammation," European Journal of Clinical Investigation, 2005, pp. 32-35, vol. 35, Suppl 3.

Mariuzza, R.A. et al., "The Structural Basis of Antigen-Antibody Recognition," Annu. Rev. Biophys. Biophys. Chem., 1987, pp. 139-159, vol. 16.

Marz, P. et al., "Sympathetic Neurons Can Produce and Respond to Interleukin 6", Proc. Natl. Acad. Sci. USA, Mar. 1998, pp. 3251-3256, vol. 95.

Mateo, C. et al., "Humanization of a mouse monoclonal antibody that blocks the epidermal growth factor receptor: recovery of antagonistic activity," Immunotechnology 3, Jan. 31, 1997, pp. 71-81.

Melmed, C. et al., "Certolizumab pegol," Nature Reviews Drug Discovery, 2008, vol. 7, pp. 641-642.

Menziani, M.C. et al., "Theoretical Investigation of IL-6 Multiprotein Receptor Assembly", Proteins Structure, Function and Genetics, 1997, pp. 528-544, vol. 29.

Mihara, M. et al., "The Therapy of Autoimmune Diseases by Anti-Interleukin-6 Receptor Antibody", Expert Opinion on Biological Therapy, 2005, pp. 683-690, vol. 5, No. 5.

Mishra, A. et al., "Insights into the Structural Basis of Antibody Affinity Maturation from Next-Generation Sequencing," Frontiers in Immunology, vol. 9, Article 117, Feb. 1, 2018, pp. 1-10.

Modur, V. et al., "Retrograde Inflammatory Signaling from Neutrophils to Endothelial Cells by Soluble Interleukin-6 Receptor Alpha", J. Clin. Invest., 1997, pp. 2752-2756, vol. 100, No. 11.

Montero-Julian, F.A. et al., "Pharmacokinetic Study of Anti-Interleukin-6 (IL-6) Therapy with Monoclonal Antibodies: Enhancement of IL-6 Clearance by Cocktails of Anti-IL-6 Antibodies," Blood, 1995, pp. 917-924, vol. 85, No. 4.

Moshage, H., "Cytokines and the Hepatic Acute Phase Response", Journal of Pathology, 1997, pp. 257-266, vol. 181.

Murakami, M. et al., "Inducible Expression of Glial Fibrillary Acidic Protein in HT-1080 Human Fibrosarcoma Cells", Cell Growth & Differentiation, 1996, pp. 1697-1703, vol. 7.

Nai, A. et al., "Limiting Hepatic Bmp-Smad Signaling by Matriptase-2 is Required for Erythropoietin-Mediated Hepcidin Suppression in Mice," Blood, May 12, 2016, pp. 2327-2336, vol. 127, No. 19.

Nai, A. et al., "TMPRSS6 rs855791 Modulates Hepcidin Transcription in Vitro and Serum Hepcidin Levels in Normal Individuals," Blood, Oct. 20, 2011, pp. 4459-4462, vol. 118, No. 16.

Nechemia-Arbely, Y. et al., "IL-6/IL-6R Axis Plays a Critical Role in Acute Kidney Injury," J Am Soc Nephrol., 2008, pp. 1106-1115, vol. 19.

Nguyen, A. et al., "The pharmacokinetics of an albumin-binding Fab (AB. Fab) can be modulated as a function of affinity for albumin," Prot Eng Design Sel, 2006, vol. 19, pp. 291-297.

Nishimoto, N. et al., "Inhibition of IL-6 for the treatment of inflammatory diseases", Current Opinion in Pharmacology, 2004, pp. 386-391, vol. 4.

Oh, J.-W. et al., "CXC Chemokine Receptor 4 Expression and Function in Human Astroglioma Cells", The Journal of Immunology, 2001, pp. 2695-2704, vol. 166.

Panka, D.J. et al., "Variable Region Framework Differences Result in Decreased or Increased Affinity of Variant Anti-Digoxin Antibodies," Proceedings of the National Academy of Sciences, National Academy of Sciences, May 1, 1988, pp. 3080-3084, vol. 85, No. 9.

Patel, N.S. et al., "Endogenous Interleukin-6 Enhances the Renal Injury, Dysfunction, and Inflammation Caused by Ischemia/Reperfusion," The Journal of Pharmacology and Experimental Therapeutics, 2005, pp. 1170-1178, vol. 312, No. 3.

Paul, W. E., Fundamental Immunology, 3rd Edition, Raven Press, New York, Chapt. 8, 1993 pp. 292-295.

Pecoits-Filho, R et al., "Update on Interleukin-6 and Its Role in Chronic Renal Failure," Nephrol Dial Transplant, 2003, pp. 1042-1045, vol. 18.

Perera, W.R. et al., "Inflammatory Changes, Recovery and Recurrence at COPD Exacerbation," Eur. Respir. J., 2007, pp. 527-534, vol. 29, No. 3.

Petkova, S.B. et al., "Enhanced half-life of genetically engineered human IgG1 antibodies in a humanized FcRn mouse model: potential application in humorally mediated autoimmune disease," International Immunology, 2006, vol. 18, pp. 1759-1769.

Pietrangelo, A., "Hepcidin in Human Iron Disorders: Therapeutic Implications," Journal of Hepatology, 2011, pp. 173-181, vol. 54.

Poggiali E. et al., "The Role of TMPRSS6 Polymorphisms in Iron Deficiency Anemia Partially Responsive to Oral Iron Treatment" American Journal of Hematology, Dec. 31, 2014, pp. 306-309, vol. 90, No. 4.

Popp, A., "RGM—From Target Side Effects to a New Indication—Anemia of Chronic Disease," Biomarker Summit, Europe 2015, Oct. 5-8, 2015, 7 pages.

Presta, L.G. et al., "Engineering Therapeutic Antibodies for Improved Function," Biochemical Society Transactions, Aug. 2002, pp. 487-490, vol. 30, Part 4.

Rajpal, A. et al., "Introduction: Antibody Structure and Function," In: Therapeutic Fc-Fusion Proteins, Wiley-VCH Verlag GmbH & Co. KGaA, Feb. 19, 2014, pp. 1-44.

Reddy, M.P. et al., "Elimination of Fc Receptor-Dependent Effector Functions of a Modified IgG4 Monoclonal Antibody to Human CD4," The Journal of Immunology, 2000, pp. 1925-1933, vol. 164.

"Regeneron and Sanofi Announce Topline Results of Phase 3 Monotherapy Study Demonstrating Superiority of Sarilumab vs. Adalimumab in Patients with Active Rheumatoid Arthritis," Regeneron Pharmaceuticals, Inc., Mar. 11, 2016, 3 pages.

Rispens, T. et al., "Label-free assessment of high-affinity antibody-antigen binding constants. Comparison of bioassay, SPR, and PEIA-ellipsometry," Journal of Immunological Methods 365, Nov. 27, 2010, pp. 50-57.

Rispens, T. et al., "Nanomolar to sub-picomolar affinity measurements of antibody-antigen interactions and protein multimerizations: Fluorescence-assisted high-performance liquid chromatography," Analytical Biochemistry 437, Mar. 13, 2013, pp. 118-122.

Ronco, C. et al., "Cardiorenal Syndrome," Journal of the American College of Cardiology, 2008, pp. 1527-1539, vol. 52, No. 19.

Rosner, M.H. et al., "The Role of Inflammation in the Cardio-Renal Syndrome: a Focus on Cytokines and Inflammatory Mediators," Seminars in Nephrology Jan. 2012, pp. 70-78, vol. 32, No. 1.

Rs855791SNPedia, Last Modified Dec. 6, 2018, 4 pages, [Online] [Retrieved on Apr. 23, 2019] Retrieved from the Internet<URL:http://www.snpedia.com/index.php/Rs855791>.

Rubab, Z. et al., "Serum Hepcidin Levels in Patients with End-Stage Renal Disease on Hemodialysis," Saudi Journal of Kidney Diseases and Transplantation, 2015, pp. 19-25, vol. 26, No. 1.

Rudikoff, S. et al., "Single Amino Acid Substitution Altering Antigen-Binding Specificity," Proc. Natl. Acad. Sci. USA, Mar. 1982, pp. 1979-1983, vol. 79. No. 6.

Saito, F. et al., "Role of Interleukin-6 in Bleomycin-Induced Lung Inflammatory Changes in Mice," American Journal of Respiratory Cell and Molecular Biology, 2008, pp. 566-571, vol. 38, No. 5.

Sakai, R. et al., "Head-to-Head Comparison of the Safety of Tocilizumab and Tumor Necrosis Factor Inhibitors in Rheumatoid Arthritis Patients (RA) in Clinical Practice: Results from the Registry of Japanese RA Patients on Biologies for Long-Term Safety (REAL) Registry," Arthritis Research & Therapy, Jan. 2015, 10 pages, vol. 17:74.

Sarwar N. et al., "Interleukin-6 Receptor Pathways in Coronary Heart Disease: a Collaborative Meta-Analysis of 82 Studies," Lancet, Mar. 31, 2012, pp. 1205-1213, vol. 379.

Savale, L. et al., "Impact of Interleukin-6 on Hypoxia-Induced Pulmonary Hypertension and Lung Inflammation in Mice," Respiratory Research, 2009, vol. 10, No. 6, 13 pages.

(56) References Cited

OTHER PUBLICATIONS

Savale, L. et al., "Shortened Telomeres in Circulating Leukocytes of Patients with Chronic Obstructive Pulmonary Disease," American Journal of Respiratory Critical Care Medicine, 2009, pp. 566-571, vol. 179, No. 7.
Schier, R. et al., "Isolation of High-affinity Monomeric Human Anti-c-erbB-2 Single chain Fv Using Affinity-driven Selection," Journal of Molecular Biology 225, Jan. 12, 1996, pp. 28-43.
Schlapschy, M. et al., "Fusion of a recombinant antibody fragment with a homo-amino-acid polymer: effects on biophysical properties and prolonged plasma half-life," Prot Eng Design Sel, 2007, vol. 20, pp. 273-284.
Scinicariello, F. et al., "Rhesus Macaque Antibody Molecules: Sequences and Heterogeneity of Alpha and Gamma Constant Regions," Immunology, 2004, pp. 66-74, vol. 111.
Shields, R. L. et al., "High Resolution Mapping of the Binding Site on Human IgG 1 forFcyRI, FcyRII, FcyRIII, and FcRn and Design of IgGI Variants with Improved Binding to the FcyR*", The Journal of Biological Chemistry, 2001, pp. 6591-6604, vol. 276, No. 2.
Sieper, J. et al., "Sarilumab for the Treatment of Ankylosing Spondylitis: Results of a Phase II, Randomised, Double-Blind, Placebo-Controlled Study (ALIGN)," Ann Rheum Dis, 2015, pp. 1051-1057, vol. 74.
Singh, A.K., "Correction of Anemia with Epoetin Alfa in Chronic Kidney Disease," New England Journal of Medicine, Nov. 16, 2006, pp. 2085-2098, vol. 355, No. 20.
Slotki, I. et al., "Disorders of Sodium Balance.," Brenner & Rector's The Kidney 10th ed. Philadelphia, PA: Elsevier, 2016, pp. 390-459.
Smith, P. C. et al., "Interleukin-6 and prostate cancer progression" Cytokine and Growth Factor Reviews, 2001, pp. 33-40, vol. 12.
Smith, B.J. et al., "Prolonged in vivo residence times of antibody fragments associated with albumin," Bioconjug. Chem, 2001, vol. 12, pp. 750-756.
Smith-Gill, S.J. et al., "Contributions of Immunoglobulin Heavy and Light Chains to Antibody Specificity for Lysozyme and Two Haptens," The Journal of Immunology, 1987, pp. 4135-4144, vol. 139.
Somers, W. et al., "1.9 .ANG. Crystal Structure of Interleukin 6: Implications for a Novel Mode of Receptor Dimerization and Signaling", The EMBO Journal, 1997, pp. 989-997, vol. 16, No. 5.
Song, M-K. et al., "Light Chain of Natural Antibody Plays a Dominant Role in Protein Antigen Binding," Biochemical and Biophysical Research Communications, 2000, pp. 390-394, vol. 268.
Song, S.N. et al., "Comparative Evaluation of the Effects of Treatment with Tocilizumab and TNF-a Inhibitors on Serum Hepcidin, Anemia Response and Disease Activity in Rheumatoid Arthritis Patients," Arthritis Research & Therapy, Oct. 2, 2013, 10 pages, R141, vol. 15, No. 5.
Song, S.N. et al., "Down-Regulation of Hepcidin Resulting from Long-Term Treatment with an Anti-IL-6 Receptor Antibody (Tocilizumab) Improves Anemia of Inflammation in Multicentric Castleman Disease," Blood, Nov. 4, 2010, pp. 3627-3634, vol. 116, No. 18.
Steinbicker, A.U. et al., "Inhibition of Bone Morphogenetic Protein Signaling Attenuates Anemia Associated with Inflammation," Blood, May 5, 2011, pp. 4915-4923, vol. 117, No. 18.
Steiner, M.K. et al., "Interleukin-6 Overexpression Induces Pulmonary Hypertension," Circulation Research, Jan. 2009, pp. 236-244, vol. 104, No. 2.
Stork, R. et al., "A novel tri-functional antibody fusion protein with improved pharmacokinetic properties generated by fusing a bispecific single-chain diabody with an albumin-binding domain from streptococcal protein G," Prot Eng. Design Science, 2007, vol. 20, pp. 569-576.
Sun, C.C. et al., "Targeting the Hepcidin-Ferroportin Axis to Develop New Treatment Strategies for Anemia of Chronic Disease and Anemia of Inflammation," American Journal of Hematology, 2012, pp. 392-400, vol. 87, No. 4.
Sylvant Label, [undated], Reference ID: 3493425, 16 pages.
Szymanski, M.K. et al., "Animal Models of Cardiorenal Syndrome: A Review," Heart Fail. Rev., 2012, pp. 411-420, vol. 17.
Tamura, T. et al., "Soluble lnterleukin-6 Receptor Triggers Osteoclast Formation by Interleukin 6", Proc. Natl. Acd. Sci. USA, 1993, pp. 11924-11928, vol. 90.
Tanaka et al. A genome-wide association analysis of serum iron concentrations. Blood. Jan. 7, 2010; 115(1):94-6.
Tanaka, T. et al., "A New Era for the Treatment of Inflammatory Autoimmune Diseases by Interleukin-6 Blockade Strategy," Seminars in Immunology, 2014, pp. 88-96, vol. 26.
Tanaka, Y. et al., "IL-6 Targeting Compared to TNF Targeting in Rheumatoid Arthritis: Studies of Olokizumab, Sarilumab and Sirukumab," Ann Rheum Dis, Sep. 2014, pp. 1595-1597, vol. 73, No. 9.
"Third Party Email 11292017," Nov. 29, 2017, 1 page.
Thorleifesson, S.J. et al., "Chronic Airflow Obstruction and Markers of Systemic Inflammation: Results from the BOLD Study in Iceland," Respiratory Medicine, 2009, pp. 1548-1553, vol. 103, No. 10.
Udagawa, N. et al., "Interleukin (IL)-6 Induction of Osteoclast Differentiation Depends on IL-6 Receptors Expressed on Osteoblastic Cells But Not on Osteoclast Progenitors", J. Exp. Med., 1995, pp. 1461-1468.
United States Office Action, U.S. Appl. No. 13/146,278, dated Dec. 19, 2013, 40 pages.
United States Office Action, U.S. Appl. No. 14/253,161, dated Feb. 26, 2016, 15 pages.
United States Office Action, U.S. Appl. No. 14/253,161, dated Jul. 28, 2015, 23 pages.
United States Office Action, U.S. Appl. No. 14/253,161, dated Sep. 2, 2016, 18 pages.
United States Office Action, U.S. Appl. No. 14/437,585, dated Dec. 28, 2016, 9 pages.
United States Office Action, U.S. Appl. No. 14/675,980, dated Sep. 19, 2016, 36 pages.
Uson, J. et al., "Soluble Interleukin 6 (IL-6) Receptor and IL-6 Levels in Serum and Synovial Fluid of Patients with Different Arthropathies," The Journal of Rheumatology, Nov. 1997, pp. 2069-2075, vol. 24, No. 11.
Vajdos, F.F. et al., "Comprehensive Functional Maps of the Antigen-Binding Site of an Anti-ErbB2 Antibody Obtained with Shotgun Scanning Mutagenesis," J. Mol. Biol. Jul. 5, 2002, pp. 415-428, vol. 320. No. 2.
Valencik, M.L. et al., "Codon Optimization Markedly Improves Doxycycline Regulated Gene Expression in the Mouse Heart," Transgenic Research, 2001, pp. 269-275, vol. 10.
Valipour, A. et al., "Circulating Vascular Endothelial Growth Factor and Systemic Inflammatory Markers in Patients with Stable and Exacerbated Chronic Obstructive Pulmonary Disease," Clinical Science, 2008, pp. 225-232, vol. 115, No. 7.
Van Rhee, et al., "Siltuximab, a Novel Anti-lnterleukin-6 Monoclonal Antibody, for Castleman's Disease," Journal of Clinical Oncolocy, Aug. 10, 2010, pp. 3701-3708, vol. 28, No. 23.
Varghese, J.N. et al., "Structure of the Extracellular Domains of the Human Interleukin-6 Receptor.alpha.-chain", PNAS, 2002, pp. 15959-15964, vol. 99, No. 25.
Wallenius, V. et al., "Interleukin-6-Deficient Mice Develop Mature-Onset Obesity", Nature Medicine, 2002, pp. 75-79, vol. 8, No. 1.
Walter, R.E. et al., "Systemic Inflammation and COPD," Chest, Jan. 2008, pp. 19-25. vol. 133, No. 1.
Wang, C-Y. et al., "The Role of TMPRSS6/Matriptase-2 in Iron Regulation and Anemia," Frontiers in Pharmacology, May 2014, pp. 1-6, vol. 5, Article 114.
Ward, E.S. et al., "Binding Activities of a Repertoire of Single Immunoglobulin Variable Domains Secreted from *Escherichia coli*," Nature, 1989, pp. 544-546, vol. 341.
Wendling, D. et al., "Treatment of Severe Rheumatoid Arthritis by Anti-Interleukin 6 Monoclonal Antibody", The Journal of Rheumatology, 1993,, pp. 259-262, vol. 20.
Wijdenes, J. et al., "Human Recombinant Dimeric IL-6 Binds to Its Receptor as Detected by Anti-IL-6 Monoclonal Antibodies", Molecular Immunology, 1991, pp. 1183-1192, vol. 28, No. 11.

(56) References Cited

OTHER PUBLICATIONS

Winkler, K. et al., "Changing the Antigen Binding Specificity by Single Point Mutations of an Anti-p24 (HIV-1) Antibody," The Journal of Immunology, Oct. 15, 2000, pp. 4505-4514, vol. 165, No. 8.

Won, H.S. et al., "IL-6 is an Independent Risk Factor for Resistance to Erythropoiesis-Stimulating Agents in Hemodialysis Patients Without Iron Deficiency," Hemodialysis International, Jan. 2012, pp. 31-37. vol. 16, No. 1.

Wu, H. et al., "Humanization of a Murine Monoclonal Antibody by Simultaneous Optimization of Framework and CDR Residues," J. Mol. Biol., Nov. 19, 1999, pp. 151-162, vol. 294, No. 1.

Xu, D. et al., "In Vitro Characterization of Five Humanized OKT3 Effector Function Variant Antibodies," Cellular Immunology, 2000, pp. 16-26, vol. 200.

Yanbaeva, D.G. et al., "IL6 and CRP Haplotypes are Associated with COPD Risk and Systemic Inflammation: A Case-Control Study," BMC Medical Genetics, 2009, 11 pages, vol. 10, No. 23.

Yeung, Y.A. et al., "Engineering human IgG1 affinity to human neonatal Fc receptor: impact of affinity improvement on pharmacokinetics in primates," Journal of Immunology, 2009, vol. 182, pp. 7663-7671.

Yokota, S. et al., "Therapeutic Efficacy of Humanized Recombinant Anti-Interleukin-6 Receptor Antibody in Children With Systemic-Onset Juvenile Idiopathic Arthritis", Arthritis & Rheumatism, 2005, pp. 818-825, vol. 52, No. 3.

Yoshida, K. et al., "Targeted disruption of gp130, a common signal transducer for the interleukin 6 family of cytokines, leads to myocardial and hematological disorders", Proc. Natl. Acad. Sci. USA, 1996, pp. 407-411, vol. 93.

Zaanen, van H.C.T. et al., "Chimaeric Anti-Interleukin 6 Monoclonal Antibodies in the Treatment of Advanced Multiple Myeloma: a Phase I Dose-Escalating Study", British Journal of Haematology, 1998, pp. 783-790, vol. 102.

Zaanen, van H.C.T. et al., "Endogenous Interleukin 6 Production in Multiple Myeloma Patients Treated with Chimeric Monoclonal Anti-IL-6 Antibodies Indicates the Existence of a Positive Feedback Loop", J. Clin. Invest., 1996, pp. 1441-1448, vol. 98, No. 6.

Zhang, W. et al., "Interleukin 6 Underlies Angiotensin II-Induced Hypertension and Chronic Renal Damage," Hypertension, Jan. 2012, pp. 136-144, vol. 59.

Bird Rock Bio, Inc., "Study Evaluating Gerilimzumab's Safety/Efficacy for Patients MTX or TNFα Antagonist Failed in Rheumatoid Arthritis," Jun. 10, 2016, 10 pages, [Online] [Retrieved on Nov. 25, 2019] Retrieved from the internet <URL: https://clinicaltrials.gov/ct2/show/NCT02795299>.

Casu, G. et al. "Diuretic Therapy in Heart Failure—Current Approaches." European Cardiology, vol. 10, No. 1, Jul. 2015, pp. 42-47.

Demant, A. W. et al. "Heart Failure and Malignant Ventricular Tachyarrhythmias due to Hereditary Hemochromatosis with Iron Overload Cardiomyopathy." Clinical Research in Cardiology, vol. 96, Aug. 20, 2007, pp. 900-903.

Ellison, D. H. "Chapter 30: The Physiological Basis of Diuretic Drug Action and Synergism." Principles of Medical Biology, vol. 8B: Molecular and Cellular Pharmacology, 1997, pp. 577-599.

Tsutamoto, T. et al. "Interleukin-6 Spillover in the Peripheral Circulation Increases with the Severity of Heart Failure, and the High Plasma Level of Interleukin-6 is an Important Prognostic Predictor in Patients with Congestive Heart Failure." Journal of the American College of Cardiology, vol. 31, No. 2, Feb. 1998, pp. 391-398.

United States Office Action, U.S. Appl. No. 16/482,038, dated Sep. 25, 2020, 14 pages.

Valenti, L. et al. "Effect of the A736V TMPRSS6 Polymorphism on the Penetrance and Clinical Expression of Hereditary Hemochromatosis." Journal of Hepatology, vol. 57, No. 6, Dec. 2012, pp. 1319-1325.

"Cardiorenal Syndrome Type 4." Heart, vol. 47, Iss. 5, May 2015, pp. 551-555, (with concise explanation of relevance).

Abeywardena, M.Y. et al., "Cardiovascular Biology of Interleukin-6," Current Pharmaceutical Design, 2009, vol. 15, pp. 1809-1821.

Chambers, J. C. et al. "Genome-Wide Association Study Identifies Variants in TMPRSS6 Associated with Hemoglobin Levels." Supplementary Online Material, Nature Genetics, [undated], pp. 1-12.

Corvidia Therapeutics, "Study to Assess the Safety, Pharmacokinetics, and Pharmacodynamics of Multiple Doses of COR-001," Aug. 16, 2016, 6 pages, [Online] [Retrieved on Jan. 29, 2020] Retrieved from the internet <URL: https://clinicaltrials.gov/ct2/show/NCT02868229>.

Deisseroth, A. et al. "FDA Approval: Siltuximab for the Treatment of Patients with Multicentric Castleman Disease." Clinical Cancer Research, vol. 21, Iss. 5, Mar. 1, 2015, pp. 950-954.

Hanberg, J. S. et al. "Inflammation and Cardio-Renal Interactions in Heart Failure: A Potential Role for Interleukin-6." European Journal of Heart Failure, vol. 20, Iss. 5, May 2018, pp. 933-934.

Massie, B. M. et al. "Rolofylline, an Adenosine A1-Receptor Antagonist, in Acute Heart Failure." The New England Journal of Medicine, vol. 363, Oct. 7, 2010, pp. 1419-1428.

Muller, J. et al. "Interleukin-6-Dependent Phenotypic Modulation of Cardiac Fibroblasts after Acute Myocardial Infarction." Abstract, Basic Research in Cardiology, vol. 109, Iss. 6, Nov. 2014, pp. 1.

Nowak, K. L. et al. "A Phase 1 Randomized, Double-Blind, Placebo-Controlled, Cohort Dose-Escalation Study of a Human Monoclonal Antibody to IL-6 in Patients with Chronic Kidney Disease." Kidney Week 2019, Washington, DC, Nov. 5-10, 2019, 1 page.

O'connor, C. M. et al. "The PROTECT In-Hospital Risk Model: 7-Day Outcome in Patients Hospitalized with Acute Heart Failure and Renal Dysfunction." European Journal of Heart Medicine, vol. 14, 2012, pp. 605-612.

Palin, K. et al. "Age-Impaired Fluid Homeostasis Depends on the Balance of IL-6/IGF-I in the Rat Supraoptic Nuclei." Neurobiology of Aging, vol. 30, Iss. 10, Oct. 2009, pp. 1677-1692.

PCT International Search Report and Written Opinion, PCT Application No. PCT/US16/044528, dated Oct. 14, 2016, 15 pages.

PCT International Search Report and Written Opinion, PCT Application No. PCT/US2018/016508, dated Apr. 24, 2018, 8 pages.

Poli, M. et al. "Hepcidin Antagonists for Potential Treatments of Disorders with Hepcidin Excess." Frontiers in Pharmacology, vol. 5, Iss. 86, Apr. 28, 2014, pp. 1-13.

Ridker, P.M. et al., "Antiinflammatory Therapy with Canakinumab for Atherosclerotic Disease," The New England Journal of Medicine, Sep. 21, 2017, vol. 377, No. 12, pp. 1119-1131.

Rossi, J-F. et al. "Interleukin-6 as a Therapeutic Target." Clinical Cancer Research, vol. 21, Iss. 6, Mar. 15, 2015, pp. 1248-1257.

Ter Maaten, J.M. et al., "A combined clinical and biomarker approach to predict diuretic response in acute heart failure," Clin Res Cardiol, 2016, vol. 105, pp. 145-153.

The Japan Patent Office, Office Action, Japanese Patent Application No. 2018-525517, dated Jul. 7, 2020, eight pages.

United States Office Action, U.S. Appl. No. 15/222,507, dated Aug. 8, 2019, 11 pages.

United States Office Action, U.S. Appl. No. 15/222,507, dated Mar. 30, 2018, 13 pages.

United States Office Action, U.S. Appl. No. 15/222,507, dated Nov. 8, 2018, 11 pages.

United States Office Action, U.S. Appl. No. 16/396,378, dated Sep. 20, 2019, 17 pages.

United States Patent and Trademark Office, Restriction Requirement, U.S. Appl. No. 16/482,038, dated Jun. 8, 2020, eight pages.

Voors, A. A. et al. "A Systems BIOlogy Study to TAilored Treatment in Chronic Heart Failure: Rationale, Design, and Baseline Characteristics of BIOSTAT-CHF." European Journal of Heart Failure, vol. 18, 2016, pp. 716-726.

Voors, A. A. et al. "Development and Validation of Multivariable Models to Predict Mortality and Hospitalization in Patients with Heart Failure." vol. 19, Iss. 5, May 2017, pp. 627-634.

Weatherly, B. D. et al. "Design and Rationale of the PROTECT Study: A Placebo-controlled Randomized Study of the Selective A1 Adenosine Receptor Antagonist Rolofylline for Patients Hospitalized With Acute Decompensated Heart Failure and Volume Over-

(56) References Cited

OTHER PUBLICATIONS load to Assess Treatment Effect on Congestion and Renal Function." Journal of Cardiac Failure, vol. 16, Iss. 1, Jan. 2010, pp. 25-35.
Weinstein, D. A. et al. "Inappropriate Expression of Hepcidin is Associated with Iron Refractory Anemia Implications for the Anemia of Chronic Disease." Blood, vol. 100, Iss. 10, Nov. 15, 2002, pp. 3776-3781.
Aday, A. W. et al. "Targeting Residual Inflammatory Risk: A Shifting Paradigm for Atherosclerotic Disease." Frontiers in Cardiovascular Medicine, vol. 6, Article 16, Feb. 2019, pp. 1-12.
Barreto, D. V. et al. "Plasma Interleukin-6 is Independently Associated with Mortality in Both Hemodialysis and Pre-Dialysis Patients with Chronic Kidney Disease." Kidney International, vol. 77, Iss. 6, Mar. 2, 2010, pp. 550-556.
Everett, B. M. et al. "Anti-Inflammatory Therapy with Canakinumab for the Prevention of Hospitalization for Heart Failure." Circulation, vol. 139, Iss. 10, Mar. 5, 2019, pp. 1289-1299.
Hanberg, J. S. et al. Supplementary Material. "Inflammation and Cardio-Renal Interactions in Heart Failure: A Potential Role for Interleukin-6." European Journal of Heart Failure, vol. 20, Iss. 5, May 2018, pp. 1-4.
Held, C. et al. "Inflammatory Biomarkers Interleukin-6 and C-Reactive Protein and Outcomes in Stable Coronary Heart Disease: Experiences from the STABILITY (Stabilization of Atherosclerotic Plaque by Initiation of Darapladib Therapy) Trial." Journal of the American Heart Association, vol. 6, Iss. 10, Oct. 11, 2017, pp. 1-35.
Kakkar, R. et al. "Effects of Ziltivekimab (ZILTI), a Novel Anti-Interleukin-6 Monoclonal Antibody, on Markers of Inflammation and Cardiovascular Risk in Patients With Chronic Kidney Disease on Hemodialysis." Circulation, vol. 140, Nov. 19, 2019.
Lindmark, E. et al. "Relationship Between Interleukin 6 and Mortality in Patients with Unstable Coronary Artery Disease: Effects of an Early Invasive or Noninvasive Strategy." JAMA, vol. 286, Iss. 17, Nov. 7, 2001, pp. 2107-2113.
Markousis-Mavrogenis, G. et al. "The Clinical Significance of Interleukin-6 in Heart Failure: Results from the BIOSTAT-CHF Study." European Journal of Heart Failure, vol. 21, Iss. 8, Aug. 2019, pp. 965-973.
Plenz, G. et al. "Activation of the Cardiac Interleukin-6 System in Advanced Heart Failure." European Journal of Medicine, vol. 3, Iss. 4, Aug. 2001, pp. 415-421.
Ridker, P. M. et al. "C-Reactive Protein and Other Markers of Inflammation in the Prediction of Cardiovascular Disease in Women." The New England Journal of Medicine, vol. 342, Iss. 12, Mar. 23, 2000, pp. 836-843.
Ridker, P. M. et al. "Inhibition of Interleukin-1β by Canakinumab and Cardiovascular Outcomes in Patients With Chronic Kidney Disease." Journal of the American College of Cardiology, vol. 71, Iss. 21, May 29, 2018, pp. 2405-2414.
Ridker, P. M. et al. "Modulation of the Interleukin-6 Signalling Pathway and Incidence Rates of Atherosclerotic Events and All-Cause Mortality: Analyses from the Canakinumab Anti-Inflammatory Thrombosis Outcomes Study (CANTOS)." European Heart Journal, vol. 39, Iss. 38, Oct. 7, 2018, pp. 3499-3507.
Ridker, P. M. et al. "Plasma Concentration of Interleukin-6 and the Risk of Future Myocardial Infarction Among Apparently Healthy Men." Circulation, vol. 101, Iss. 15, Apr. 18, 2000, pp. 1767-1772.
Rothaug, M. et al. "The Role of Interleukin-6 Signaling in Nervous Tissue." Biochimica et Biophysica Acta, vol. 1863, Iss. 6, Part A, Jun. 2016, pp. 1218-1227.
Su, H. et al. "Interleukin-6 Signaling Pathway and its Role in Kidney Disease: An Update." Frontiers in Immunology, vol. 8, Article 405, Apr. 2017, pp. 1-10.
United States Office Action, U.S. Appl. No. 15/222,507, dated Dec. 10, 2020, 12 pages.
United States Office Action, U.S. Appl. No. 16/482,038, dated Mar. 16, 2021, 22 pages.
Winthrop, K. L. et al. "Opportunistic Infections and Biologic Therapies in Immune-Mediated Inflammatory Diseases: Consensus Recommendations for Infection Reporting During Clinical Trials and Postmarketing Surveillance." Annals of the Rheumatic Diseases, vol. 74, Iss. 12, Sep. 22, 2015, pp. 2107-2116.
Yeun, J. Y. et al. "C-Reactive Protein Predicts All-Cause and Cardiovascular Mortality in Hemodialysis Patients." American Journal of Kidney Diseases, vol. 35, Iss. 3, Mar. 2000, pp. 469-476.
Zhang, J. et al. "Anti-IL-6 Neutralizing Antibody Modulates Blood-Brain Barrier Function in the Ovine Fetus." The FASEB Journal, vol. 29, Iss. 5, May 2015, pp. 1739-1753.
Kanda, J. et al. "Reversible Cardiomyopathy Associated with Multicentric Castleman Disease: Successful Treatment with Tocilizumab, an Anti-Interleukin 6 Receptor Antibody." International Journal of Hematology, vol. 85, No. 3, Apr. 2007, pp. 207-211.
United States Office Action, U.S. Appl. No. 16/482,038, dated Jul. 8, 2021, 14 pages.
Yan, A. T. et al. "Relationship of Interleukin-6 with Regional and Global Left-Ventricular Function in Asymptomatic Individuals without Clinical Cardiovascular Disease: Insights from the Multi-Ethnic Study of Atherosclerosis." European Heart Journal, vol. 31, No. 7, Apr. 2010, pp. 875-882.
Anonymous. "History of Changes for Study: NCT03926117: A Phase 2, Randomized, Double-Blind, Placebo-Controlled Trial to Evaluate Reduction in Inflammation in Patients with Advanced Chronic Renal Disease Utilizing Antibody Mediated IL-6 Inhibition (RESCUE)." ClinicalTrials.gov, Archive, Apr. 19, 2019, 4 pages, [Online] [Retrieved Sep. 15, 2021], Retrieved from the Internet <URL:https://clinicaltrials.gov/ct2/history/NCT03926117?V_1=View#StudyPageTop>.
Anonymous. "History of Changes for Study: NCT04626505: Trial to Evaluate Reduction in Inflammation in Patients with Advanced Chronic Renal Disease Utilizing Antibody Mediated IL-6 Inhibition in Japan (RESCUE-2)." ClinicalTrials.gov, Archive, Nov. 10, 2020, 5 pages, [Online] [Retrieved Sep. 15, 2021], Retrieved from the Internet <URL:https://clinicaltrials.gov/ct2/history/NCT04626505?V_1=View#StudyPageTop>.
Bonda, T. A. et al. "CCN1 Expression in Interleukin-6 Deficient Mouse Kidney in Experimental Model of Heart Failure." Folia Histochemica et Cytobiologica, vol. 51, No. 1, 2013, pp. 84-91.
Elewa, U. et al. "Cardiovascular Risk Biomarkers in CKD: The Inflammation Link and the Road Less Traveled." International Urology and Nephrology, vol. 44, Sep. 11, 2012, pp. 1731-1744.
Fontes, J. A. et al. "The Varying Faces of IL-6: From Cardiac Protection to Cardiac Failure." Cytokine, vol. 74, No. 1, Jul. 2015, pp. 62-68.
Harrison, S. C. et al. "Interleukin-6 Receptor Pathways in Abdominal Aortic Aneurysm." European Heart Journal, vol. 34, No. 48, Dec. 21, 2013, pp. 3707-3716.
Kaminska, J. et al. "IL 6 but not TNF is Linked to Coronary Artery Calcification in Patients with Chronic Kidney Disease." Cytokine, vol. 120, Aug. 2019, pp. 9-14.
Panichi, V. et al. "C Reactive Protein in Patients with Chronic Renal Diseases." Renal Failure, vol. 23, No. 3-4, May 1, 2001, pp. 551-562.
Pergola, P. et al. "Ziltivekimab for Treatment of Anemia of Inflammation in Patients on Hemodialysis: Results from a Phase 1/2 Multicenter, Randomized, Double-Blind, Placebo-Controlled Trial." Journal of the American Society of Nephrology, vol. 32, No. 1, Jan. 29, 2021, pp. 211-222.
Ridker, P. M. et al. "Anti-Inflammatory Therapies for Cardiovascular Disease." European Heart Journal, vol. 35, 2014, pp. 1782-1791.
Swerdlow, D. et al. "The Interleukin-6 Receptor as a Target for Prevention of Coronary Heart Disease: A Mendelian Randomisation Analysis." The Lancet, vol. 379, No. 9822, Mar. 31, 2012, pp. 1214-1224.
Tanaka, T. et al. "Targeting Interleukin-6: All the Way to Treat Autoimmune and Inflammatory Diseases." International Journal of Biological Sciences, vol. 8, No. 9, Oct. 24, 2012, pp. 1227-1236.
Tanaka, T. et al. "Interleukin-6 Inhibition in Inflammatory Diseases: Results Achieved and Tasks to Accomplish." Journal of Scleroderma and Related Disorders, vol. 2, No. 2, Aug. 12, 2017, pp. S20-S28.
Van Rhee, F. et al. "A Phase 2, Open-Label, Multicenter Study of the Long-Term Safety of Siltuximab (an Anti-Interleukin-6 Monoclonal

(56) References Cited

OTHER PUBLICATIONS

Antibody) in Patients with Multicentric Castleman Disease." Oncotarget, vol. 6, No. 30, Oct. 6, 2015, pp. 30408-30419.

Verma, S. et al. "Endothelin Antagonism and Interleukin-6 Inhibition Attenuate the Proatherogenic Effects of C-Reactive Protein." Circulation, vol. 105, No. 16, Apr. 23, 2002, pp. 1890-1896.

Kobara et al., "Antibody against interleukin-6 receptor attenuates left ventricular remodelling after myocardial infarction in mice", Cardiovascular Research, Mar. 7, 2010, vol. 87, pp. 424-430.

Galesloot et al., "Iron and hepcidin as risk factors in atherosclerosis: what do the genes say?", BMC Genetics, Jul. 2015, vol. 16, pp. 1-12.

Astrazeneca. "A Double-Blind Placebo-Controlled, Randomized Study in Arthritis Subjects to Evaluate the Safety, Tolerability, Pharmacokinetics, and Pharmacodynamics of Single Ascending Doses of MEDI5117 (anti0IL-6)." ClinicalTrials.gov, Study NCT01559103, Feb. 19, 2015, pp. 1-12.

Davis, C. C. et al. "Clinical Development of Siltuximab." Current Oncology Reports, vol. 17, Issue 29, Jul. 2015, pp. 1-9.

De Falco, L. et al. "Iron Refractory Iron Deficiency Anemia." Haematologica, vol. 98, No. 6, Jun. 2013, pp. 845-853.

Keskin, E. Y. et al. "Iron-Refractory Iron Deficiency Anemia." Turkish Journal of Hematology, vol. 32, No. 1, Mar. 2015, pp. 1-14.

Lee, P. "Role of Matriptase-2 (TMPRSS6) in Iron Metabolism." Acta Haematologica, vol. 122, No. 2-3, Nov. 10, 2009, pp. 87-96.

Pelusi, S. et al. "The A736V TMPRSS6 Polymorphism Influences Hepcidin and Iron Metabolism in Chronic Hemodialysis Patients: TMPRSS6 and Hepcidin in Hemodialysis." BMC Nephrology, vol. 14, Feb. 22, 2013, pp. 1-9.

Raj, D. S. C. "Role of Interleukin-6 in the Anemia of Chronic Disease." Seminars in Arthritis and Rheumatism, vol. 38, No. 5, Apr. 2009, pp. 382-388.

Rossi, J.-F. et al. "A Phase I/II Study of Siltuximab (CNTO 328), an Anti-Interleukin-6 Monoclonal Antibody, in Metastatic Renal Cell Cancer." British Journal of Cancer, vol. 103, Aug. 31, 2010, pp. 1154-1162.

Schipperus, M. et al. "CNT0328 (Anti-IL-6 mAb) Treatment is Associated with an Increase in Hemoglobin (Hb) and Decrease in Hepcidin Levels in Renal Cell Carcinoma (RCC)." Blood, vol. 114, No. 22, Nov. 20, 2009, pp. 1-3.

Snpedia. "Rs855791" Last Modified Jun. 28, 2015, 5 pages, [Online] [Retrieved on Sep. 15, 2015] Retrieved from the Internet<URL:http://www.snpedia.com/index.php/Rs855791 >.

Van Rhee et al., "Siltuximab for multicentric Castleman's disease: a randomised, double-blind, placebo-controlled trial," The Lancet Oncology, Aug. 2014, vol. 15, No. 9, pp. 966-974.

Yasukawa, H. et al. "As a Progressive Factor for Heart Failure: Inflammatory Fluid Factor Myocardial Damage." Japanese Journal of Medicine and Pharmaceutical Science, 2006, vol. 55, No. 6, pp. 821-825, (with concise explanation of relevance).

Keidar et al., "Angiotensin II Administration to Atherosclerotic Mice Increases Macrophage Uptake of Oxidized LDL, A Possible Role for Interleukin-6", Arterioscler Thromb Vasc Biol., Sep. 2001, vol. 21, pp. 1464-1469.

Barquero, "Siltuximab: a new option for the management of Castleman's disease", Drugs Today (Barc), Jan. 2015, vol. 51, No. 1, pp. 21-28.

Liu et al., "Siltuximab for multicentric Castleman disease", Expert Rev Hematol., Oct. 2014, vol. 7, No. 5, pp. 545-557.

\* cited by examiner

METHODS FOR TREATING IL-6 MEDIATED INFLAMMATION WITHOUT IMMUNOSUPPRESSION

CROSS REFERENCE TO RELATED APPLICATIONS

This application is a continuation of co-pending U.S. application Ser. No. 16/240,670, filed Jan. 4, 2019, which claims priority to U.S. Provisional Application No. 62/614,134, filed Jan. 5, 2018, each of which is hereby incorporated in its entirety by reference.

SEQUENCE LISTING

The instant application contains a Sequence Listing which has been submitted via EFS-Web and is hereby incorporated by reference in its entirety. Said ASCII copy, created on Apr. 19, 2019, is named 43398US_sequencelisting.txt, and is 26,493, bytes in size.

BACKGROUND

Chronic inflammation is a characteristic of many diseases, including both the classical rheumatic disorders such as rheumatoid arthritis, juvenile idiopathic arthritis, psoriatic arthritis, and inflammatory bowel disease, as well as other systemic diseases that are increasingly understood to be associated with chronic inflammation, such as cardiovascular disease, renal disease, neuroinflammatory diseases, anemias, cancer and aging.

The pro-inflammatory cytokine, IL-6, often plays a critical role in chronic inflammation through activation of the JAK-STAT signaling pathway, and IL-6 inhibitors have been developed to treat certain inflammatory disorders in which IL-6 has been shown to contribute significantly to disease etiology. The anti-IL-6 receptor antibody, tocilizumab (ACTEMRA), has been approved for treatment of rheumatoid arthritis, giant cell arteritis, polyarticular juvenile idiopathic arthritis, systemic juvenile idiopathic arthritis, and iatrogenic cytokine release syndrome. The anti-IL-6 receptor antibody, sarilumab (KEVZARA), has been approved to treat adult patients with moderately to severely active rheumatoid arthritis.

Although inhibition of IL-6 can be effective, treatment of chronic inflammation with IL-6 inhibitors using current dose regimens often leads to immune suppression. Immunosuppression can result in increased susceptibility to pathogens such as bacteria, fungi, and viruses. The FDA-approved product label for ACTEMRA warns of the risk of serious infections leading to hospitalization or death, including tuberculosis, bacterial, invasive fungal, viral, and other opportunistic infection; the KEVZARA label warns of serious infections leading to hospitalization or death including bacterial, viral, invasive fungal, and other opportunistic infections.

There is, therefore, a need for new methods for treating IL-6 mediated inflammation that do not lead to immune suppression.

SUMMARY

We have demonstrated that IL-6 antagonists can be administered at a dose, on a schedule, and for a period sufficient to reduce inflammation without causing immune suppression.

Accordingly, in a first aspect, methods for treating IL-6-mediated inflammation in a patient are provided. The methods comprise: administering an IL-6 antagonist to a patient with IL-6-mediated inflammation at a dose that is sufficient to reduce inflammation without causing immune suppression.

In some embodiments, the patient has an elevated pre-treatment C-reactive protein (CRP) level. In some embodiments, the pre-treatment CRP level of the patient is at least 2 mg/L. In some embodiments, the pre-treatment CRP level of the patient is at least 4 mg/L. In some embodiments, the pre-treatment CRP level of the patient is at least 6 mg/L. In some embodiments, the pre-treatment CRP level of the patient is at least 10 mg/L.

In some embodiments, the patient has an elevated pre-treatment serum IL-6 level. In some embodiments, the pre-treatment serum IL-6 level of the patient is at least 4 pg/mL. In some embodiments, the pre-treatment serum IL-6 level of the patient is at least 4 pg/mL. In some embodiments, the pre-treatment serum IL-6 level of the patient is at least 5 pg/mL. In some embodiments, the pre-treatment serum IL-6 level of the patient is at least 10 pg/mL.

In some embodiments, the inflammation is measured by the level of C-reactive protein (CRP). In some embodiments, the post-treatment CRP level is no more than 2 mg/L. In some embodiments, the post-treatment CRP level is no more than 1 mg/L. In some embodiments, the CRP level is decreased by at least 50% as compared to pre-treatment levels. In some embodiments, the CRP level is decreased by at least 70% as compared to pre-treatment levels. In some embodiments, the CRP level is decreased by at least 80% as compared to pre-treatment levels. In some embodiments, the CRP level is decreased by at least 90% as compared to pre-treatment levels.

In some embodiments, the immune suppression is measured by absolute neutrophil count (ANC). In some embodiments, the post-treatment ANC is at least 500 cells/µL. In some embodiments, the post-treatment ANC is at least 1000 cells/µL. In some embodiments, the post-treatment ANC is at least 1500 cells/µL. In some embodiments, the post-treatment ANC is at least 2000 cells/µL. In some embodiments, the ANC is decreased by no more than 2000 cells/µL as compared to pre-treatment levels. In some embodiments, the ANC is decreased by no more than 1500 cells/µL as compared to pre-treatment levels. In some embodiments, the ANC is decreased by no more than 1000 cells/µL as compared to pre-treatment levels. In some embodiments, the ANC is decreased by no more than 500 cells/µL as compared to pre-treatment levels. In some embodiments, the ANC is decreased by no more than 50% as compared to pre-treatment levels. In some embodiments, the ANC is decreased by no more than 40% as compared to pre-treatment levels. In some embodiments, the ANC is decreased by no more than 30% as compared to pre-treatment levels. In some embodiments, the ANC is decreased by no more than 20% as compared to pre-treatment levels. In some embodiments, the ANC is decreased by no more than 10% as compared to pre-treatment levels. In some embodiments, the ANC is not decreased as compared to pre-treatment levels.

In some embodiments, the IL-6 antagonist is administered at a monthly equivalent dose that is no more than 30% of the monthly equivalent dose for treating rheumatoid arthritis with the same IL-6 antagonist. In some embodiments, the IL-6 antagonist is administered at a monthly equivalent dose that is no more than 20% of the monthly equivalent dose for treating rheumatoid arthritis with the same IL-6 antagonist.

In some embodiments, the IL-6 antagonist is administered at a monthly equivalent dose that is no more than 10% of the monthly equivalent dose for treating rheumatoid arthritis with the same IL-6 antagonist. In some embodiments, the IL-6 antagonist is administered at a monthly equivalent dose that is about 25% of a monthly equivalent dose for treating rheumatoid arthritis with the same IL-6 antagonist. In some embodiments, the IL-6 antagonist is administered at a monthly equivalent dose that is about 20% of a monthly equivalent dose for treating rheumatoid arthritis with the same IL-6 antagonist. In some embodiments, the IL-6 antagonist is administered at a monthly equivalent dose that is about 15% of a monthly equivalent dose for treating rheumatoid arthritis with the same IL-6 antagonist. In some embodiments, the IL-6 antagonist is administered at a monthly equivalent dose that is about 10% of a monthly equivalent dose for treating rheumatoid arthritis with the same IL-6 antagonist. In some embodiments, the IL-6 antagonist is administered at a monthly equivalent dose that is about 5% of a monthly equivalent dose for treating rheumatoid arthritis with the same IL-6 antagonist.

In some embodiments, the IL-6 antagonist is an anti-IL-6 antibody.

In some embodiments, the anti-IL-6 antibody is COR-001. In some embodiments, COR-001 is administered intravenously at a monthly equivalent dose of 2-40 mg. In some embodiments, COR-001 is administered intravenously at a monthly equivalent dose of about 2 mg. In some embodiments, COR-001 is administered intravenously at a monthly equivalent dose of about 4 mg. In some embodiments, COR-001 is administered intravenously at a monthly equivalent dose of about 6 mg. In some embodiments, COR-001 is administered intravenously at a monthly equivalent dose of about 10 mg. In some embodiments, COR-001 is administered intravenously at a monthly equivalent dose of about 20 mg. In some embodiments, COR-001 is administered intravenously at a monthly equivalent dose of about 40 mg. In some embodiments, COR-001 is administered subcutaneously at a monthly equivalent dose of 3-70 mg. In some embodiments, COR-001 is administered subcutaneously at a monthly equivalent dose of about 3 mg. In some embodiments, COR-001 is administered subcutaneously at a monthly equivalent dose of about 7 mg. In some embodiments, COR-001 is administered subcutaneously at a monthly equivalent dose of about 10 mg. In some embodiments, COR-001 is administered subcutaneously at a monthly equivalent dose of about 17 mg. In some embodiments, COR-001 is administered subcutaneously at a monthly equivalent dose of about 35 mg. In some embodiments, COR-001 is administered subcutaneously at a monthly equivalent dose of about 70 mg.

In some embodiments, the anti-IL-6 antibody is siltuximab. In some embodiments, siltuximab is administered intravenously at a monthly equivalent dose of 50-500 mg. In some embodiments, siltuximab is administered intravenously at a monthly equivalent dose of about 50 mg. In some embodiments, siltuximab is administered intravenously at a monthly equivalent dose of about 100 mg. In some embodiments, siltuximab is administered intravenously at a monthly equivalent dose of about 150 mg. In some embodiments, siltuximab is administered intravenously at a monthly equivalent dose of about 200 mg. In some embodiments, siltuximab is administered intravenously at a monthly equivalent dose of about 300 mg. In some embodiments, siltuximab is administered intravenously at a monthly equivalent dose of about 500 mg. In some embodiments, siltuximab is administered subcutaneously at a monthly equivalent dose of 80-800 mg. In some embodiments, siltuximab is administered subcutaneously at a monthly equivalent dose of about 80 mg. In some embodiments, siltuximab is administered subcutaneously at a monthly equivalent dose of about 160 mg. In some embodiments, siltuximab is administered subcutaneously at a monthly equivalent dose of about 240 mg. In some embodiments, siltuximab is administered subcutaneously at a monthly equivalent dose of about 320 mg. In some embodiments, siltuximab is administered subcutaneously at a monthly equivalent dose of about 480 mg. In some embodiments, siltuximab is administered subcutaneously at a monthly equivalent dose of about 800 mg.

In some embodiments, the anti-IL-6 antibody is gerilimzumab. In some embodiments, gerilimzumab is administered intravenously at a monthly equivalent dose of 0.075-1.8 mg. In some embodiments, gerilimzumab is administered intravenously at a monthly equivalent dose of about 0.075 mg. In some embodiments, gerilimzumab is administered intravenously at a monthly equivalent dose of about 0.12 mg. In some embodiments, gerilimzumab is administered intravenously at a monthly equivalent dose of about 0.3 mg. In some embodiments, gerilimzumab is administered intravenously at a monthly equivalent dose of about 0.6 mg. In some embodiments, gerilimzumab is administered intravenously at a monthly equivalent dose of about 0.9 mg. In some embodiments, gerilimzumab is administered intravenously at a monthly equivalent dose of about 1.8 mg. In some embodiments, gerilimzumab is administered subcutaneously at a monthly equivalent dose of 0.125-3 mg. In some embodiments, gerilimzumab is administered subcutaneously at a monthly equivalent dose of about 0.125 mg. In some embodiments, gerilimzumab is administered subcutaneously at a monthly equivalent dose of about 0.2 mg. In some embodiments, gerilimzumab is administered subcutaneously at a monthly equivalent dose of about 0.5 mg. In some embodiments, gerilimzumab is administered subcutaneously at a monthly equivalent dose of about 1 mg. In some embodiments, gerilimzumab is administered subcutaneously at a monthly equivalent dose of about 1.5 mg. In some embodiments, gerilimzumab is administered subcutaneously at a monthly equivalent dose of about 3 mg.

In some embodiments, the anti-IL-6 antibody is sirukumab. In some embodiments, sirukumab is administered intravenously at a monthly equivalent dose of 1.5-60 mg. In some embodiments, sirukumab is administered intravenously at a monthly equivalent dose of about 1.5 mg. In some embodiments, sirukumab is administered intravenously at a monthly equivalent dose of about 3 mg. In some embodiments, sirukumab is administered intravenously at a monthly equivalent dose of about 6 mg. In some embodiments, sirukumab is administered intravenously at a monthly equivalent dose of about 12 mg. In some embodiments, sirukumab is administered intravenously at a monthly equivalent dose of about 36 mg. In some embodiments, sirukumab is administered intravenously at a monthly equivalent dose of about 60 mg. In some embodiments, sirukumab is administered subcutaneously at a monthly equivalent dose of 2.5-100 mg. In some embodiments, sirukumab is administered subcutaneously at a monthly equivalent dose of about 2.5 mg. In some embodiments, sirukumab is administered subcutaneously at a monthly equivalent dose of about 5 mg. In some embodiments, sirukumab is administered subcutaneously at a monthly equivalent dose of about 10 mg. In some embodiments, sirukumab is administered subcutaneously at a monthly equivalent dose of about 20 mg. In some embodiments, sirukumab is administered subcutaneously at a monthly equivalent dose of about 60 mg. In some embodiments, sirukumab is administered subcutaneously at a monthly equivalent dose of about 100 mg.

In some embodiments, the anti-IL-6 antibody is clazakizumab. In some embodiments, clazakizumab is administered intravenously at a monthly equivalent dose of 3-60 mg. In some embodiments, clazakizumab is administered intravenously at a monthly equivalent dose of about 3 mg. In some embodiments, clazakizumab is administered intravenously at a monthly equivalent dose of about 6 mg. In some embodiments, clazakizumab is administered intravenously at a monthly equivalent dose of about 12 mg. In some embodiments, clazakizumab is administered intravenously at a monthly equivalent dose of about 24 mg. In some embodiments, clazakizumab is administered intravenously at a monthly equivalent dose of about 36 mg. In some embodiments, clazakizumab is administered intravenously at a monthly equivalent dose of about 60 mg. In some embodiments, clazakizumab is administered subcutaneously at a monthly equivalent dose of 5-100 mg. In some embodiments, clazakizumab is administered subcutaneously at a monthly equivalent dose of about 5 mg. In some embodiments, clazakizumab is administered subcutaneously at a monthly equivalent dose of about 10 mg. In some embodiments, clazakizumab is administered subcutaneously at a monthly equivalent dose of about 20 mg. In some embodiments, clazakizumab is administered subcutaneously at a monthly equivalent dose of about 40 mg. In some embodiments, clazakizumab is administered subcutaneously at a monthly equivalent dose of about 60 mg. In some embodiments, clazakizumab is administered subcutaneously at a monthly equivalent dose of about 100 mg.

In some embodiments, the anti-IL-6 antibody is olokizumab. In some embodiments, olokizumab is administered intravenously at a monthly equivalent dose of 1.8-60 mg. In some embodiments, olokizumab is administered intravenously at a monthly equivalent dose of about 1.8 mg. In some embodiments, olokizumab is administered intravenously at a monthly equivalent dose of about 3.6 mg. In some embodiments, olokizumab is administered intravenously at a monthly equivalent dose of about 9 mg. In some embodiments, olokizumab is administered intravenously at a monthly equivalent dose of about 18 mg. In some embodiments, olokizumab is administered intravenously at a monthly equivalent dose of about 45 mg. In some embodiments, olokizumab is administered intravenously at a monthly equivalent dose of about 60 mg. In some embodiments, olokizumab is administered subcutaneously at a monthly equivalent dose of 3-100 mg. In some embodiments, olokizumab is administered subcutaneously at a monthly equivalent dose of about 3 mg. In some embodiments, olokizumab is administered subcutaneously at a monthly equivalent dose of about 6 mg. In some embodiments, olokizumab is administered subcutaneously at a monthly equivalent dose of about 15 mg. In some embodiments, olokizumab is administered subcutaneously at a monthly equivalent dose of about 30 mg. In some embodiments, olokizumab is administered subcutaneously at a monthly equivalent dose of about 72 mg. In some embodiments, olokizumab is administered subcutaneously at a monthly equivalent dose of about 100 mg.

In some embodiments, the anti-IL-6 antibody is VX30 (VOP-R003; Vaccinex). In some embodiments, VX30 (VOP-R003; Vaccinex) is administered intravenously. In some embodiments, VX30 (VOP-R003; Vaccinex) is administered subcutaneously.

In some embodiments, the anti-IL-6 antibody is EB-007 (EBI-029; Eleven Bio). In some embodiments, EB-007 (EBI-029; Eleven Bio) is administered intravenously. In some embodiments, EB-007 (EBI-029; Eleven Bio) is administered subcutaneously.

In some embodiments, the anti-IL-6 antibody is FM101 (Femta Pharmaceuticals, Lonza). In some embodiments, FM101 (Femta Pharmaceuticals, Lonza) is administered intravenously. In some embodiments, FM101 (Femta Pharmaceuticals, Lonza) is administered subcutaneously.

In some embodiments, the IL-6 antagonist is an anti-IL-6R antibody.

In some embodiments, the anti-IL-6R antibody is tocilizumab. In some embodiments, tocilizumab is administered intravenously at a monthly equivalent dose of 50-500 mg. In some embodiments, tocilizumab is administered intravenously at a monthly equivalent dose of about 50 mg. In some embodiments, tocilizumab is administered intravenously at a monthly equivalent dose of about 100 mg. In some embodiments, tocilizumab is administered intravenously at a monthly equivalent dose of about 150 mg. In some embodiments, tocilizumab is administered intravenously at a monthly equivalent dose of about 250 mg. In some embodiments, tocilizumab is administered intravenously at a monthly equivalent dose of about 350 mg. In some embodiments, tocilizumab is administered intravenously at a monthly equivalent dose of about 500 mg. In some embodiments, tocilizumab is administered subcutaneously at a monthly equivalent dose of 80-800 mg. In some embodiments, tocilizumab is administered subcutaneously at a monthly equivalent dose of about 80 mg. In some embodiments, tocilizumab is administered subcutaneously at a monthly equivalent dose of about 160 mg. In some embodiments, tocilizumab is administered subcutaneously at a monthly equivalent dose of about 240 mg. In some embodiments, tocilizumab is administered subcutaneously at a monthly equivalent dose of about 400 mg. In some embodiments, tocilizumab is administered subcutaneously at a monthly equivalent dose of about 560 mg. In some embodiments, tocilizumab is administered subcutaneously at a monthly equivalent dose of about 800 mg.

In some embodiments, the anti-IL-6R antibody is sarilumab. In some embodiments, sarilumab is administered intravenously at a monthly equivalent dose of 12-120 mg. In some embodiments, sarilumab is administered intravenously at a monthly equivalent dose of about 12 mg. In some embodiments, sarilumab is administered intravenously at a monthly equivalent dose of about 24 mg. In some embodiments, sarilumab is administered intravenously at a monthly equivalent dose of about 48 mg. In some embodiments, sarilumab is administered intravenously at a monthly equivalent dose of about 60 mg. In some embodiments, sarilumab is administered intravenously at a monthly equivalent dose of about 72 mg. In some embodiments, sarilumab is administered intravenously at a monthly equivalent dose of about 120 mg. In some embodiments, sarilumab is administered subcutaneously at a monthly equivalent dose of 20-200 mg. In some embodiments, sarilumab is administered subcutaneously at a monthly equivalent dose of about 20 mg. In some embodiments, sarilumab is administered subcutaneously at a monthly equivalent dose of about 40 mg. In some embodiments, sarilumab is administered subcutaneously at a monthly equivalent dose of about 80 mg. In some embodiments, sarilumab is administered subcutaneously at a monthly equivalent dose of about 100 mg. In some embodiments, sarilumab is administered subcutaneously at a monthly equivalent dose of about 120 mg. In some embodiments, sarilumab is administered subcutaneously at a monthly equivalent dose of about 200 mg.

In some embodiments, the anti-IL-6R antibody is vobarilizumab. In some embodiments, vobarilizumab is administered intravenously at a monthly equivalent dose of 4-120 mg. In some embodiments, vobarilizumab is administered intravenously at a monthly equivalent dose of about 4 mg. In some embodiments, vobarilizumab is administered intravenously at a monthly equivalent dose of about 6 mg. In some embodiments, vobarilizumab is administered intravenously at a monthly equivalent dose of about 30 mg. In some embodiments, vobarilizumab is administered intravenously at a monthly equivalent dose of about 60 mg. In some embodiments, vobarilizumab is administered intravenously at a monthly equivalent dose of about 84 mg. In some embodiments, vobarilizumab is administered intravenously at a monthly equivalent dose of about 120 mg. In some embodiments, vobarilizumab is administered subcutaneously at a monthly equivalent dose of 7-200 mg. In some embodiments, vobarilizumab is administered subcutaneously at a monthly equivalent dose of about 7 mg. In some embodiments, vobarilizumab is administered subcutaneously at a monthly equivalent dose of about 10 mg. In some embodiments, vobarilizumab is administered subcutaneously at a monthly equivalent dose of about 50 mg. In some embodiments, vobarilizumab is administered subcutaneously at a monthly equivalent dose of about 100 mg. In some embodiments, vobarilizumab is administered subcutaneously at a monthly equivalent dose of about 140 mg. In some embodiments, vobarilizumab is administered subcutaneously at a monthly equivalent dose of about 200 mg.

In some embodiments, the IL-6 antagonist is a JAK inhibitor. In some embodiments, the IL-6 antagonist is a STAT3 inhibitor.

In some embodiments, the patient has a hepcidin-mediated disorder.

In some embodiments, the patient has kidney disease. In some embodiments, the patient has chronic kidney disease. In some embodiments, the patient has KDOQI stage 1-5 chronic kidney disease. In some embodiments, the patient has KDOQI stage 3-5 chronic kidney disease. In some embodiments, the patient is not on dialysis. In some embodiments, the patient has KDOQI stage 5 chronic kidney disease. In some embodiments, the patient is on dialysis. In some embodiments, the patient has cardiorenal syndrome (CRS). In some embodiments, the patient has CRS Type 4.

In some embodiments, the patient has cardiovascular disease. In some embodiments, the patient has diuretic resistant heart failure. In some embodiments, the patient has congestive heart failure (CHF). In some embodiments, the patient has congestive heart failure (CHF) with reduced ejection fraction. In some embodiments, the patient has congestive heart failure (CHF) with mid-range ejection fraction. In some embodiments, the patient has congestive heart failure (CHF) with preserved ejection fraction. In some embodiments, the patient has acute coronary syndrome. In some embodiments, the patient has atherosclerosis.

In some embodiments, the patient has anemia. In some embodiments, the patient has anemia of chronic disease. In some embodiments, the patient has iron-refractory iron-deficiency anemia (IRIDA).

In some embodiments, the patient has diabetes. In some embodiments, the patient has type II diabetes. In some embodiments, the patient has insulin-resistant diabetes.

In some embodiments, the patient has liver disease. In some embodiments, the patient has non-alcoholic steatohepatitis (NASH).

In some embodiments, the patient has osteoporosis.

In some embodiments, the patient has depression.

In some embodiments, the patient has asthma.

In some embodiments, the patient has neuroinflammatory disorder. In some embodiments, the patient has Alzheimer's disease. In some embodiments, the patient has Parkinson's disease. In some embodiments, the patient has multiple sclerosis. In some embodiments, the patient has amyotrophic lateral sclerosis (ALS).

In some embodiments, the patient has age-related macular degeneration (AMD).

In some embodiments, the patient has cancer. In some embodiments, the cancer is selected from the group consisting of: solid tumors, small cell lung cancer, non-small cell lung cancer, hematological cancer, multiple myeloma, leukemia, chronic lymphocytic leukemia (CLL), chronic myeloid leukemia (CIVIL), lymphomas, Hodgkin's lymphoma and hepatic adenoma.

In some embodiments, patient has skin disease.

In some embodiments, the method prevents aging in the patient.

In another aspect, methods for treating inflammation in a patient with cardiovascular disease are provided herein. The methods comprise: administering an IL-6 antagonist to a patient with cardiovascular disease and CRP level greater than 2 mg/L at a dose that is sufficient to reduce CRP levels to 2 mg/L or less without causing neutropenia.

In some embodiments, the IL-6 antagonist is administered at a monthly equivalent dose that is no more than 30% of the monthly equivalent dose for treating rheumatoid arthritis with the same IL-6 antagonist. In some embodiments, the IL-6 antagonist is administered at a monthly equivalent dose that is no more than 20% of the monthly equivalent dose for treating rheumatoid arthritis with the same IL-6 antagonist. In some embodiments, the IL-6 antagonist is administered at a monthly equivalent dose that is no more than 10% of the monthly equivalent dose for treating rheumatoid arthritis with the same IL-6 antagonist.

In another aspect, methods for treating inflammation in a patient with chronic kidney disease (CKD) are provided herein. The methods comprise: administering an IL-6 antagonist to a patient with CKD and a CRP level greater than 2 mg/L at a dose that is sufficient to reduce CRP levels to 2 mg/L or less without causing neutropenia.

In some embodiments, the IL-6 antagonist is administered at a monthly equivalent dose that is no more than 30% of the monthly equivalent dose for treating rheumatoid arthritis with the same IL-6 antagonist. In some embodiments, the IL-6 antagonist is administered at a monthly equivalent dose that is no more than 20% of the monthly equivalent dose for treating rheumatoid arthritis with the same IL-6 antagonist. In some embodiments, the IL-6 antagonist is administered at a monthly equivalent dose that is no more than 10% of the monthly equivalent dose for treating rheumatoid arthritis with the same IL-6 antagonist.

BRIEF DESCRIPTION OF THE DRAWINGS

These and other features, aspects, and advantages of the present invention will become better understood with regard to the following description, and accompanying drawings, where:

FIG. 3A shows the C-reactive protein responder rate after intravenous treatment with COR-001 in patients with stage 5 chronic kidney disease who were on dialysis in the clinical trial described in Example 1. The baseline hsCRP was 12.4 mg/L. Responder was defined as Week 12 average hsCRP <2 mg/L. FIG. 3B shows the C-reactive protein responder rate after treatment with canakinumab in the CANTOS trial, as described in the research literature. The baseline hsCRP was 5.5 mg/L. Responder was defined as 3-month hsCRP <2 mg/L.

FIG. 6A shows the neutrophils adverse responder rate. An Adverse Responder was defined as Week 12 average neutrophils $<2\times10^6$/mL. FIG. 6B shows the platelets adverse responder rate. Adverse responder was defined as Week 12 average platelets $<100\times10^6$/mL.

DETAILED DESCRIPTION

1. Definitions

Figure 1:
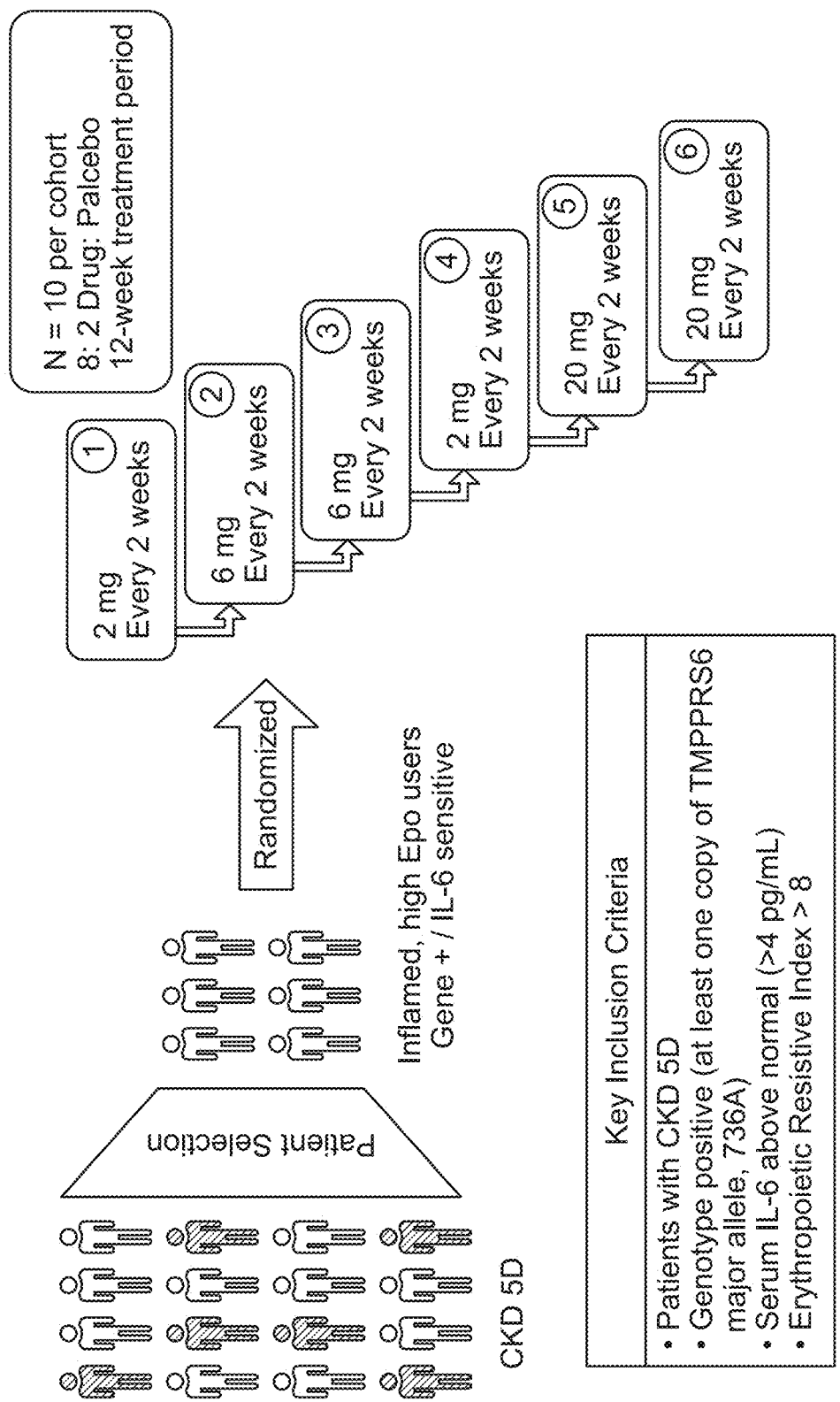
FIG. 1 presents the dose escalation schematic for the phase 1/phase 2 randomized, double-blind, placebo-controlled trial of COR-001 in hemodialysis patients described in Example 1.

Unless defined otherwise, all technical and scientific terms used herein have the meaning commonly understood by one of ordinary skill in the art to which the invention pertains.

As used herein, "interleukin 6 (IL-6)" or "IL-6 polypeptide" refers to a polypeptide or fragment thereof having at least about 85% or greater amino acid identity to the amino acid sequence provided at NCBI Accession No. NP_000591 and having IL-6 biological activity. IL-6 is a pleotropic cytokine with multiple biologic functions. Exemplary IL-6 biological activities include immunostimulatory and pro-inflammatory activities. An exemplary IL-6 amino acid sequence is provided below:

(SEQ ID NO: 1)

```
  1  MCVGARRLGR GPCAALLLLG LGLSTVTGLH CVGDTYPSND RCCHECRPGN GMVSRCSRSQ

61  NTVCRPCGPG FYNDVVSSKP CKPCTWCNLR SGSERKQLCT ATQDTVCRCR AGTQPLDSYK

121  PGVDCAPCPP GHFSPGDNQA CKPWTNCTLA GKHTLQPASN SSDAICEDRD PPATQPQETQ

181  GPPARPITVQ PTEAWPRTSQ GPSTRPVEVP GGRAVAAILG LGLVLGLLGP LAILLALYLL

241  RRDQRLPPDA HKPPGGGSFR TPIQEEQADA HSTLAKI
```

As used herein, "interleukin 6 (IL-6) nucleic acid" refers to a polynucleotide encoding an interleukin 6 (IL-6) polypeptide. An exemplary interleukin 6 (IL-6) nucleic acid sequence is provided at NCBI Accession No. NM_000600. The exemplary sequence at NCBI Accession No. NM_000600 is provided below:

(SEQ ID NO: 2)

```
  1  AATATTAGAG TCTCAACCCC CAATAAATAT AGGACTGGAG ATGTCTGAGG CTCATTCTGC

61  CCTCGAGCCC ACCGGGAACG AAAGAGAAGC TCTATCTCCC CTCCAGGAGC CCAGCTATGA

121  ACTCCTTCTC CACAAGCGCC TTCGGTCCAG TTGCCTTCTC CCTGGGGCTG CTCCTGGTGT

181  TGCCTGCTGC CTTCCCTGCC CCAGTACCCC AGGAGAAGA TTCCAAAGAT GTAGCCGCCC

241  CACACAGACA GCCACTCACC TCTTCAGAAC GAATTGACAA ACAAATTCGG TACATCCTCG

301  ACGGCATCTC AGCCCTGAGA AAGGAGACAT GTAACAAGAG TAACATGTGT GAAAGCAGCA

361  AAGAGGCACT GGCAGAAAAC AACCTGAACC TTCCAAAGAT GGCTGAAAAA GATGGATGCT

421  TCCAATCTGG ATTCAATGAG GAGACTTGCC TGGTGAAAAT CATCACTGGT CTTTTGGAGT

481  TTGAGGTATA CCTAGAGTAC CTCCAGAACA GATTTGAGAG TAGTGAGGAA CAAGCCAGAG

541  CTGTGCAGAT GAGTACAAAA GTCCTGATCC AGTTCCTGCA GAAAAAGGCA AAGAATCTAG

601  ATGCAATAAC CACCCCTGAC CCAACCACAA ATGCCAGCCT GCTGACGAAG CTGCAGGCAC

661  AGAACCAGTG GCTGCAGGAC ATGACAACTC ATCTCATTCT GCGCAGCTTT AAGGAGTTCC

721  TGCAGTCCAG CCTGAGGGCT CTTCGGCAAA TGTAGCATGG GCACCTCAGA TTGTTGTTGT

781  TAATGGGCAT TCCTTCTTCT GGTCAGAAAC CTGTCCACTG GGCACAGAAC TTATGTTGTT
```

```
 841  CTCTATGGAG AACTAAAAGT ATGAGCGTTA GGACACTATT TTAATTATTT TTAATTTATT
 901  AATATTTAAA TATGTGAAGC TGAGTTAATT TATGTAAGTC ATATTTATAT TTTTAAGAAG
 961  TACCACTTGA AACATTTTAT GTATTAGTTT TGAAATAATA ATGGAAAGTG GCTATGCAGT
1021  TTGAATATCC TTTGTTTCAG AGCCAGATCA TTTCTTGGAA AGTGTAGGCT TACCTCAAAT
1081  AAATGGCTAA CTTATACATA TTTTTAAAGA AATATTTATA TTGTATTTAT ATAATGTATA
1141  AATGGTTTTT ATACCAATAA ATGGCATTTT AAAAAATTCA GCAAAAAAAA AAAAAAAAA
1201  A
```

As used herein, "interleukin 6 receptor (IL-6R) complex" refers to a protein complex comprising an IL-6 receptor subunit alpha (IL-6Rα) and interleukin 6 signal transducer glycoprotein 130 (gp130), also termed interleukin 6 receptor subunit β (IL-6Rβ).

As used herein, "interleukin 6 receptor subunit α (IL-6Rα) polypeptide" refers to a polypeptide or fragment thereof having at least about 85% or greater amino acid identity to the amino acid sequence provided at NCBI Accession No. NP_000556 or NP_852004 and having IL-6 receptor biological activity. Exemplary IL-6Rα biological activities include binding to IL-6, binding to glycoprotein 130 (gp130), and regulation of cell growth and differentiation. An exemplary IL-6R sequence is provided below:

```
                                                                (SEQ ID NO: 3)
  1  MLAVGCALLA ALLAAPGAAL APRRCPAQEV ARGVLTSLPG DSVTLTCPGV EPEDNATVHW
 61  VLRKPAAGSH PSRWAGMGRR LLLRSVQLHD SGNYSCYRAG RPAGTVHLLV DVPPEEPQLS
121  CFRKSPLSNV VCEWGPRSTP SLTTKAVLLV RKFQNSPAED FQEPCQYSQE SQKFSCQLAV
181  PEGDSSFYIV SMCVASSVGS KFSKTQTFQG CGILQPDPPA NITVTAVARN PRWLSVTWQD
241  PHSWNSSFYR LRFELRYRAE RSKTFTTWMV KDLQHHCVIH DAWSGLRHVV QLRAQEEFGQ
301  GEWSEWSPEA MGTPWTESRS PPAENEVSTP MQALTTNKDD DNILFRDSAN ATSLPVQDSS
361  SVPLPTFLVA GGSLAFGTLL CIAIVLRFKK TWKLRALKEG KTSMHPPYSL GQLVPERPRP
421  TPVLVPLISP PVSPSSLGSD NTSSHNRPDA RDPRSPYDIS NTDYFFPR
```

As used herein, "glycoprotein 130 (gp130)" or "interleukin 6 receptor subunit β (IL-6Rβ) polypeptide" refers to a polypeptide or fragment thereof having at least about 85% or greater amino acid identity to the amino acid sequence provided at NCBI Accession No. NP_002175, NP_786943, or NP_001177910 and having IL-6 receptor biological activity. Exemplary IL-6Rβ biological activities include binding to IL-6Rα, IL-6 receptor signaling activity, and regulation of cell growth, differentiation, hepcidin expression etc. An exemplary IL-6Rβ sequence is provided below:

```
                                                                (SEQ ID NO: 4)
  1  MLTLQTWLVQ ALFIFLTTES TGELLDPCGY ISPESPVVQL HSNFTAVCVL KEKCMDYFHV
 61  NANYIVWKTN HFTIPKEQYT IINRTASSVT FTDIASLNIQ LTCNILTFGQ LEQNVYGITI
121  ISGLPPEKPK NLSCIVNEGK KMRCEWDGGR ETHLETNFTL KSEWATHKFA DCKAKRDTPT
181  SCTVDYSTVY FVNIEVWVEA ENALGKVTSD HINFDPVYKV KPNPPHNLSV INSEELSSIL
241  KLTWTNPSIK SVIILKYNIQ YRTKDASTWS QIPPEDTAST RSSFTVQDLK PFTEYVFRIR
301  CMKEDGKGYW SDWSEEASGI TYEDRPSKAP SFWYKIDPSH TQGYRTVQLV WKTLPPFEAN
361  GKILDYEVTL TRWKSHLQNY TVNATKLTVN LTNDRYLATL TVRNLVGKSD AAVLTIPACD
421  FQATHPVMDL KAFPKDNMLW VEWTTPRESV KKYILEWCVL SDKAPCITDW QQEDGTVHRT
481  YLRGNLAESK CYLITVTPVY ADGPGSPESI KAYLKQAPPS KGPTVRTKKV GKNEAVLEWD
541  QLPVDVQNGF IRNYTIFYRT IIGNETAVNV DSSHTEYTLS SLTSDTLYMV RMAAYTDEGG
601  KDGPEFTFTT PKFAQGEIEA IVVPVCLAFL LTTLLGVLFC FNKRDLIKKH IWPNVPDPSK
```

```
661  SHIAQWSPHT  PPRHNFNSKD  QMYSDGNFTD  VSVVEIEAND  KKPFPEDLKS  LDLFKKEKIN

721  TEGHSSGIGG  SSCMSSSRPS  ISSSDENESS  QNTSSTVQYS  TVVHSGYRHQ  VPSVQVFSRS

781  ESTQPLLDSE  ERPEDLQLVD  HVDGGDGILP  RQQYFKQNCS  QHESSPDISH  FERSKQVSSV

841  NEEDFVRLKQ  QISDHISQSC  GSGQMKMFQE  VSAADAFGPG  TEGQVERFET  VGMEAATDEG

901  MPKSYLPQTV  RQGGYMPQ
```

Unless otherwise specified, "IL-6 antagonist" refers an agent that is capable of decreasing the biological activity of IL-6. IL-6 antagonists include agents that decrease the level of IL-6 polypeptide in serum, including agents that decrease the expression of an IL-6 polypeptide or nucleic acid; agents that decrease the ability of IL-6 to bind to the IL-6R; agents that decrease the expression of the IL-6R; and agents that decrease signal transduction by the IL-6R receptor when bound by IL-6. In preferred embodiments, the IL-6 antagonist decreases IL-6 biological activity by at least about 10%, 20%, 30%, 50%, 70%, 80%, 90%, 95%, or even 100%. As further described below, IL-6 antagonists include IL-6 binding polypeptides, such as anti-IL-6 antibodies and antigen binding fragments or derivatives thereof; IL-6R binding polypeptides, such as anti-IL-6R antibodies and antigen binding fragments or derivatives thereof; and synthetic chemical molecules, such as JAK1 and JAK3 inhibitors.

The term "IL-6 antibody" or "anti-IL-6 antibody" refers to an antibody that specifically binds IL-6. Anti-IL-6 antibodies include monoclonal and polyclonal antibodies that are specific for IL-6, and antigen-binding fragments or derivatives thereof. IL-6 antibodies are described in greater detail below.

As used herein, the term "IL-6 mediated inflammation" or "IL-6 mediated inflammatory disorder" refers to inflammation or inflammation related disorder in which IL-6 is known or suspected to contribute to the etiology or symptoms of the inflammation.

The term "C-reactive protein" or "CRP" refers to a polypeptide or fragment thereof having at least about 85% or greater amino acid identity to the amino acid sequence provided at NCBI Accession No. NP_000558 and having complement activating activity. CRP levels increase in response to inflammation, and can be measured with an hsCRP (high-sensitivity C-reactive protein) test. An exemplary CRP sequence is provided below:

```
                                                                (SEQ ID NO: 5)
  1   MEKLLCFLVL  TSLSHAFGQT  DMSRKAFVFP  KESDTSYVSL  KAPLTKPLKA  FTVCLHFYTE

61   LSSTRGYSIF  SYATKRQDNE  ILIFWSKDIG  YSFTVGGSEI  LFEVPEVTVA  PVHICTSWES

121   ASGIVEFWVD  GKPRVRKSLK  KGYTVGAEAS  IILGQEQDSF  GGNFEGSQSL  VGDIGNVNMW

181   DFVLSPDEIN  TIYLGGPFSP  NVLNWRALKY  EVQGEVFTKP  QLWP
```

As used herein, "hepcidin" refers to a polypeptide having at least about 85% or greater amino acid identity to the amino acid sequence provided at NCBI Accession No. NP_066998 ("hepcidin preprotein"), or biologically active fragment thereof. Exemplary hepcidin biological activities include binding and reducing the levels of the iron export channel ferroportin, inhibiting iron transport, inhibiting intestinal iron absorption, and inhibiting iron release from macrophages and the liver. An exemplary hepcidin preprotein amino acid sequence is provided below:

```
                                                                (SEQ ID NO: 6)
  1   MALSSQIWAA  CLLLLLLLAS  LTSGSVFPQQ  TGQLAELQPQ  DRAGARASWM  PMFQRRRRRD

61   THFPICIFCC  GCCHRSKCGM  CCKT
```

With reference to the sequence above, hepcidin exists in various forms, including as a preprohormone (amino acids 25-84), prohormone (amino acids 25-84), and mature forms termed hepcidin-25 (amino acids 60-84), hepcidin-22 (amino acids 63-84), and hepcidin-20 (amino acids 65-84).

A "hepcidin-mediated disorder" is any disorder in which hepcidin expression contributes to the etiology of the disorder or any of its symptoms.

The term "immune suppression" or "immunosuppression" refers to a reduction of the activation or efficacy of the immune system. Immune suppression can be measured by the number of white blood cells, such as neutrophils.

As used herein, "neutrophil" of "neutrocyte" refers to a type of white blood cell that is an essential part of the innate immune system. The absolute neutrophil count (ANC) can be used in diagnosis and prognosis. Low neutrophil counts are termed neutropenia.

The term "agent" refers to any compound or composition suitable to be administered in therapy, and explicitly includes chemical compounds; proteins, including antibodies or antigen-binding fragments thereof; peptides; and nucleic acid molecules.

The term "subject" refers to a human or non-human mammal, including, but not limited to, bovine, equine, canine, ovine, feline, and rodent, including murine and rattus, subjects. A "patient" is a human subject in need of treatment.

As used herein, the terms "treat," "treating," "treatment," and the like refer to reducing or ameliorating a disorder, and/or signs or symptoms associated therewith, or slowing or halting the progression thereof. It will be appreciated that, although not precluded, treating a disorder or condition does not require that the disorder, condition or symptoms associated therewith be completely eliminated.

As used herein, "pre-treatment" means prior to the first administration of an IL-6 antagonist according the methods described herein. Pre-treatment does not exclude, and often includes, the prior administration of treatments other than an IL-6 antagonist.

As used herein, "post-treatment" means after the administration of an IL-6 antagonist according the methods described herein. Post-treatment includes after any administration of an IL-6 antagonist at any dosage described herein. Post-treatment also includes after the treatment phase of an IL-6 antagonist.

In this disclosure, "comprises," "comprising," "containing," "having," "includes," "including," and linguistic variants thereof have the meaning ascribed to them in U.S. Patent law, permitting the presence of additional components beyond those explicitly recited.

The term "biological sample" refers to any tissue, cell, fluid, or other material derived from an organism (e.g., human subject). In certain embodiments, the biological sample is serum or blood.

Unless otherwise specified, antibody constant region residue numbering is according to the EU index as in Kabat.

2. Methods of Treating IL-6 Mediated Inflammation

In a first aspect, methods of treating IL-6-mediated inflammation in a patient are presented. The methods comprise administering an IL-6 antagonist to a patient with IL-6-mediated inflammation at a dose that is sufficient to reduce inflammation without causing immune suppression.

2.1. Pre-Treatment Serum CRP and IL-6 Levels

In the methods described herein, the patient has an IL-6-mediated inflammation.

In typical embodiments, the patient has elevated pre-treatment levels of C-reactive protein (CRP).

In some embodiments, the patient has a pre-treatment CRP level at least 2 mg/L. In some embodiments, the patient has a pre-treatment CRP level at least 2 mg/L, 2.5 mg/L, 3 mg/L, 3.5 mg/L, 4 mg/L, 4.5 mg/L, or 5 mg/L. In some embodiments, the patient has pre-treatment CRP levels at least 7.5 mg/L, 10 mg/L, 12.5 mg/L, or 15 mg/L. In various embodiments, the patient has a pre-treatment CRP level at least 2 mg/L. In various embodiments, the patient has a pre-treatment CRP level at least 2.5 mg/L. In various embodiments, the patient has a pre-treatment CRP level at least 5 mg/L. In various embodiments, the patient has a pre-treatment CRP level at least 7.5 mg/L. In various embodiments, the patient has a pre-treatment CRP level at least 10 mg/L. In various embodiments, the patient has a pre-treatment CRP level at least 12.5 mg/L. In various embodiments, the patient has a pre-treatment CRP level at least 15 mg/L.

In some embodiments of the methods described herein, the patient has elevated pre-treatment serum levels of IL-6.

In some embodiments, the patient has a pre-treatment serum IL-6 level of at least 2 pg/ml. In various embodiments, the patient has a pre-treatment serum IL-6 level of at least 2 pg/ml, at least 3 pg/ml, at least 4 pg/ml, at least 5 pg/ml, at least 6 pg/ml, at least 7 pg/ml, at least 8 pg/ml, at least 9 pg/ml, at least 10 pg/ml, at least 11 pg/ml, at least 12 pg/ml, at least 13 pg/ml, at least 14 pg/ml, or at least 15 pg/ml. In certain embodiments, the patient has a pre-treatment serum IL-6 level of at least 2 pg/ml. In certain embodiments, the patient has a pre-treatment serum IL-6 level of at least 2.5 pg/ml. In certain embodiments, the patient has a pre-treatment serum IL-6 level of at least 4 pg/ml. In certain embodiments, the patient has a pre-treatment serum IL-6 level of at least 5 pg/ml. In certain embodiments, the patient has a pre-treatment serum IL-6 level of at least 7.5 pg/ml. In certain embodiments, the patient has a pre-treatment serum IL-6 level of at least 10 pg/ml. In certain embodiments, the patient has a pre-treatment serum IL-6 level of at least 12.5 pg/ml. In certain embodiments, the patient has a pre-treatment serum IL-6 level of at least 15 pg/ml.

In some embodiments, the patient has elevated pre-treatment serum levels of CRP and elevated pre-treatment IL-6 levels. In certain embodiments, the patient has a pre-treatment serum IL-6 level of at least 2 pg/ml and a pre-treatment CRP level at least 2 mg/L. In certain embodiments, the patient has a pre-treatment serum IL-6 level of at least 2 pg/ml and a pre-treatment CRP level at least 2.5 mg/L. In certain embodiments, the patient has a pre-treatment serum IL-6 level of at least 2 pg/ml and a pre-treatment CRP level at least 5 mg/L. In certain embodiments, the patient has a pre-treatment serum IL-6 level of at least 2 pg/ml and a pre-treatment CRP level at least 10 mg/L. In certain embodiments, the patient has a pre-treatment serum IL-6 level of at least 4 pg/ml and a pre-treatment CRP level at least 2 mg/L. In certain embodiments, the patient has a pre-treatment serum IL-6 level of at least 4 pg/ml and a pre-treatment CRP level at least 2.5 mg/L. In certain embodiments, the patient has a pre-treatment serum IL-6 level of at least 4 pg/ml and a pre-treatment CRP level at least 5 mg/L. In certain embodiments, the patient has a pre-treatment serum IL-6 level of at least 4 pg/ml and a pre-treatment CRP level at least 10 mg/L. In certain embodiments, the patient has a pre-treatment serum IL-6 level of at least 5 pg/ml and a pre-treatment CRP level at least 2 mg/L. In certain embodiments, the patient has a pre-treatment serum IL-6 level of at least 5 pg/ml and a pre-treatment CRP level at least 2.5 mg/L. In certain embodiments, the patient has a pre-treatment serum IL-6 level of at least 5 pg/ml and a pre-treatment CRP level at least 5 mg/L. In certain embodiments, the patient has a pre-treatment serum IL-6 level of at least 5 pg/ml and a pre-treatment CRP level at least 10 mg/L. In certain embodiments, the patient has a pre-treatment serum IL-6 level of at least 10 pg/ml and a pre-treatment CRP level at least 2 mg/L. In certain embodiments, the patient has a pre-treatment serum IL-6 level of at least 10 pg/ml and a pre-treatment CRP level at least 2.5 mg/L. In certain embodiments, the patient has a pre-treatment serum IL-6 level of at least 10 pg/ml and a pre-treatment CRP level at least 5 mg/L. In certain embodiments, the patient has a pre-treatment serum IL-6 level of at least 10 pg/ml and a pre-treatment CRP level at least 10 mg/L.

2.2. Reduction of IL-6 and C-Reactive Protein (CRP)

In typical embodiments, the IL-6 antagonist is administered at a dose sufficient to reduce the patient's free serum IL-6 levels below pre-treatment levels.

In some embodiments, the free serum IL-6 level is decreased by at least 10% as compared to pre-treatment levels. In various embodiments, the free serum IL-6 level is decreased by at least 20%, 30%, 40%, 50%, 60%, 70%, 80%, or 90% as compared to pre-treatment levels. In certain embodiments, the free serum IL-6 level is decreased by at least 20% as compared to pre-treatment levels. In certain embodiments, the free serum IL-6 level is decreased by at least 30% as compared to pre-treatment levels. In certain embodiments, the free serum IL-6 level is decreased by at least 40% as compared to pre-treatment levels. In certain embodiments, the free serum IL-6 level is decreased by at least 50% as compared to pre-treatment levels. In certain embodiments, the free serum IL-6 level is decreased by at least 60% as compared to pre-treatment levels. In certain embodiments, the free serum IL-6 level is decreased by at least 70% as compared to pre-treatment levels. In certain embodiments, the free serum IL-6 level is decreased by at least 80% as compared to pre-treatment levels. In certain embodiments, the free serum IL-6 level is decreased by at least 90% as compared to pre-treatment levels.

In some embodiments, the IL-6 antagonist is administered at a dose sufficient to reduce the patient's CRP levels below pre-treatment levels. In some embodiments, the IL-6 mediated inflammation is measured by the CRP levels.

In certain embodiments, the post-treatment CRP level is no more than 5 mg/L. In certain embodiments, the post-treatment CRP level is no more than 2.5 mg/L. In certain embodiments, the post-treatment CRP level is no more than 2 mg/L. In certain embodiments, the post-treatment CRP level is no more than 1 mg/L.

In some embodiments, the CRP level is decreased by at least 10% as compared to pre-treatment levels. In various embodiments, the CRP level is decreased by at least 20%, 30%, 40%, 50%, 60%, 70%, 80%, or 90% as compared to pre-treatment levels. In certain embodiments, the CRP level is decreased by at least 20% as compared to pre-treatment levels. In certain embodiments, the CRP level is decreased by at least 30% as compared to pre-treatment levels. In certain embodiments, the CRP level is decreased by at least 40% as compared to pre-treatment levels. In certain embodiments, the CRP level is decreased by at least 50% as compared to pre-treatment levels. In certain embodiments, the CRP level is decreased by at least 60% as compared to pre-treatment levels. In certain embodiments, the CRP level is decreased by at least 70% as compared to pre-treatment levels. In certain embodiments, the CRP level is decreased by at least 80% as compared to pre-treatment levels. In certain embodiments, the CRP level is decreased by at least 90% as compared to pre-treatment levels.

2.3. Neutrophil Level

2.3.1. Absolute Neutrophil Count (ANC)

In the methods described herein, the IL-6 antagonist is administered at a dose sufficient to reduce inflammation without causing immune suppression.

In some embodiments, the immune suppression of the patient is measured by Absolute Neutrophil Count (ANC). In some embodiments, the post-treatment ANC is at least 300 cells/µL. In various embodiments, the post-treatment ANC is at least 500 cells/µL, 600 cells/µL, 700 cells/µL, 800 cells/µL, 900 cells/µL, 1000 cells/µL, 1100 cells/µL, 1200 cells/µL, 1300 cells/µL, 1400 cells/µL, 1500 cells/µL, 1600 cells/µL, 1700 cells/µL, 1800 cells/µL, 1900 cells/µL, or 2000 cells/µL. In certain embodiments, the post-treatment ANC is at least 500 cells/µL. In certain embodiments, the post-treatment ANC is at least 750 cells/µL. In certain embodiments, the post-treatment ANC is at least 1000 cells/µL. In certain embodiments, the post-treatment ANC is at least 1250 cells/µL. In certain embodiments, the post-treatment ANC is at least 1500 cells/µL. In certain embodiments, the post-treatment ANC is at least 1750 cells/µL. In certain embodiments, the post-treatment ANC is at least 2000 cells/µL.

In some embodiments, the ANC is decreased by no more than 2500 cells/µL as compared to pre-treatment levels. In various embodiments, the ANC is decreased by no more than 2000 cells/µL, 1900 cells/µL, 1800 cells/µL, 1700 cells/µL, 1600 cells/µL, 1500 cells/µL, 1400 cells/µL, 1300 cells/µL, 1200 cells/µL, 1100 cells/µL, 1000 cells/µL, 900 cells/µL, 800 cells/µL, 700 cells/µL, 600 cells/µL, or 500 cells/µL, as compared to pre-treatment levels. In certain embodiments, the ANC is decreased by no more than 2000 cells/µL as compared to pre-treatment levels. In certain embodiments, the ANC is decreased by no more than 1750 cells/µL as compared to pre-treatment levels. In certain embodiments, the ANC is decreased by no more than 1500 cells/µL as compared to pre-treatment levels. In certain embodiments, the ANC is decreased by no more than 1250 cells/µL as compared to pre-treatment levels. In certain embodiments, the ANC is decreased by no more than 1000 cells/µL as compared to pre-treatment levels. In certain embodiments, the ANC is decreased by no more than 750 cells/µL as compared to pre-treatment levels. In certain embodiments, the ANC is decreased by no more than 500 cells/µL as compared to pre-treatment levels.

In some embodiments, the ANC is decreased by no more than 70% as compared to pre-treatment levels. In various embodiments, the ANC is decreased by no more than 60%, 50%, 40%, 30%, 20%, 10%, or 5% as compared to pre-treatment levels. In certain embodiments, the ANC is decreased by no more than 60% as compared to pre-treatment levels. In certain embodiments, the ANC is decreased by no more than 50% as compared to pre-treatment levels. In certain embodiments, the ANC is decreased by no more than 40% as compared to pre-treatment levels. In certain embodiments, the ANC is decreased by no more than 30% as compared to pre-treatment levels. In certain embodiments, the ANC is decreased by no more than 20% as compared to pre-treatment levels. In certain embodiments, the ANC is decreased by no more than 10% as compared to pre-treatment levels. In certain embodiments, the ANC is decreased by no more than 5% as compared to pre-treatment levels.

In some embodiments, the ANC is not decreased as compared to pre-treatment levels.

2.4. Lipoprotein(a) Level

In some embodiments, the IL-6 antagonist is administered at a dose sufficient to reduce the patient's lipoprotein(a) levels below pre-treatment levels.

In some embodiments, the lipoprotein(a) level is decreased by at least 10% as compared to pre-treatment levels. In various embodiments, the lipoprotein(a) level is decreased by at least 20%, 30%, 40%, 50%, 60%, 70%, 80%, or 90% as compared to pre-treatment levels. In certain embodiments, the lipoprotein(a) level is decreased by at least 20% as compared to pre-treatment levels. In certain embodiments, the lipoprotein(a) level is decreased by at least 30% as compared to pre-treatment levels. In certain embodiments, the lipoprotein(a) level is decreased by at least 40% as compared to pre-treatment levels. In certain embodiments, the lipoprotein(a) level is decreased by at least 50% as compared to pre-treatment levels. In certain embodiments, the lipoprotein(a) level is decreased by at least 60% as compared to pre-treatment levels. In certain embodiments, the lipoprotein(a) level is decreased by at least 70% as compared to pre-treatment levels. In certain embodiments, the lipoprotein(a) level is decreased by at least 80% as compared to pre-treatment levels. In certain embodiments, the lipoprotein(a) level is decreased by at least 90% as compared to pre-treatment levels.

2.5. LDL Level

In some embodiments, the IL-6 antagonist is administered at a dose sufficient to reduce the patient's lipoprotein(a) levels without significantly increasing the patent's low-density lipoprotein (LDL) levels.

In some embodiments, the LDL level is increased by no more than 15% as compared to pre-treatment levels. In various embodiments, the LDL level is increased by no more than 12%, 10%, 8%, 6%, 5%, 4%, 3%, 2% or 1% as compared to pre-treatment levels. In certain embodiments, the LDL level is increased by no more than 12% as compared to pre-treatment levels. In certain embodiments, the LDL level is increased by no more than 10% as compared to pre-treatment levels. In certain embodiments, the LDL level is increased by no more than 8% as compared to pre-treatment levels. In certain embodiments, the LDL level is increased by no more than 6% as compared to pre-treatment levels. In certain embodiments, the LDL level is increased by no more than 5% as compared to pre-treatment levels. In certain embodiments, the LDL level is increased by no more than 4% as compared to pre-treatment levels. In certain embodiments, the LDL level is increased by no more than 3% as compared to pre-treatment levels. In certain embodiments, the LDL level is increased by no more than 2% as compared to pre-treatment levels. In certain embodiments, the LDL level is increased by no more than 1% as compared to pre-treatment levels.

In certain embodiments, the LDL level is not increased as compared to pre-treatment levels.

2.6. IL-6 Mediated Inflammatory Disorders

In the methods described herein, the patient has an IL-6 mediated inflammatory disorder.

2.6.1. Non-Hepcidin-Mediated Inflammatory Disorders

In various embodiments, the IL-6 mediated inflammatory disorder is not a hepcidin-mediated disorder. Hepcidin-mediated disorders are described in US 2017/0029499, the disclosure of which is incorporated herein by reference in its entirety.

2.6.2. Hepcidin-Mediated Inflammatory Disorders

In various embodiments, the IL-6 mediated inflammatory disorder is a hepcidin-mediated disorder. Hepcidin-mediated disorders are described in US 2017/0029499, the disclosure of which is incorporated herein by reference in its entirety. In particular embodiments, the patient has a hepcidin-mediated disorder and at least one copy of the major allele at the TMPRSS6 rs855791 SNP (amino acid 736A). In other embodiments, the patient has a hepcidin-mediated disorder and is homozygous for the minor allele at the TMPRSS6 rs855791 SNP (amino acid 736V). In certain embodiments, the patient has a hepcidin-mediated disorder and unknown genotype at the TMPRSS6 rs855791 SNP.

2.6.3. Non-Autoimmune Inflammatory Disorder

In various embodiments, the IL-6 mediated inflammatory disorder is a non-autoimmune IL-6 mediated inflammatory disorder. In particular embodiments, the patient has an IL-6 mediated disorder other than rheumatoid arthritis, giant cell arteritis, polyarticular juvenile idiopathic arthritis, or systemic juvenile idiopathic arthritis.

2.6.4. Kidney Disease

In various embodiments, the patient has kidney disease. In some embodiments, the kidney disease is chronic kidney disease (CKD).

In some embodiments, the patient has KDOQI stage 1-5 chronic kidney disease. In some embodiments, the patient has KDOQI stage 3-5 chronic kidney disease. In some embodiments, the patient has KDOQI stage 1 chronic kidney disease, KDOQI stage 2 chronic kidney disease, KDOQI stage 3 chronic kidney disease, KDOQI stage 4 chronic kidney disease, or KDOQI stage 5 chronic kidney disease. In certain embodiments, the patient has KDOQI stage 5 chronic kidney disease.

In some embodiments, the patient is on dialysis. In some embodiments, the patient is not on dialysis. In certain embodiment, the patient has KDOQI stage 3-5 chronic kidney disease, wherein the patient is not on dialysis. In certain embodiment, the patient has KDOQI stage 5 chronic kidney disease, wherein the patient is on dialysis.

In some embodiments, the patient has cardiorenal syndrome (CRS). In certain embodiments, the patient has CRS Type 4.

In some embodiments, the patient has been treated with dialysis.

2.6.5. Cardiovascular Disease

In various embodiments, the patient has cardiovascular disease.

In some embodiments, the patient has had a previous myocardial infarction. In particular embodiments, the patient has had a previous myocardial infarction and has a CRP level of 2 mg/L or more.

In certain embodiments, the patient has suffered a myocardial infarction within the 60 days prior to first administration of an IL-6 antagonist. In particular embodiments, the patient has suffered a myocardial infarction within the 30 days, 14 days, 7 days, 48 hours, or 24 hours prior to first administration of an IL-6 antagonist.

In some embodiments, the patient has atherosclerosis but has not had a myocardial infarction. In particular embodiments, the patient has atherosclerosis, has not had a myocardial infarction, and has a CRP level of 2 mg/L or more.

In some embodiments, the cardiovascular disease is congestive heart failure (CHF). In certain embodiments, the patient has congestive heart failure (CHF) with reduced ejection fraction. In certain embodiments, the patient has congestive heart failure (CHF) with mid-range ejection fraction. In certain embodiments, the patient has congestive heart failure (CHF) with preserved ejection fraction.

In various embodiments, the IL-6 mediated inflammatory disorder is heart failure that is not diuretic resistant. Diuretic resistant heart failure is described in WO 2018/144773, the disclosure of which is incorporated herein by reference in its entirety.

In some embodiments, the cardiovascular disease is diuretic resistant heart failure. Diuretic resistant heart failure is described in WO 2018/144773, the disclosure of which is incorporated herein by reference in its entirety.

In some embodiments, the cardiovascular disease is acute coronary syndrome.

In certain embodiments, the IL-6 antagonist is administered at a dose sufficient to reduce nonfatal myocardial infarction, nonfatal stroke, and/or cardiovascular death. In some embodiments, the IL-6 antagonist is administered at a dose sufficient to reduce the risk of heart failure. In some embodiments, the IL-6 antagonist is administered at a dose sufficient to increase cardiac function. In some embodiments, the IL-6 antagonist is administered at a dose sufficient to reduce fibrosis after acute myocardial infarction.

2.6.6. Anemia

In various embodiments, the patient has anemia.

In some embodiments, the patient has anemia of chronic disease. In some embodiments, the patient has iron-refractory iron-deficiency anemia (IRIDA).

In some of these embodiments, the patient has been treated with an erythropoiesis-stimulating agent (ESA). In some embodiments, the patient has been treated with iron supplementation. In some embodiments, the patient has been treated with transfusion of blood or packed red blood cells.

In some embodiments, the IL-6 antagonist is administered at a dose sufficient to reverse functional iron deficiency.

2.6.7. Diabetes

In some embodiments, the patient has diabetes. In certain embodiments, the patient has type II diabetes. In certain embodiments, the patient has insulin-resistant diabetes.

2.6.8. Liver Disease

In some embodiments, the patient has liver disease. In certain embodiments, the patient has non-alcoholic steatohepatitis (NASH).

2.6.9. Osteoporosis

In some embodiments, the patient has osteoporosis.

2.6.10. Depression

In some embodiments, the patient has depression.

2.6.11. Asthma

In some embodiments, the patient has asthma.

2.6.12. Neuroinflammatory Disorder

In some embodiments, the patient has neuroinflammatory disorder. In certain embodiments, the patient has Alzheimer's disease. In certain embodiments, the patient has Parkinson's disease. In certain embodiments, the patient has multiple sclerosis. In certain embodiments, the patient has amyotrophic lateral sclerosis (ALS).

2.6.13. Age-Related Macular Degeneration

In some embodiments, the patient has age-related macular degeneration (AMD).

2.6.14. Cancer

In various embodiments, the patient has cancer.

In some embodiments, the cancer is selected from the group consisting of: solid tumors, small cell lung cancer, non-small cell lung cancer, hematological cancer, multiple myeloma, leukemia, chronic lymphocytic leukemia (CLL), chronic myeloid leukemia (CML), lymphomas, and Hodgkin's lymphoma.

2.6.15. Skin Disease

In various embodiments, the patient has skin disease, such as atopic dermatitis or psoriasis.

2.6.16. Aging

In some embodiments, the method prevents aging in the patient.

2.7. IL-6 Antagonists

The IL-6 antagonist used in the methods described herein is capable of decreasing the biological activity of IL-6.

2.7.1. Anti-IL-6 Antibodies

In various embodiments, the IL-6 antagonist is an anti-IL-6 antibody or antigen-binding fragment or derivative thereof.

In typical embodiments, the anti-IL-6 antibody neutralizes the biological activity of IL-6. In some embodiments, the neutralizing antibody prevents binding of IL-6 to the IL-6 receptor.

In some embodiments, the IL-6 antagonist is an anti-IL-6 monoclonal antibody. In some embodiments, the IL-6 antagonist is a polyclonal composition comprising a plurality of species of anti-IL-6 antibodies, each of the plurality having unique CDRs.

In some embodiments, the anti-IL-6 antibody is a Fab, Fab', F(ab')$_2$, Fv, scFv, (scFv)$_2$, single chain antibody molecule, dual variable domain antibody, single variable domain antibody, linear antibody, or V domain antibody.

In some embodiments, the anti-IL-6 antibody comprises a scaffold. In certain embodiments, the scaffold is Fc, optionally human Fc. In some embodiments, the anti-IL-6 antibody comprises a heavy chain constant region of a class selected from IgG, IgA, IgD, IgE, and IgM. In certain embodiments, the anti-IL-6 antibody comprises a heavy chain constant region of the class IgG and a subclass selected from IgG1, IgG2, IgG3, and IgG4.

In some embodiments, the IL-6 antagonist is immunoconjugate or fusion protein comprising an IL-6 antigen-binding fragment.

In some embodiments, the antibody is bispecific or multispecific, with at least one of the antigen-binding portions having specificity for IL-6.

In some embodiments, the antibody is fully human. In some embodiments, the antibody is humanized. In some embodiments, the antibody is chimeric and has non-human V regions and human C region domains. In some embodiments, the antibody is murine.

In typical embodiments, the anti-IL-6 antibody has a $K_D$ for binding human IL-6 of less than 100 nM. In some embodiments, the anti-IL-6 antibody has a $K_D$ for binding human IL-6 of less than 75 nM, 50 nM, 25 nM, 20 nM, 15 nM, or 10 nM. In particular embodiments, the anti-IL-6 antibody has a $K_D$ for binding human IL-6 of less than 5 nM, 4 nM, 3 nM, or 2 nM. In selected embodiments, the anti-IL-6 antibody has a $K_D$ for binding human IL-6 of less than 1 nM, 750 pM, or 500 pM. In specific embodiments, the anti-IL-6 antibody has a $K_D$ for binding human IL-6 of no more than 500 pM, 400 pM, 300 pM, 200 pM, or 100 pM.

In typical embodiments, the anti-IL-6 antibody has an elimination half-life following intravenous administration of at least 7 days. In certain embodiments, the anti-IL-6 antibody has an elimination half-life of at least 14 days, at least 21 days, or at least 30 days.

In some embodiments, the anti-IL-6 antibody has a human IgG constant region with at least one amino acid substitution that extends serum half-life as compared to the unsubstituted human IgG constant domain.

In certain embodiments, the IgG constant domain comprises substitutions at residues 252, 254, and 256, wherein the amino acid substitution at amino acid residue 252 is a substitution with tyrosine, the amino acid substitution at amino acid residue 254 is a substitution with threonine, and the amino acid substitution at amino acid residue 256 is a substitution with glutamic acid ("YTE"). See U.S. Pat. No. 7,083,784, incorporated herein by reference in its entirety. In certain extended half-life embodiments, the IgG constant domain comprises substitutions selected from T250Q/M428L (Hinton et al., *J. Immunology* 176:346-356 (2006)); N434A (Yeung et al., *J. Immunology* 182:7663-7671 (2009)); or T307A/E380A/N434A (Petkova et al., *International Immunology*, 18: 1759-1769 (2006)).

In some embodiments, the elimination half-life of the anti-IL-6 antibody is increased by utilizing the FcRN-binding properties of human serum albumin. In certain embodiments, the antibody is conjugated to albumin (Smith et al., *Bioconjug. Chem.*, 12: 750-756 (2001)). In some embodiments, the anti-IL-6 antibody is fused to bacterial albumin-binding domains (Stork et al., *Prot. Eng. Design Science* 20: 569-76 (2007)). In some embodiments, the anti-IL-6 antibody is fused to an albumin-binding peptide (Nguygen et al., *Prot Eng Design Sel* 19: 291-297 (2006)). In some embodiments, the anti-IL-6 antibody is bispecific, with one specificity being to IL-6, and one specificity being to human serum albumin (Ablynx, WO 2006/122825 (bispecific Nanobody)).

In some embodiments, the elimination half-life of the anti-IL-6 antibody is increased by PEGylation (Melmed et al., *Nature Reviews Drug Discovery* 7: 641-642 (2008)); by HPMA copolymer conjugation (Lu et al., *Nature Biotechnology* 17: 1101-1104 (1999)); by dextran conjugation (*Nuclear Medicine Communications*, 16: 362-369 (1995)); by conjugation with homo-amino-acid polymers (HAPs; HAPylation) (Schlapschy et al., *Prot Eng Design Sel* 20: 273-284 (2007)); or by polysialylation (Constantinou et al., *Bioconjug. Chem.* 20: 924-931 (2009)).

2.7.1.1. COR-001 and Derivatives

In certain preferred embodiments, the anti-IL-6 antibody or antigen-binding portion thereof comprises all six CDRs of COR-001. The COR-001 antibody (also known as MEDI5117) is described in WO 2010/088444 and US 2012/0034212, the disclosures of which are incorporated herein by reference in their entireties. In particular embodiments, the antibody or antigen-binding portion thereof comprises the COR-001 heavy chain V region and light chain V region. In specific embodiments, the antibody is the full-length COR-001 antibody. The COR-001 antibody has the following CDR and heavy and light chain sequences:

```
COR-001 VH CDR1
                                          (SEQ ID NO: 7)
SNYMI

COR-001 VH CDR2
                                          (SEQ ID NO: 8)
DLYYYAGDTYYADSVKG

COR-001 VH CDR3
                                          (SEQ ID NO: 9)
WADDHPPWIDL

COR-001 VL CDR1
                                          (SEQ ID NO: 10)
RASQGISSWLA

COR-001 VL CDR2
                                          (SEQ ID NO: 11)
KASTLES

COR-001 VL CDR3
                                          (SEQ ID NO: 12)
QQSWLGGS

COR-001 Heavy chain
                                          (SEQ ID NO: 13)
EVQLVESGGGLVQPGGSLRLSCAASGFTISSNYMIWVRQAPGKGLEWVS

DLYYYAGDTYYADSVKGRFTMSRDISKNTVYLQMNSLRAEDTAVYYCAR

WADDHPPWIDLWGRGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLYITREPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK

COR-001 Light chain
                                          (SEQ ID NO: 14)
DIQMTQSPSTLSASVGDRVTITCRASQGISSWLAWYQQKPGKAPKVLIY

KASTLESGVPSRFSGSGSGTEFTLTISSLQPDDFATYYCQQSWLGGSFG

QGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC
```

In various embodiments, the anti-IL-6 antibody is a derivative of COR-001.

In some embodiments, the COR-001 derivative includes one or more amino acid substitutions in the COR-001 heavy and/or light chain V regions.

In certain embodiments, the COR-001 derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the COR-001 anti-IL-6 antibody, while retaining specificity for human IL-6.

In certain embodiments, the COR-001 derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of COR-001. The percent sequence identity is determined using BLAST algorithms using default parameters.

In certain embodiments, the COR-001 derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of COR-001. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6).

2.7.1.2. Siltuximab and Derivatives

In certain embodiments, the anti-IL-6 antibody or antigen-binding portion thereof comprises all six CDRs of siltuximab. In particular embodiments, the antibody or antigen-binding portion thereof comprises the siltuximab heavy chain V region and light chain V region. In specific embodiments, the antibody is the full-length siltuximab antibody.

In various embodiments, the anti-IL-6 antibody is a derivative of siltuximab.

In some embodiments, the siltuximab derivative includes one or more amino acid substitutions in the siltuximab heavy and/or light chain V regions.

In certain embodiments, the siltuximab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the siltuximab anti-IL-6 antibody, while retaining specificity for human IL-6.

In certain embodiments, the siltuximab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of siltuximab. The percent sequence identity is determined using BLAST algorithms using default parameters.

In certain embodiments, the siltuximab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of siltuximab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6).

2.7.1.3. Gerilimzumab and Derivatives

In certain embodiments, the anti-IL-6 antibody or antigen-binding portion thereof comprises all six CDRs of gerilimzumab. In particular embodiments, the antibody or antigen-binding portion thereof comprises the gerilimzumab heavy chain V region and light chain V region. In specific embodiments, the antibody is the full-length gerilimzumab antibody.

In various embodiments, the anti-IL-6 antibody is a derivative of gerilimzumab.

In some embodiments, the gerilimzumab derivative includes one or more amino acid substitutions in the gerilimzumab heavy and/or light chain V regions.

In certain embodiments, the gerilimzumab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the gerilimzumab anti-IL-6 antibody, while retaining specificity for human IL-6.

In certain embodiments, the gerilimzumab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of gerilimzumab. The percent sequence identity is determined using BLAST algorithms using default parameters.

In certain embodiments, the gerilimzumab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of gerilimzumab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6).

2.7.1.4. Sirukumab and Derivatives

In certain embodiments, the anti-IL-6 antibody or antigen-binding portion thereof comprises all six CDRs of sirukumab. In particular embodiments, the antibody or antigen-binding portion thereof comprises the sirukumab heavy chain V region and light chain V region. In specific embodiments, the antibody is the full-length sirukumab antibody.

In various embodiments, the anti-IL-6 antibody is a derivative of sirukumab.

In some embodiments, the sirukumab derivative includes one or more amino acid substitutions in the sirukumab heavy and/or light chain V regions.

In certain embodiments, the sirukumab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the sirukumab anti-IL-6 antibody, while retaining specificity for human IL-6.

In certain embodiments, the sirukumab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of sirukumab. The percent sequence identity is determined using BLAST algorithms using default parameters.

In certain embodiments, the sirukumab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of sirukumab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6).

2.7.1.5. Clazakizumab and Derivatives

In certain embodiments, the anti-IL-6 antibody or antigen-binding portion thereof comprises all six CDRs of clazakizumab. In particular embodiments, the antibody or antigen-binding portion thereof comprises the clazakizumab heavy chain V region and light chain V region. In specific embodiments, the antibody is the full-length clazakizumab antibody.

In various embodiments, the anti-IL-6 antibody is a derivative of clazakizumab.

In some embodiments, the clazakizumab derivative includes one or more amino acid substitutions in the clazakizumab heavy and/or light chain V regions.

In certain embodiments, the clazakizumab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the clazakizumab anti-IL-6 antibody, while retaining specificity for human IL-6.

In certain embodiments, the clazakizumab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of clazakizumab. The percent sequence identity is determined using BLAST algorithms using default parameters.

In certain embodiments, the clazakizumab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of clazakizumab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6).

2.7.1.6. Olokizumab and Derivatives

In certain embodiments, the anti-IL-6 antibody or antigen-binding portion thereof comprises all six CDRs of olokizumab. In particular embodiments, the antibody or antigen-binding portion thereof comprises the olokizumab heavy chain V region and light chain V region. In specific embodiments, the antibody is the full-length olokizumab antibody.

In various embodiments, the anti-IL-6 antibody is a derivative of olokizumab.

In some embodiments, the olokizumab derivative includes one or more amino acid substitutions in the olokizumab heavy and/or light chain V regions.

In certain embodiments, the olokizumab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the olokizumab anti-IL-6 antibody, while retaining specificity for human IL-6.

In certain embodiments, the olokizumab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of olokizumab. The percent sequence identity is determined using BLAST algorithms using default parameters.

In certain embodiments, the olokizumab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of olokizumab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6).

2.7.1.7. Other Anti-IL-6 Antibodies and Derivatives

In certain embodiments, the anti-IL-6 antibody or antigen-binding portion thereof comprises all six CDRs of an antibody selected from the group consisting of: VX30 (VOP-R003; Vaccinex), EB-007 (EBI-029; Eleven Bio), and FM101. In particular embodiments, the antibody or antigen-binding portion thereof comprises the heavy chain V region and light chain V region of an antibody selected from the group consisting of: VX30 (VOP-R003; Vaccinex), EB-007 (EBI-029; Eleven Bio), and FM101. In specific embodiments, the antibody is a full-length antibody selected from the group consisting of: VX30 (VOP-R003; Vaccinex), EB-007 (EBI-029; Eleven Bio), and FM101.

In various embodiments, the anti-IL-6 antibody is a derivative of an antibody selected from the group consisting of: VX30 (VOP-R003; Vaccinex), EB-007 (EBI-029; Eleven Bio), and FM101.

2.7.2. Anti-IL-6 Receptor Antibodies

In various embodiments, the IL-6 antagonist is an anti-IL-6 receptor (anti-IL-6R) antibody or antigen-binding fragment or derivative thereof.

In typical embodiments, the anti-IL-6R reduces the biological activity of IL-6 receptor.

In some embodiments, the IL-6 antagonist is an anti-IL-6R monoclonal antibody. In some embodiments, the IL-6 antagonist is a polyclonal composition comprising a plurality of species of anti-IL-6R antibodies, each of the plurality having unique CDRs.

In some embodiments, the anti-IL-6R antibody is a Fab, Fab', F(ab')2, Fv, scFv, (scFv)$_2$, single chain antibody molecule, dual variable domain antibody, single variable domain antibody, linear antibody, or V domain antibody.

In some embodiments, the anti-IL-6R antibody comprises a scaffold. In certain embodiments, the scaffold is Fc, optionally human Fc. In some embodiments, the anti-IL-6R antibody comprises a heavy chain constant region of a class selected from IgG, IgA, IgD, IgE, and IgM. In certain embodiments, the anti-IL-6R antibody comprises a heavy chain constant region of the class IgG and a subclass selected from IgG1, IgG2, IgG3, and IgG4.

In some embodiments, the IL-6 antagonist is immunoconjugate or fusion protein comprising an IL-6R antigen-binding fragment.

In some embodiments, the antibody is bispecific or multispecific, with at least one of the antigen-binding portions having specificity for IL-6 receptor.

In some embodiments, the antibody is fully human. In some embodiments, the antibody is humanized. In some embodiments, the antibody is chimeric and has non-human V regions and human C region domains. In some embodiments, the antibody is murine.

In typical embodiments, the anti-IL-6R antibody has a $K_D$ for binding human IL-6 receptor of less than 100 nM. In some embodiments, the anti-IL-6R antibody has a $K_D$ for binding human IL-6 receptor of less than 75 nM, 50 nM, 25 nM, 20 nM, 15 nM, or 10 nM. In particular embodiments, the anti-IL-6R antibody has a $K_D$ for binding human IL-6 receptor of less than 5 nM, 4 nM, 3 nM, or 2 nM. In selected embodiments, the anti-IL-6R antibody has a $K_D$ for binding human IL-6 receptor of less than 1 nM, 750 pM, or 500 pM. In specific embodiments, the anti-IL-6R antibody has a $K_D$ for binding human IL-6 receptor of no more than 500 pM, 400 pM, 300 pM, 200 pM, or 100 pM.

In typical embodiments, the anti-IL-6R antibody has an elimination half-life following intravenous administration of at least 7 days. In certain embodiments, the anti-IL-6R antibody has an elimination half-life of at least 14 days, at least 21 days, or at least 30 days.

In some embodiments, the anti-IL-6R antibody has a human IgG constant region with at least one amino acid substitution that extends serum half-life as compared to the unsubstituted human IgG constant domain.

In certain embodiments, the IgG constant domain comprises substitutions at residues 252, 254, and 256, wherein the amino acid substitution at amino acid residue 252 is a substitution with tyrosine, the amino acid substitution at amino acid residue 254 is a substitution with threonine, and the amino acid substitution at amino acid residue 256 is a substitution with glutamic acid ("YTE"). See U.S. Pat. No. 7,083,784, incorporated herein by reference in its entirety. In certain extended half-life embodiments, the IgG constant domain comprises substitutions selected from T250Q/M428L (Hinton et al., *J. Immunology* 176:346-356 (2006)); N434A (Yeung et al., *J. Immunology* 182:7663-7671 (2009)); or T307A/E380A/N434A (Petkova et al., *International Immunology*, 18: 1759-1769 (2006)).

In some embodiments, the elimination half-life of the anti-IL-6R antibody is increased by utilizing the FcRN-binding properties of human serum albumin. In certain embodiments, the antibody is conjugated to albumin (Smith et al., *Bioconjug. Chem.*, 12: 750-756 (2001)). In some embodiments, the anti-IL-6R antibody is fused to bacterial albumin-binding domains (Stork et al., *Prot. Eng. Design Science* 20: 569-76 (2007)). In some embodiments, the anti-IL-6R antibody is fused to an albumin-binding peptide (Nguygen et al., *Prot Eng Design Sel* 19: 291-297 (2006)). In some embodiments, the anti-IL-6R antibody is bispecific, with one specificity being to IL-6 receptor, and one specificity being to human serum albumin (Ablynx, WO 2006/122825 (bispecific Nanobody)).

In some embodiments, the elimination half-life of the anti-IL-6R antibody is increased by PEGylation (Melmed et al., *Nature Reviews Drug Discovery* 7: 641-642 (2008)); by HPMA copolymer conjugation (Lu et al., *Nature Biotechnology* 17: 1101-1104 (1999)); by dextran conjugation (*Nuclear Medicine Communications*, 16: 362-369 (1995)); by conjugation with homo-amino-acid polymers (HAPs; HAPylation) (Schlapschy et al., *Prot Eng Design Sel* 20: 273-284 (2007)); or by polysialylation (Constantinou et al., *Bioconjug. Chem.* 20: 924-931 (2009)).

2.7.2.1. Tocilizumab and Derivatives

In certain embodiments, the anti-IL-6R antibody or antigen-binding portion thereof comprises all six CDRs of tocilizumab. In particular embodiments, the antibody or antigen-binding portion thereof comprises the tocilizumab heavy chain V region and light chain V region. In specific embodiments, the antibody is the full-length tocilizumab antibody.

In various embodiments, the anti-IL-6R antibody is a derivative of tocilizumab.

In some embodiments, the tocilizumab derivative includes one or more amino acid substitutions in the tocilizumab heavy and/or light chain V regions.

In certain embodiments, the tocilizumab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the tocilizumab anti-IL-6R antibody, while retaining specificity for human IL-6 receptor.

In certain embodiments, the tocilizumab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of tocilizumab. The percent sequence identity is determined using BLAST algorithms using default parameters.

In certain embodiments, the tocilizumab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of tocilizumab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6 receptor).

2.7.2.2. Sarilumab and Derivatives

In certain embodiments, the anti-IL-6R antibody or antigen-binding portion thereof comprises all six CDRs of sarilumab. In particular embodiments, the antibody or antigen-binding portion thereof comprises the sarilumab heavy chain V region and light chain V region. In specific embodiments, the antibody is the full-length sarilumab antibody.

In various embodiments, the anti-IL-6R antibody is a derivative of sarilumab.

In some embodiments, the sarilumab derivative includes one or more amino acid substitutions in the sarilumab heavy and/or light chain V regions.

In certain embodiments, the sarilumab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the sarilumab anti-IL-6R antibody, while retaining specificity for human IL-6 receptor.

In certain embodiments, the sarilumab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of sarilumab. The percent sequence identity is determined using BLAST algorithms using default parameters.

In certain embodiments, the sarilumab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of sarilumab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6 receptor).

2.7.2.3. Vobarilizumab and Derivatives

In certain embodiments, the anti-IL-6R antibody or antigen-binding portion thereof comprises all six CDRs of vobarilizumab. In particular embodiments, the antibody or antigen-binding portion thereof comprises the vobarilizumab heavy chain V region and light chain V region. In specific embodiments, the antibody is the full-length vobarilizumab antibody.

In various embodiments, the anti-IL-6R antibody is a derivative of vobarilizumab.

In some embodiments, the vobarilizumab derivative includes one or more amino acid substitutions in the vobarilizumab heavy and/or light chain V regions.

In certain embodiments, the vobarilizumab derivative comprises fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, fewer than 2 amino acid substitutions, or 1 amino acid substitution relative to the original $V_H$ and/or $V_L$ of the vobarilizumab anti-IL-6R antibody, while retaining specificity for human IL-6 receptor.

In certain embodiments, the vobarilizumab derivative comprises an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the $V_H$ and $V_L$ domain of vobarilizumab. The percent sequence identity is determined using BLAST algorithms using default parameters.

In certain embodiments, the vobarilizumab derivative comprises an amino acid sequence in which the CDRs comprise an amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the respective CDRs of vobarilizumab. The percent sequence identity is determined using BLAST algorithms using default parameters.

In certain embodiments, the $V_H$ and/or $V_L$ CDR derivatives comprise conservative amino acid substitutions at one or more predicted nonessential amino acid residues (i.e., amino acid residues which are not critical for the antibody to specifically bind to human IL-6 receptor).

2.7.2.4. Other Anti-IL-6R Antibodies and Derivatives

In certain embodiments, the anti-IL-6R antibody or antigen-binding portion thereof comprises all six CDRs of an antibody selected from the group consisting of: SA237 (Roche), NI-1201 (NovImmune), and an antibody described in US 2012/0225060. In particular embodiments, the antibody or antigen-binding portion thereof comprises the heavy chain V region and light chain V region of an antibody selected from the group consisting of: SA237 (Roche), NI-1201 (NovImmune), and an antibody described in US 2012/0225060. In specific embodiments, the antibody is a full-length selected from the group consisting of: SA237 (Roche), NI-1201 (NovImmune), and an antibody described in US 2012/0225060.

In various embodiments, the anti-IL-6R antibody is a derivative of an antibody selected from the group consisting of: SA237 (Roche), NI-1201 (NovImmune), or an antibody described in US 2012/0225060.

2.7.3. Anti-IL-6:IL-6R Complex Antibodies

In various embodiments, the IL-6 antagonist is an antibody specific for the complex of IL-6 and IL-6R. In certain embodiments, the antibody has the six CDRs of an antibody selected from those described in US 2011/0002936, which is incorporated herein by reference in its entirety.

2.7.4. JAK and STAT Inhibitors

In various embodiments, the IL-6 antagonist is an inhibitor of the JAK signaling pathway. In some embodiments, the JAK inhibitor is a JAK1-specific inhibitor. In some embodiments, the JAK inhibitor is a JAK3-specific inhibitor. In some embodiments, the JAK inhibitor is a pan-JAK inhibitor.

In certain embodiments, the JAK inhibitor is selected from the group consisting of tofacitinib (Xeljanz), decernotinib, ruxolitinib, upadacitinib, baricitinib, filgotinib, lestaurtinib, pacritinib, peficitinib, INCB-039110, ABT-494, INCB-047986 and AC-410.

In various embodiments, the IL-6 antagonist is a STAT3 inhibitor. In a specific embodiment, the inhibitor is AZD9150 (AstraZeneca, Isis Pharmaceuticals), a STAT3 antisense molecule.

2.7.5. Additional IL-6 Antagonists

In various embodiments, the IL-6 antagonist is an antagonist peptide.

In certain embodiments, the IL-6 antagonist is C326 (an IL-6 inhibitor by Avidia, also known as ANIG220), or FE301, a recombinant protein inhibitor of IL-6 (Ferring International Center S.A., Conaris Research Institute AG). In some embodiments, the anti-IL-6 antagonist comprises soluble gp130, FE301 (Conaris/Ferring).

2.8. Pharmaceutical Composition

The IL-6 antagonists used in the methods described herein can be formulated in any appropriate pharmaceutical composition for administration by any suitable route of administration. Suitable routes of administration include, but are not limited to, the intravitreal, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

2.9. Dosage Regimens

The IL-6 antagonist is administered at a dose sufficient to reduce inflammation without causing immune suppression.

2.9.1. Antibodies, Antigen-Binding Fragments, Peptides

In typical embodiments, antibody, antigen-binding fragments, and peptide IL-6 antagonists are administered parenterally.

In some parenteral embodiments, the IL-6 antagonist is administered intravenously. In certain intravenous embodiments, the IL-6 antagonist is administered as a bolus. In certain intravenous embodiments, the IL-6 antagonist is administered as an infusion. In certain intravenous embodiments, the IL-6 antagonist is administered as a bolus followed by infusion.

In some parenteral embodiments, the IL-6 antagonist is administered subcutaneously.

In various embodiments, the antibody, antigen-binding fragment, or peptide IL-6 antagonist is administered in a dose that is independent of patient weight or surface area (flat dose).

In some embodiments, the intravenous flat dose is 0.1 mg, 0.2 mg, 0.3 mg, 0.4 mg, 0.5 mg, 0.6 mg, 0.7 mg, 0.8 mg, 0.9 mg, or 1 mg. In some embodiments, the intravenous flat dose is 1 mg, 2 mg, 3 mg, 4 mg, 5 mg, 6 mg, 7 mg, 8 mg, 9 mg, or 10 mg. In some embodiments, the intravenous flat dose is 11 mg, 12 mg, 13 mg, 14 mg, 15 mg, 16 mg, 17 mg, 18 mg, 19 mg, or 20 mg. In some embodiments, the intravenous flat dose is 25 mg, 30 mg, 40 mg, or 50 mg. In some embodiments, the intravenous flat dose is 60 mg, 70 mg, 80 mg, 90 mg, or 100 mg. In some embodiments, the intravenous flat dose is 200 mg, 300 mg, 400 mg, or 500 mg. In some embodiments, the intravenous flat dose is 0.1-1 mg, 1-10 mg, 10-15 mg, 15-20 mg, 20-30 mg, 30-40 mg, or 40-50 mg. In some embodiments, the intravenous flat dose is 1-50 mg, 50-100 mg, or 100 mg-500 mg.

In some embodiments, the subcutaneous flat dose is 0.1 mg, 0.2 mg, 0.3 mg, 0.4 mg, 0.5 mg, 0.6 mg, 0.7 mg, 0.8 mg, 0.9 mg, or 1 mg. In some embodiments, the subcutaneous flat dose is 1 mg, 2 mg, 3 mg, 4 mg, 5 mg, 6 mg, 7 mg, 8 mg, 9 mg, or 10 mg. In some embodiments, the subcutaneous flat dose is 11 mg, 12 mg, 13 mg, 14 mg, 15 mg, 16 mg, 17 mg, 18 mg, 19 mg, or 20 mg. In some embodiments, the subcutaneous flat dose is 25 mg, 30 mg, 40 mg, or 50 mg. In some embodiments, the subcutaneous flat dose is 60 mg, 70 mg, 80 mg, 90 mg, or 100 mg. In some embodiments, the subcutaneous flat dose is 200 mg, 300 mg, 400 mg, or 500 mg. In some embodiments, the subcutaneous flat dose is 0.1-1 mg, 1-10 mg, 10-15 mg, 15-20 mg, 20-30 mg, 30-40 mg, or 40-50 mg. In some embodiments, the subcutaneous flat dose is 1-50 mg, 50-100 mg, or 100 mg-500 mg.

In various embodiments, the antibody, antigen-binding fragment, or peptide IL-6 antagonist is administered as a patient weight-based dose.

In some embodiments, the antagonist is administered at an intravenous dose of 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg or 0.1 mg/kg. In some embodiments, the antagonist is administered at an intravenous dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg or 1.0 mg/kg. In some embodiments, the antagonist is administered at an intravenous dose of 1.5 mg/kg, 2 mg/kg, 2.5 mg/kg, 3 mg/kg, 3.5 mg/kg, 4 mg/kg, 4.5 mg/kg, or 5 mg/kg.

In some embodiments, the antagonist is administered at a subcutaneous dose of 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg or 0.1 mg/kg. In some embodiments, the antagonist is administered at a subcutaneous dose of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg or 1.0 mg/kg. In some embodiments, the antagonist is administered at a subcutaneous dose of 1.5 mg/kg, 2 mg/kg, 2.5 mg/kg, 3 mg/kg, 3.5 mg/kg, 4 mg/kg, 4.5 mg/kg, or 5 mg/kg.

In various intravenous embodiments, the IL-6 antagonist is administered once every 7 days, once every 14 days, once every 21 days, once every 28 days, or once a month. In various subcutaneous embodiments, the IL-6 antagonist is administered once every 14 days, once every 28 days, once a month, once every two months (every other month), or once every three months.

2.9.2. Small Molecule Inhibitors

In typical embodiments, small molecule JAK inhibitors and STAT inhibitors are administered orally.

In various embodiments, the inhibitor is administered once or twice a day at an oral dose of 0.1-1 mg, 1-10 mg, 10-20 mg, 20-30 mg, 30-40 mg, or 40-50 mg. In some embodiments, the inhibitor is administered once or twice a day at a dose of 50-60 mg, 60-70 mg, 70-80 mg, 80-90 mg, or 90-100 mg. In some embodiments, the inhibitor is administered at a dose of 0.1, 0.5, 1, 2, 5, 10, 15, 20, 25, 30, 35, 40, 45, or 50 mg PO once or twice a day. In some embodiments, the inhibitor is administered at a dose of 75 mg or 100 mg PO once or twice a day.

2.9.3. Monthly Equivalent Dose

In typical embodiments, the IL-6 antagonist is administered at a monthly equivalent dose that is less than the monthly equivalent dose for treating rheumatoid arthritis with the same IL-6 antagonist. "Monthly equivalent dose" is the calculated total dose administered per month, regardless of dose amount and dosage schedule.

In some embodiments, the IL-6 antagonist is administered at a monthly equivalent dose no more than 50% of a monthly equivalent dose for treating rheumatoid arthritis with the same IL-6 antagonist. In various embodiments, the IL-6 antagonist is administered at a monthly equivalent dose no more than 45%, 40%, 35%, 30%, 25%, 20%, 15%, 10%, or 5% of a monthly equivalent dose for treating rheumatoid arthritis with the same IL-6 antagonist. In certain embodiments, the IL-6 antagonist is administered at a monthly equivalent dose no more than 45% of a monthly equivalent dose for treating rheumatoid arthritis. In certain embodiments, the IL-6 antagonist is administered at a monthly equivalent dose no more than 40% of a monthly equivalent dose for treating rheumatoid arthritis. In certain embodiments, the IL-6 antagonist is administered at a monthly equivalent dose no more than 30% of a monthly equivalent dose for treating rheumatoid arthritis. In certain embodiments, the IL-6 antagonist is administered at a monthly equivalent dose no more than 25% of a monthly equivalent dose for treating rheumatoid arthritis. In certain embodiments, the IL-6 antagonist is administered at a monthly equivalent dose no more than 20% of a monthly equivalent dose for treating rheumatoid arthritis. In certain embodiments, the IL-6 antagonist is administered at a monthly equivalent dose no more than 15% of a monthly equivalent dose for treating rheumatoid arthritis. In certain embodiments, the IL-6 antagonist is administered at a monthly equivalent dose no more than 10% of a monthly equivalent dose for treating rheumatoid arthritis. In certain embodiments, the IL-6 antagonist is administered at a monthly equivalent dose no more than 5% of a monthly equivalent dose for treating rheumatoid arthritis.

In various embodiments, the IL-6 antagonist is administered at a monthly equivalent dose about 50%, 45%, 40%, 35%, 30%, 25%, 20%, 15%, 10%, or 5% of a monthly equivalent dose for treating rheumatoid arthritis with the same IL-6 antagonist. In certain embodiments, the IL-6 antagonist is administered at a monthly equivalent dose about 50% of a monthly equivalent dose for treating rheumatoid arthritis. In certain embodiments, the IL-6 antagonist is administered at a monthly equivalent dose about 40% of a monthly equivalent dose for treating rheumatoid arthritis. In certain embodiments, the IL-6 antagonist is administered at a monthly equivalent dose about 30% of a monthly equivalent dose for treating rheumatoid arthritis. In certain embodiments, the IL-6 antagonist is administered at a monthly equivalent dose about 25% of a monthly equivalent dose for treating rheumatoid arthritis. In certain embodiments, the IL-6 antagonist is administered at a monthly equivalent dose about 20% of a monthly equivalent dose for treating rheumatoid arthritis. In certain embodiments, the IL-6 antagonist is administered at a monthly equivalent dose about 15% of a monthly equivalent dose for treating rheumatoid arthritis. In certain embodiments, the IL-6 antagonist is administered at a monthly equivalent dose about 10% of a monthly equivalent dose for treating rheumatoid arthritis. In certain embodiments, the IL-6 antagonist is administered at a monthly equivalent dose about 5% of a monthly equivalent dose for treating rheumatoid arthritis.

In some embodiments, the IL-6 antagonist is the COR-001 antibody. In various embodiments, COR-001 is administered intravenously at a monthly equivalent dose of 0.5-50 mg, such as 0.5-1 mg, 0.5-2 mg, 0.5-5 mg, 0.5-10 mg, 0.5-20 mg, 0.5-30 mg, 0.5-40 mg, 1-2 mg, 1-5 mg, 1-10 mg, 1-20 mg, 1-30 mg, 1-40 mg, 1-50 mg, 2-5 mg, 2-10 mg, 2-20 mg, 2-30 mg, 2-40 mg, 2-50 mg, 5-10 mg, 5-20 mg, 5-30 mg, 5-40 mg, 5-50 mg, 10-20 mg, 10-30 mg, 10-40 mg, 10-50 mg, 20-30 mg, 20-40 mg, 20-50 mg, 30-40 mg, 30-50 mg, or 40-50 mg. In certain preferred embodiments, COR-001 is administered intravenously at a monthly equivalent dose of 2-40 mg.

In various embodiments, COR-001 is administered intravenously at a monthly equivalent dose of about 0.5 mg, 1 mg, 2 mg, 3 mg, 4 mg, 5 mg, 6 mg, 7 mg, 8 mg, 9 mg, 10 mg, 20 mg, 30 mg, 40 mg, or 50 mg. In certain embodiments, COR-001 is administered intravenously at a monthly equivalent dose of about 1 mg. In certain embodiments, COR-001 is administered intravenously at a monthly equivalent dose of about 2 mg. In certain embodiments, COR-001 is administered intravenously at a monthly equivalent dose of about 3 mg. In certain embodiments, COR-001 is administered intravenously at a monthly equivalent dose of about 4 mg. In certain embodiments, COR-001 is administered intravenously at a monthly equivalent dose of about 5 mg. In certain embodiments, COR-001 is administered intravenously at a monthly equivalent dose of about 6 mg. In certain embodiments, COR-001 is administered intravenously at a monthly equivalent dose of about 10 mg. In certain embodiments, COR-001 is administered intravenously at a monthly equivalent dose of about 12 mg. In certain embodiments, COR-001 is administered intravenously at a monthly equivalent dose of about 15 mg. In certain embodiments, COR-001 is administered intravenously at a monthly equivalent dose of about 20 mg. In certain embodiments, COR-001 is administered intravenously at a monthly equivalent dose of about 40 mg.

In various embodiments, COR-001 is administered subcutaneously at a monthly equivalent dose of 1-100 mg, such as 1-2 mg, 1-5 mg, 1-10 mg, 1-20 mg, 1-30 mg, 1-40 mg, 1-50 mg, 1-70 mg, 1-100 mg, 2-5 mg, 2-10 mg, 2-20 mg, 2-30 mg, 2-40 mg, 2-50 mg, 2-70 mg, 2-100 mg, 3-5 mg, 3-10 mg, 3-20 mg, 3-30 mg, 3-40 mg, 3-50 mg, 3-70 mg, 3-100 mg, 5-10 mg, 5-20 mg, 5-30 mg, 5-40 mg, 5-50 mg, 5-70 mg, 5-100 mg, 10-20 mg, 10-30 mg, 10-40 mg, 10-50 mg, 10-70 mg, 10-100 mg, 20-30 mg, 20-40 mg, 20-50 mg, 20-70 mg, 20-100 mg, 30-40 mg, 30-50 mg, 30-70 mg, 30-100 mg, or 40-100 mg. In certain preferred embodiments, COR-001 is administered subcutaneously at a monthly equivalent dose of 3-70 mg.

In various embodiments, COR-001 is administered subcutaneously at a monthly equivalent dose of about 0.5 mg, 1 mg, 2 mg, 3 mg, 4 mg, 5 mg, 6 mg, 7 mg, 8 mg, 9 mg, 10 mg, 20 mg, 30 mg, 40 mg, 50 mg, 70 mg, or 100 mg. In certain embodiments, COR-001 is administered subcutaneously at a monthly equivalent dose of about 1 mg. In certain embodiments, COR-001 is administered subcutaneously at a monthly equivalent dose of about 2 mg. In certain embodiments, COR-001 is administered subcutaneously at a monthly equivalent dose of about 3 mg. In certain embodiments, COR-001 is administered subcutaneously at a monthly equivalent dose of about 4 mg. In certain embodiments, COR-001 is administered subcutaneously at a monthly equivalent dose of about 5 mg. In certain embodiments, COR-001 is administered subcutaneously at a monthly equivalent dose of about 6 mg. In certain embodiments, COR-001 is administered subcutaneously at a monthly equivalent dose of about 10 mg. In certain embodiments, COR-001 is administered subcutaneously at a monthly equivalent dose of about 12 mg. In certain embodiments, COR-001 is administered subcutaneously at a monthly equivalent dose of about 15 mg. In certain embodiments, COR-001 is administered subcutaneously at a monthly equivalent dose of about 17 mg. In certain embodiments, COR-001 is administered subcutaneously at a monthly equivalent dose of about 20 mg. In certain embodiments, COR-001 is administered subcutaneously at a monthly equivalent dose of about 35 mg. In certain embodiments, COR-001 is administered subcutaneously at a monthly equivalent dose of about 40 mg. In certain embodiments, COR-001 is administered subcutaneously at a monthly equivalent dose of about 70 mg. In certain embodiments, COR-001 is administered subcutaneously at a monthly equivalent dose of about 100 mg.

In some embodiments, the IL-6 antagonist is siltuximab. In various embodiments, siltuximab is administered intravenously at a monthly equivalent dose of 10-500 mg, such as 10-20 mg, 10-30 mg, 10-40 mg, 10-50 mg, 10-100 mg, 10-150 mg, 10-200 mg, 10-300 mg, 10-400 mg, 20-30 mg, 20-40 mg, 20-50 mg, 20-100 mg, 20-150 mg, 20-200 mg, 20-300 mg, 20-400 mg, 20-500 mg, 30-40 mg, 30-50 mg, 30-100 mg, 30-150 mg, 30-200 mg, 30-300 mg, 30-400 mg, 30-500 mg, 40-50 mg, 40-100 mg, 40-150 mg, 40-200 mg, 40-250 mg, 40-300 mg, 40-400 mg, 40-500 mg, 50-100 mg, 50-150 mg, 50-200 mg, 50-300 mg, 50-400 mg, 50-500 mg, 100-150 mg, 100-200 mg, 100-300 mg, 100-400 mg, 100-500 mg, 150-200 mg, 150-300 mg, 150-400 mg, 150-500 mg, 200-300 mg, 200-400 mg, 200-500 mg, 300-400 mg, 300-500 mg, or 400-500 mg. In certain preferred embodiments, siltuximab is administered intravenously at a monthly equivalent dose of 50-500 mg. In various embodiments, siltuximab is administered intravenously at a monthly equivalent dose of about 10 mg, 20 mg, 30 mg, 40 mg, 50 mg, 100 mg, 150 mg, 200 mg, 300 mg, 400 mg, or 500 mg. In certain embodiments, siltuximab is administered intravenously at a monthly equivalent dose of about 50 mg. In certain embodiments, siltuximab is administered intravenously at a monthly equivalent dose of about 100 mg. In certain embodiments, siltuximab is administered intravenously at a monthly equivalent dose of about 150 mg. In certain embodiments, siltuximab is administered intravenously at a monthly equivalent dose of about 200 mg. In certain embodiments, siltuximab is administered intravenously at a monthly equivalent dose of about 300 mg. In certain embodiments, siltuximab is administered intravenously at a monthly equivalent dose of about 500 mg.

In various embodiments, siltuximab is administered subcutaneously at a monthly equivalent dose of 50-1000 mg, such as 50-80 mg, 50-100 mg, 50-160 mg, 50-200 mg, 50-240 mg, 50-320 mg, 50-480 mg, 50-800 mg, 80-100 mg, 80-160 mg, 80-200 mg, 80-240 mg, 80-320 mg, 80-480 mg, 80-800 mg, 80-1000 mg, 100-160 mg, 100-200 mg, 100-240 mg, 100-320 mg, 100-480 mg, 100-800 mg, 100-1000 mg, 160-200 mg, 160-240 mg, 160-320 mg, 160-480 mg, 160-800 mg, 160-1000 mg, 200-240 mg, 200-320 mg, 200-480 mg, 200-800 mg, 200-1000 mg, 240-320 mg, 240-480 mg, 240-800 mg, 240-1000 mg, 320-480 mg, 320-800 mg, 320-1000 mg, 480-800 mg, 480-1000 mg, or 800-1000 mg. In certain preferred embodiments, siltuximab is administered subcutaneously at a monthly equivalent dose of 80-800 mg. In various embodiments, siltuximab is administered subcutaneously at a monthly equivalent dose of about 50 mg, 80 mg. 100 mg, 160 mg, 240 mg. 320 mg, 480 mg. 800 mg, or 1000 mg. In certain embodiments, siltuximab is administered subcutaneously at a monthly equivalent dose of about 50 mg. In certain embodiments, siltuximab is administered subcutaneously at a monthly equivalent dose of about 80 mg. In certain embodiments, siltuximab is administered subcutaneously at a monthly equivalent dose of about 100 mg. In certain embodiments, siltuximab is administered subcutaneously at a monthly equivalent dose of about 160 mg. In certain embodiments, siltuximab is administered subcutaneously at a monthly equivalent dose of about 240 mg. In certain embodiments, siltuximab is administered subcutaneously at a monthly equivalent dose of about 320 mg. In certain embodiments, siltuximab is administered subcutaneously at a monthly equivalent dose of about 480 mg. In certain embodiments, siltuximab is administered subcutaneously at a monthly equivalent dose of about 800 mg. In certain embodiments, siltuximab is administered subcutaneously at a monthly equivalent dose of about 1000 mg.

In some embodiments, the IL-6 antagonist is gerilimzumab. In various embodiments, gerilimzumab is administered intravenously at a monthly equivalent dose of 0.05-2 mg, such as 0.05-0.075 mg, 0.05-0.1 mg, 0.05-0.12 mg, 0.05-0.3 mg, 0.05-0.6 mg, 0.05-0.9 mg, 0.05-1.8 mg, 0.075-0.1 mg, 0.075-0.12 mg, 0.075-0.3 mg, 0.075-0.6 mg, 0.075-0.9 mg, 0.075-1.8 mg, 0.075-2 mg, 0.1-0.12 mg, 0.1-0.3 mg, 0.1-0.6 mg, 0.1-0.9 mg, 0.1-1.8 mg, 0.1-2 mg, 0.12-0.3 mg, 0.12-0.6 mg, 0.12-0.9 mg, 0.12-1.8 mg, 0.12-2 mg, 0.3-0.6 mg, 0.3-0.9 mg, 0.3-1.8 mg, 0.3-2 mg, 0.6-0.9 mg, 0.6-1.8 mg, 0.6-2 mg, 0.9-1.8 mg, 0.9-2 mg, or 1.8-2 mg. In certain preferred embodiments, gerilimzumab is administered intravenously at a monthly equivalent dose of 0.075-1.8 mg. In various embodiments, gerilimzumab is administered intravenously at a monthly equivalent dose of about 0.05 mg, 0.075 mg, 0.1 mg, 0.12 mg, 0.3 mg, 0.6 mg, 0.9 mg, 1.8 mg, or 2 mg. In certain embodiments, gerilimzumab is administered intravenously at a monthly equivalent dose of about 0.05 mg. In certain embodiments, gerilimzumab is administered intravenously at a monthly equivalent dose of about 0.075 mg. In certain embodiments, gerilimzumab is administered intravenously at a monthly equivalent dose of about 0.1 mg. In certain embodiments, gerilimzumab is administered intravenously at a monthly equivalent dose of about 0.12 mg. In certain embodiments, gerilimzumab is administered intravenously at a monthly equivalent dose of about 0.3 mg. In certain embodiments, gerilimzumab is administered intravenously at a monthly equivalent dose of about 0.6 mg. In certain embodiments, gerilimzumab is administered intravenously at a monthly equivalent dose of about 0.9 mg. In certain embodiments, gerilimzumab is administered intravenously at a monthly equivalent dose of about 1.8 mg. In certain embodiments, gerilimzumab is administered intravenously at a monthly equivalent dose of about 2 mg.

In various embodiments, gerilimzumab is administered subcutaneously at a monthly equivalent dose of 0.1-5 mg, such as 0.1-0.125 mg, 0.1-0.15 mg, 0.1-0.2 mg, 0.1-0.5 mg, 0.1-1 mg, 0.1-1.5 mg, 0.1-2 mg, 0.1-3 mg, 0.1-4 mg, 0.125-0.15 mg, 0.125-0.2 mg, 0.125-0.5 mg, 0.125-1 mg, 0.125-1.5 mg, 0.125-2 mg, 0.125-3 mg, 0.125-4 mg, 0.125-5 mg, 0.15-0.2 mg, 0.15-0.5 mg, 0.15-1 mg, 0.15-1.5 mg, 0.15-2 mg, 0.15-3 mg, 0.15-4 mg, 0.15-5 mg, 0.2-0.5 mg, 0.2-1 mg, 0.2-1.5 mg, 0.2-2 mg, 0.2-3 mg, 0.2-4 mg, 0.2-5 mg, 0.5-1 mg, 0.5-1.5 mg, 0.5-2 mg, 0.5-3 mg, 0.5-4 mg, 0.5-5 mg, 1-1.5 mg, 1-2 mg, 1-3 mg, 1-4 mg, 1-5 mg, 1.5-2 mg, 1.5-3 mg, 1.5-4 mg, 1.5-5 mg, 2-3 mg, 2-4 mg, 2-5 mg, 3-4 mg, 3-5 mg, or 4-5 mg. In certain preferred embodiments, gerilimzumab is administered subcutaneously at a monthly equivalent dose of 0.125-3 mg. In various embodiments, gerilimzumab is administered subcutaneously at a monthly equivalent dose of about 0.1 mg, 0.125 mg, 0.15 mg, 0.2 mg, 0.5 mg, 1 mg, 1.5 mg, 2 mg, 3 mg, 4 mg, or 5 mg. In certain embodiments, gerilimzumab is administered subcutaneously at a monthly equivalent dose of about 0.125 mg. In certain embodiments, gerilimzumab is administered subcutaneously at a monthly equivalent dose of about 0.2 mg. In certain embodiments, gerilimzumab is administered subcutaneously at a monthly equivalent dose of about 0.5 mg. In certain embodiments, gerilimzumab is administered subcutaneously at a monthly equivalent dose of about 1 mg. In certain embodiments, gerilimzumab is administered subcutaneously at a monthly equivalent dose of about 1.5 mg. In certain embodiments, gerilimzumab is administered subcutaneously at a monthly equivalent dose of about 3 mg.

In some embodiments, the IL-6 antagonist is sirukumab. In various embodiments, sirukumab is administered intravenously at a monthly equivalent dose of 1-80 mg, such as 1-1.5 mg, 1-3 mg, 1-6 mg, 1-12 mg, 1-36 mg, 1-60 mg, 1.5-3 mg, 1.5-6 mg, 1.5-12 mg, 1.5-36 mg, 1.5-60 mg, 1.5-80 mg, 3-6 mg, 3-12 mg, 3-36 mg, 3-60 mg, 3-80 mg, 6-12 mg, 6-36 mg, 6-60 mg, 6-80 mg, 12-36 mg, 12-60 mg, 12-80 mg, 36-60 mg, 36-80 mg, or 60-80 mg. In certain preferred embodiments, sirukumab is administered intravenously at a monthly equivalent dose of 1.5-60 mg. In various embodiments, sirukumab is administered intravenously at a monthly equivalent dose of about 1 mg, 1.5 mg, 3 mg, 6 mg, 12 mg, 36 mg, 60 mg, or 80 mg. In certain embodiments, sirukumab is administered intravenously at a monthly equivalent dose of about 1 mg. In certain embodiments, sirukumab is administered intravenously at a monthly equivalent dose of about 1.5 mg. In certain embodiments, sirukumab is administered intravenously at a monthly equivalent dose of about 3 mg. In certain embodiments, sirukumab is administered intravenously at a monthly equivalent dose of about 6 mg. In certain embodiments, sirukumab is administered intravenously at a monthly equivalent dose of about 12 mg. In certain embodiments, sirukumab is administered intravenously at a monthly equivalent dose of about 36 mg. In certain embodiments, sirukumab is administered intravenously at a monthly equivalent dose of about 60 mg. In certain embodiments, sirukumab is administered intravenously at a monthly equivalent dose of about 80 mg.

In various embodiments, sirukumab is administered subcutaneously at a monthly equivalent dose of 1-100 mg, such as 1-2.5 mg, 1-5 mg, 1-10 mg, 1-20 mg, 1-30 mg, 1-40 mg, 1-50 mg, 1-60 mg, 2.5-5 mg, 2.5-10 mg, 2.5-20 mg, 2.5-30 mg, 2.5-40 mg, 2.5-50 mg, 2.5-60 mg, 2.5-100 mg, 5-10 mg, 5-20 mg, 5-30 mg, 5-40 mg, 5-50 mg, 5-60 mg, 5-100 mg, 10-20 mg, 10-30 mg, 10-40 mg, 10-50 mg, 10-60 mg, 10-100 mg, 20-30 mg, 20-40 mg, 20-50 mg, 20-60 mg, 20-100 mg, 30-40 mg, 30-50 mg, 30-60 mg, 30-100 mg, 40-50 mg, 40-60 mg, 40-100 mg, 50-60 mg, 50-100 mg, or 60-100 mg. In certain preferred embodiments, sirukumab is administered subcutaneously at a monthly equivalent dose of 2.5-100 mg. In various embodiments, sirukumab is administered subcutaneously at a monthly equivalent dose of about 1 mg, 2.5 mg, 5 mg, 10 mg, 20 mg, 30 mg, 40 mg, 50 mg, 60 mg, or 100 mg. In certain embodiments, sirukumab is administered subcutaneously at a monthly equivalent dose of about 2.5 mg. In certain embodiments, sirukumab is administered subcutaneously at a monthly equivalent dose of about 5 mg. In certain embodiments, sirukumab is administered subcutaneously at a monthly equivalent dose of about 10 mg. In certain embodiments, sirukumab is administered subcutaneously at a monthly equivalent dose of about 20 mg. In certain embodiments, sirukumab is administered subcutaneously at a monthly equivalent dose of about 60 mg. In certain embodiments, sirukumab is administered subcutaneously at a monthly equivalent dose of about 100 mg.

In some embodiments, the IL-6 antagonist is clazakizumab. In various embodiments, clazakizumab is administered intravenously at a monthly equivalent dose of 1-80 mg, such as 1-3 mg, 1-6 mg, 1-12 mg, 1-24 mg, 1-36 mg, 1-60 mg, 3-6 mg, 3-12 mg, 3-24 mg, 3-36 mg, 3-60 mg, 3-80 mg, 6-12 mg, 6-24 mg, 6-36 mg, 6-60 mg, 6-80 mg, 12-24 mg, 12-36 mg, 12-60 mg, 12-80 mg, 24-36 mg, 24-60 mg, 24-80 mg, 36-60 mg, 36-80 mg, or 60-80 mg. In certain preferred embodiments, clazakizumab is administered intravenously at a monthly equivalent dose of 3-60 mg. In various embodiments, clazakizumab is administered intravenously at a monthly equivalent dose of about 1 mg, 3 mg, 6 mg, 12 mg, 24 mg, 36 mg, 60 mg or 80 mg. In certain embodiments, clazakizumab is administered intravenously at a monthly equivalent dose of about 1 mg. In certain embodiments, clazakizumab is administered intravenously at a monthly equivalent dose of about 3 mg. In certain embodiments, clazakizumab is administered intravenously at a monthly equivalent dose of about 6 mg. In certain embodiments, clazakizumab is administered intravenously at a monthly equivalent dose of about 12 mg. In certain embodiments, clazakizumab is administered intravenously at a monthly equivalent dose of about 24 mg. In certain embodiments, clazakizumab is administered intravenously at a monthly equivalent dose of about 36 mg. In certain embodiments, clazakizumab is administered intravenously at a monthly equivalent dose of about 60 mg. In certain embodiments, clazakizumab is administered intravenously at a monthly equivalent dose of about 80 mg.

In various embodiments, clazakizumab is administered subcutaneously at a monthly equivalent dose of 1-100 mg, such as 1-2 mg, 1-5 mg, 1-10 mg, 1-20 mg, 1-30 mg, 1-40 mg, 1-50 mg, 1-60 mg, 2-5 mg, 2-10 mg, 2-20 mg, 2-30 mg, 2-40 mg, 2-50 mg, 2-60 mg, 2-100 mg, 5-10 mg, 5-20 mg, 5-30 mg, 5-40 mg, 5-50 mg, 5-60 mg, 5-100 mg, 10-20 mg, 10-30 mg, 10-40 mg, 10-50 mg, 10-60 mg, 10-100 mg, 20-30 mg, 20-40 mg, 20-50 mg, 20-60 mg, 20-100 mg, 30-40 mg, 30-50 mg, 30-60 mg, 30-100 mg, 40-50 mg, 40-60 mg, 40-100 mg, 50-60 mg, 50-100 mg, or 60-100 mg. In certain preferred embodiments, clazakizumab is administered subcutaneously at a monthly equivalent dose of 5-100 mg. In various embodiments, clazakizumab is administered subcutaneously at a monthly equivalent dose of about 1 mg, 2 mg, 5 mg, 10 mg, 20 mg, 30 mg, 40 mg, 50 mg, 60 mg, or 100 mg. In certain embodiments, clazakizumab is administered subcutaneously at a monthly equivalent dose of about 5 mg. In certain embodiments, clazakizumab is administered subcutaneously at a monthly equivalent dose of about 10 mg. In certain embodiments, clazakizumab is administered subcutaneously at a monthly equivalent dose of about 20 mg. In certain embodiments, clazakizumab is administered subcutaneously at a monthly equivalent dose of about 40 mg. In certain embodiments, clazakizumab is administered subcutaneously at a monthly equivalent dose of about 60 mg. In certain embodiments, clazakizumab is administered subcutaneously at a monthly equivalent dose of about 100 mg.

In some embodiments, the IL-6 antagonist is olokizumab. In various embodiments, olokizumab is administered intravenously at a monthly equivalent dose of 1-80 mg, such as 1-1.8 mg, 1-3.6 mg, 1-9 mg, 1-18 mg, 1-45 mg, 1-60 mg, 1.8-3.6 mg, 1.8-9 mg, 1.8-18 mg, 1.8-45 mg, 1.8-60 mg, 1.8-80 mg, 3.6-9 mg, 3.6-18 mg, 3.6-45 mg, 3.6-60 mg, 3.6-80 mg, 9-18 mg, 9-45 mg, 9-60 mg, 9-80 mg, 18-45 mg, 18-60 mg, 18-80 mg, 45-60 mg, 45-80 mg, or 60-80 mg. In certain preferred embodiments, olokizumab is administered intravenously at a monthly equivalent dose of 1.8-60 mg. In various embodiments, olokizumab is administered intravenously at a monthly equivalent dose of about 1 mg, 1.8 mg, 3.6 mg, 9 mg, 18 mg. 45 mg, 60 mg, or 80 mg. In certain embodiments, olokizumab is administered intravenously at a monthly equivalent dose of about 1 mg. In certain embodiments, olokizumab is administered intravenously at a monthly equivalent dose of about 1.8 mg. In certain embodiments, olokizumab is administered intravenously at a monthly equivalent dose of about 3.6 mg. In certain embodiments, olokizumab is administered intravenously at a monthly equivalent dose of about 9 mg. In certain embodiments, olokizumab is administered intravenously at a monthly equivalent dose of about 18 mg. In certain embodiments, olokizumab is administered intravenously at a monthly equivalent dose of about 45 mg. In certain embodiments, olokizumab is administered intravenously at a monthly equivalent dose of about 60 mg. In certain embodiments, olokizumab is administered intravenously at a monthly equivalent dose of about 80 mg.

In various embodiments, olokizumab is administered subcutaneously at a monthly equivalent dose of 1-100 mg, such as 1-3 mg, 1-6 mg, 1-10 mg, 1-15 mg, 1-20 mg, 1-30 mg, 1-50 mg, 1-72 mg, 3-6 mg, 3-10 mg, 3-15 mg, 3-20 mg, 3-30 mg, 3-50 mg, 3-72 mg, 3-100 mg, 6-10 mg, 6-15 mg, 6-20 mg, 6-30 mg, 6-50 mg, 6-72 mg, 6-100 mg, 10-15 mg, 10-20 mg, 10-30 mg, 10-50 mg, 10-72 mg, 10-100 mg, 15-20 mg, 15-30 mg, 15-50 mg, 15-72 mg, 15-100 mg, 20-30 mg, 20-50 mg, 20-72 mg, 20-100 mg, 30-50 mg, 30-72 mg, 30-100 mg, 50-72 mg, 50-100 mg, or 72-100 mg. In certain preferred embodiments, olokizumab is administered subcutaneously at a monthly equivalent dose of 3-100 mg. In various embodiments, olokizumab is administered subcutaneously at a monthly equivalent dose of about 1 mg, 3 mg, 6 mg, 10 mg, 15 mg, 20 mg, 30 mg, 50 mg, 72 mg, or 100 mg. In certain embodiments, olokizumab is administered subcutaneously at a monthly equivalent dose of about 3 mg. In certain embodiments, olokizumab is administered subcutaneously at a monthly equivalent dose of about 6 mg. In certain embodiments, olokizumab is administered subcutaneously at a monthly equivalent dose of about 15 mg. In certain embodiments, olokizumab is administered subcutaneously at a monthly equivalent dose of about 30 mg. In certain embodiments, olokizumab is administered subcutaneously at a monthly equivalent dose of about 72 mg. In certain embodiments, olokizumab is administered subcutaneously at a monthly equivalent dose of about 100 mg.

In some embodiments, the IL-6 antagonist is tocilizumab. In various embodiments, tocilizumab is administered intravenously at a monthly equivalent dose of 10-500 mg, such as 10-20 mg, 10-50 mg, 10-100 mg, 10-150 mg, 10-200 mg, 10-250 mg, 10-300 mg, 10-350 mg, 10-400 mg, 20-50 mg, 20-100 mg, 20-150 mg, 20-200 mg, 20-250 mg, 20-300 mg, 20-350 mg, 20-400 mg, 20-500 mg, 50-100 mg, 50-150 mg, 50-200 mg, 50-250 mg, 50-300 mg, 50-350 mg, 50-400 mg, 50-500 mg, 100-150 mg, 100-200 mg, 100-250 mg, 100-300 mg, 100-350 mg, 100-400 mg, 100-500 mg, 150-200 mg, 150-250 mg, 150-300 mg, 150-350 mg, 150-400 mg, 150-500 mg, 200-250 mg, 200-300 mg, 200-350 mg, 200-400 mg, 200-500 mg, 250-300 mg, 250-350 mg, 250-400 mg, 250-500 mg, 300-350 mg, 300-400 mg, 300-500 mg, 350-400 mg, 350-500 mg, or 400-500 mg. In certain preferred embodiments, tocilizumab is administered intravenously at a monthly equivalent dose of 50-500 mg. In various embodiments, tocilizumab is administered intravenously at a monthly equivalent dose of about 10 mg, 20 mg, 30 mg, 40 mg, 50 mg, 100 mg, 150 mg, 200 mg, 250 mg, 300 mg, 350 mg, 400 mg, or 500 mg. In certain embodiments, tocilizumab is administered intravenously at a monthly equivalent dose of about 50 mg. In certain embodiments, tocilizumab is administered intravenously at a monthly equivalent dose of about 100 mg. In certain embodiments, tocilizumab is administered intravenously at a monthly equivalent dose of about 150 mg. In certain embodiments, tocilizumab is administered intravenously at a monthly equivalent dose of about 250 mg. In certain embodiments, tocilizumab is administered intravenously at a monthly equivalent dose of about 350 mg. In certain embodiments, tocilizumab is administered intravenously at a monthly equivalent dose of about 500 mg.

In various embodiments, tocilizumab is administered subcutaneously at a monthly equivalent dose of 50-1000 mg, such 50-80 mg, 50-160 mg, 50-240 mg, 50-400 mg, 50-560 mg, 50-800 mg, 80-160 mg, 80-240 mg, 80-400 mg, 80-560 mg, 80-800 mg, 80-1000 mg, 160-240 mg, 160-400 mg, 160-560 mg, 160-800 mg, 160-1000 mg, 240-400 mg, 240-560 mg, 240-800 mg, 240-1000 mg, 400-560 mg, 400-800 mg, 400-1000 mg, 560-800 mg, 560-1000 mg, or 800-100 mg. In certain preferred embodiments, tocilizumab is administered subcutaneously at a monthly equivalent dose of 80-800 mg. In various embodiments, tocilizumab is administered subcutaneously at a monthly equivalent dose of about 50 mg, 80 mg, 160 mg, 240 mg, 400 mg, 560 mg, 800 mg, or 1000 mg. In certain embodiments, tocilizumab is administered subcutaneously at a monthly equivalent dose of about 50 mg. In certain embodiments, tocilizumab is administered subcutaneously at a monthly equivalent dose of about 80 mg. In certain embodiments, tocilizumab is administered subcutaneously at a monthly equivalent dose of about 160 mg. In certain embodiments, tocilizumab is administered subcutaneously at a monthly equivalent dose of about 240 mg. In certain embodiments, tocilizumab is administered subcutaneously at a monthly equivalent dose of about 400 mg. In certain embodiments, tocilizumab is administered subcutaneously at a monthly equivalent dose of about 560 mg. In certain embodiments, tocilizumab is administered subcutaneously at a monthly equivalent dose of about 800 mg. In certain embodiments, tocilizumab is administered subcutaneously at a monthly equivalent dose of about 1000 mg.

In some embodiments, the IL-6 antagonist is sarilumab. In various embodiments, sarilumab is administered intravenously at a monthly equivalent dose of 10-150 mg, such as 10-12 mg, 10-24 mg, 10-48 mg, 10-60 mg, 10-72 mg, 10-120 mg, 12-24 mg, 12-48 mg, 12-60 mg, 12-72 mg, 12-120 mg, 12-150 mg, 24-48 mg, 24-60 mg, 24-72 mg, 24-120 mg, 24-150 mg, 48-60 mg, 48-72 mg, 48-120 mg, 48-150 mg, 60-72 mg, 60-120 mg, 60-150 mg, 72-120 mg, 72-150 mg, or 120-150 mg. In certain preferred embodiments, sarilumab is administered intravenously at a monthly equivalent dose of 12-120 mg. In various embodiments, sarilumab is administered intravenously at a monthly equivalent dose of 10 mg, 12 mg, 24 mg, 48 mg, 60 mg, 72 mg, 120 mg, or 150 mg. In certain embodiments, sarilumab is administered intravenously at a monthly equivalent dose of 10 mg. In certain embodiments, sarilumab is administered intravenously at a monthly equivalent dose of 12 mg. In certain embodiments, sarilumab is administered intravenously at a monthly equivalent dose of 24 mg. In certain embodiments, sarilumab is administered intravenously at a monthly equivalent dose of 48 mg. In certain embodiments, sarilumab is administered intravenously at a monthly equivalent dose of 60 mg. In certain embodiments, sarilumab is administered intravenously at a monthly equivalent dose of 72 mg. In certain embodiments, sarilumab is administered intravenously at a monthly equivalent dose of 120 mg. In certain embodiments, sarilumab is administered intravenously at a monthly equivalent dose of 150 mg.

In various embodiments, sarilumab is administered subcutaneously at a monthly equivalent dose of 10-200 mg, such as 10-20 mg, 10-40 mg, 10-60 mg, 10-80 mg, 10-100 mg, 10-120 mg, 20-40 mg, 20-60 mg, 20-80 mg, 20-100 mg, 20-120 mg, 20-200 mg, 40-60 mg, 40-80 mg, 40-100 mg, 40-120 mg, 40-200 mg, 60-80 mg, 60-100 mg, 60-120 mg, mg, 60-200 mg, 80-100 mg, 80-120 mg, 80-200 mg, 100-120 mg, 100-200 mg, or 120-200 mg. In certain preferred embodiments, sarilumab is administered subcutaneously at a monthly equivalent dose of 20-200 mg. In various embodiments, sarilumab is administered subcutaneously at a monthly equivalent dose of about 10 mg, 20 mg, 30 mg, 40 mg, 50 mg, 60 mg, 80 mg, 100 mg, 120 mg, 150 mg, or 200 mg. In certain embodiments, sarilumab is administered subcutaneously at a monthly equivalent dose of about 20 mg. In certain embodiments, sarilumab is administered subcutaneously at a monthly equivalent dose of about 40 mg. In certain embodiments, sarilumab is administered subcutaneously at a monthly equivalent dose of about 80 mg. In certain embodiments, sarilumab is administered subcutaneously at a monthly equivalent dose of about 100 mg. In certain embodiments, sarilumab is administered subcutaneously at a monthly equivalent dose of about 120 mg. In certain embodiments, sarilumab is administered subcutaneously at a monthly equivalent dose of about 200 mg.

In some embodiments, the IL-6 antagonist is vobarilizumab. In various embodiments, vobarilizumab is administered intravenously at a monthly equivalent dose of 2-150 mg, such as 2-4 mg, 2-6 mg, 2-30 mg, 2-60 mg, 2-84 mg, 2-120 mg, 4-6 mg, 4-30 mg, 4-60 mg, 4-84 mg, 4-120 mg, 4-150 mg, 6-30 mg, 6-60 mg, 6-84 mg, 6-120 mg, 6-150 mg, 30-60 mg, 30-84 mg, 30-120 mg, 30-150 mg, 60-84 mg, 60-120 mg, 60-150 mg, 84-120 mg, 84-150 mg, or 120-150 mg. In certain preferred embodiments, vobarilizumab is administered intravenously at a monthly equivalent dose of 4-120 mg. In various embodiments, vobarilizumab is administered intravenously at a monthly equivalent dose of about 2 mg, 4 mg, 6 mg, 30 mg, 60 mg, 84 mg, 120 mg, or 150 mg. In certain embodiments, vobarilizumab is administered intravenously at a monthly equivalent dose of about 2 mg. In certain embodiments, vobarilizumab is administered intravenously at a monthly equivalent dose of about 4 mg. In certain embodiments, vobarilizumab is administered intravenously at a monthly equivalent dose of about 6 mg. In certain embodiments, vobarilizumab is administered intravenously at a monthly equivalent dose of about 30 mg. In certain embodiments, vobarilizumab is administered intravenously at a monthly equivalent dose of about 60 mg. In certain embodiments, vobarilizumab is administered intravenously at a monthly equivalent dose of about 84 mg. In certain embodiments, vobarilizumab is administered intravenously at a monthly equivalent dose of about 120 mg. In certain embodiments, vobarilizumab is administered intravenously at a monthly equivalent dose of about 150 mg.

In various embodiments, vobarilizumab is administered subcutaneously at a monthly equivalent dose of 5-200 mg, such as 5-7 mg, 5-10 mg, 5-20 mg, 5-50 mg, 5-70 mg, 5-100 mg, 5-140 mg, 7-10 mg, 7-20 mg, 7-50 mg, 7-70 mg, 7-100 mg, 7-140 mg, 7-200 mg, 10-20 mg, 10-50 mg, 10-70 mg, 10-100 mg, 10-140 mg, 10-200 mg, 20-50 mg, 20-70 mg, 20-100 mg, 20-140 mg, 20-200 mg, 50-70 mg, 50-100 mg, 50-140 mg, 50-200 mg, 70-100 mg, 70-140 mg, 70-200 mg, 100-140 mg, 100-200 mg, or 140-200 mg. In certain preferred embodiments, vobarilizumab is administered subcutaneously at a monthly equivalent dose of 7-200 mg. In various embodiments, vobarilizumab is administered subcutaneously at a monthly equivalent dose of about 5 mg, 7 mg, 10 mg, 20 mg, 40 mg, 50 mg, 70 mg, 100 mg, 140 mg, or 200 mg. In certain embodiments, vobarilizumab is administered subcutaneously at a monthly equivalent dose of about 7 mg. In certain embodiments, vobarilizumab is administered subcutaneously at a monthly equivalent dose of about 10 mg. In certain embodiments, vobarilizumab is administered subcutaneously at a monthly equivalent dose of about 50 mg. In certain embodiments, vobarilizumab is administered subcutaneously at a monthly equivalent dose of about 100 mg. In certain embodiments, vobarilizumab is administered subcutaneously at a monthly equivalent dose of about 140 mg. In certain embodiments, vobarilizumab is administered subcutaneously at a monthly equivalent dose of about 200 mg.

3. Examples

The following examples are provided by way of exemplification and illustration, not limitation.

3.1. Example 1: Phase 1/2 Clinical Study

A Phase 1/2 clinical study was conducted to assess the safety, pharmacokinetics, and pharmacodynamics of multiple IV doses of COR-001.

3.1.1. Drug Product (COR-001

COR-001 is a human IgG1, kappa antibody directed against interleukin-6 (IL-6). COR-001 contains a "YTE" mutation in its Fc region. The sequence and other features of COR-001 are described in Chapter 2.7.1.1 above.

3.1.2. Study Design

The study was a randomized, double-blind, placebo-controlled trial designed to evaluate the safety, pharmacokinetics, and pharmacodynamic effects of multiple doses of COR-001 (MEDI5117) or placebo administered to sequential cohorts of hemodialysis patients.

Key inclusion criteria include stage 5 chronic kidney disease (CKD-5) on hemodialysis, positive for TMPRSS6 736A genotype (major allele), IL-6 level greater than 4 pg/mL, and erythropoietic resistive index greater than 8.

Ten hemodialysis patients were randomized to COR-001 or placebo within each dosing cohort. When a higher dose than studied in a prior cohort was initiated, the first 2 (sentinel) patients in that cohort (randomized 1:1 to COR-001 or placebo) were randomized first and the remaining patients were randomized at least 48 hours later, in a 7:1 ratio of COR-001 to placebo. The final ratio of patients treated with COR-001 vs. placebo were 8:2 in each cohort of 10 patients. The maximum tolerated dose (MTD) assessment was based on safety data from Weeks 1 to 3. If more than 2 of 8 active patients in a cohort experienced a dose-limiting toxicity (DLT), the MTD was considered to have been exceeded.

The Dose Escalation Schematic is shown in FIG. 1. COR-001 was administered as an intravenous infusion, started any time before the last 1 hour of the dialysis treatment. The COR-001 dose regimens are shown in Table 1 below.

TABLE 1

| Dose Cohort | Dose Regimen | Number of Doses | Total Cumulative Dose |
| --- | --- | --- | --- |
| 1 | 2 mg every 14 days | 6 | 12 mg |
| 2 | 6 mg every 14 days | 6 | 36 mg |
| 3 | 6 mg every 14 days | 6 | 36 mg |
| 4 | 2 mg every 14 days | 6 | 12 mg |
| 5 | 20 mg every 14 days | 6 | 120 mg |
| 6 | 20 mg every 14 days | 6 | 120 mg |

Figure 2:
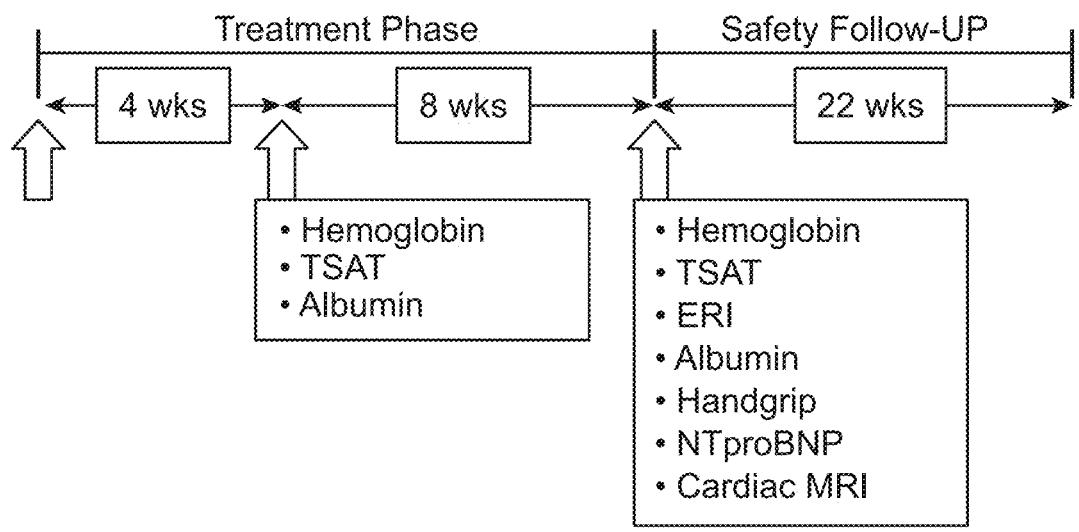
FIG. 2 shows the timeline and the efficacy analysis of the treatment phase and the safety follow-up phase.

The total study duration for an individual patient was approximately 9 months, excluding the screening period of up to 4 weeks. As shown in FIG. 2, the study included a treatment period of 12 weeks (Week 1 through Week 12), a safety follow-up period of 12 weeks (Week 13 through Week 24), and an extended follow-up period of 10 weeks (Week 25 through Week 35).

Interim study-collected data were summarized by treatment group for the appropriate analysis population, using descriptive statistics. Descriptive statistics for continuous variables included number of patients (n), mean, standard deviation (SD), median, quartiles (Q1 and Q3), minimum (min) and maximum (max) values. Analysis of categorical variables included frequency and percentages.

The changes in high-sensitivity C-reactive protein (hsCRP), absolute neutrophil count (ANC), lipoprotein(a) level, LDL level, hemoglobin, transferrin saturation (TSAT), albumin, erythropoietic resistive index (ERI), handgrip, NT-proBNP, and cardiac MRI were recorded during the study.

3.1.3. Analysis of Clinical Data

Analyses were performed to determine the effect of COR-001 on C-reactive protein (CRP), the effect of COR-001 on hemoglobin level, the effect of COR-001 on various cardiac parameters, and the effect of COR-001 on levels of neutrophils and platelets.

C-reactive protein (CRP) is a marker of inflammation. CRP levels increase in response to inflammation, and can be measured with an hsCRP (high-sensitivity C-reactive protein) test. The hsCRP level was measured over the course of the treatment period and the safety follow-up period in patients of the placebo-treated, 2 mg dose regimen, 6 mg dose regimen, and 20 mg dose regimen groups, respectively.

Figure 3A:
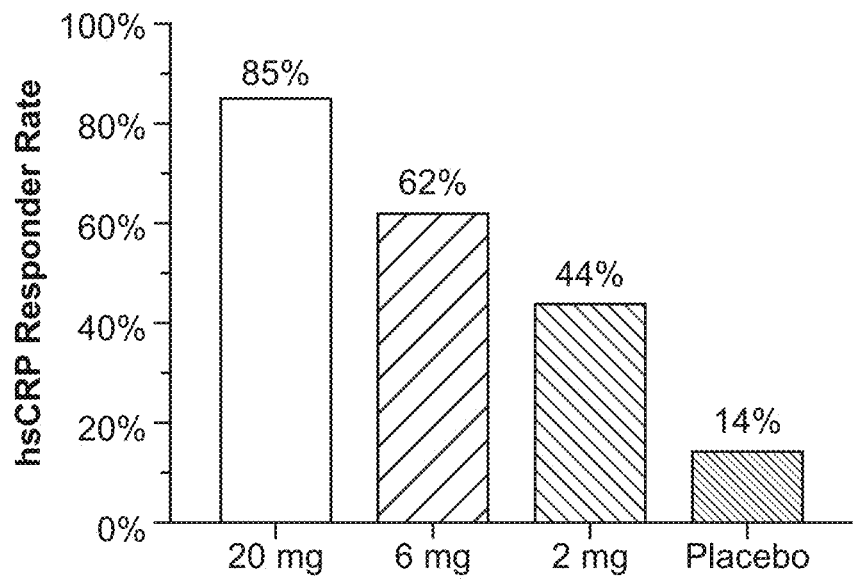
FIGS. 3A and 3B show the results of C-reactive protein (CRP) responder analysis after treatment with COR-001 (anti-IL-6) or canakinumab (anti-IL1β).
Figure 3B:
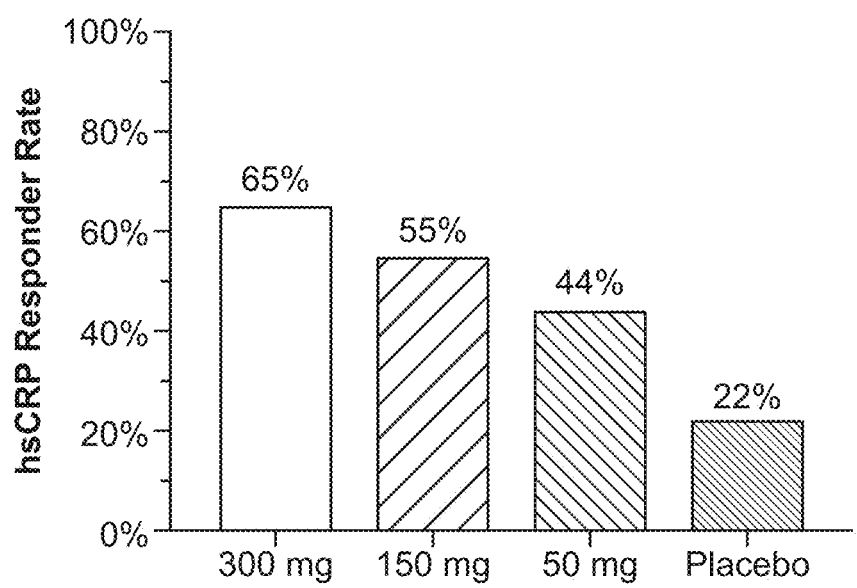

The percentages of patients with post-treatment average hsCRP <2 mg/L at Week 12 were 44%, 62%, and 85% in the 2 mg dose regimen, 6 mg dose regimen, and 20 mg dose regimen groups, respectively, as compared to 14% in the placebo group. The hsCRP responder analysis shows that COR-001 (anti-IL-6) has a superior effect on hsCRP than has been reported for canakinumab (anti-IL1 (3)) in the CANTOS trial. The hsCRP responder rates of COR-001 in stage 5 chronic kidney disease patients on dialysis at IV doses of 20 mg and 6 mg (FIG. 3A) were higher than the hsCRP responder rates of canakinumab at equivalent doses in the CANTOS trial (FIG. 3B). The in vivo IC50 concentration of COR-001 for CRP (50% reduction of baseline CRP) is 206 ng/mL.

Figure 4:
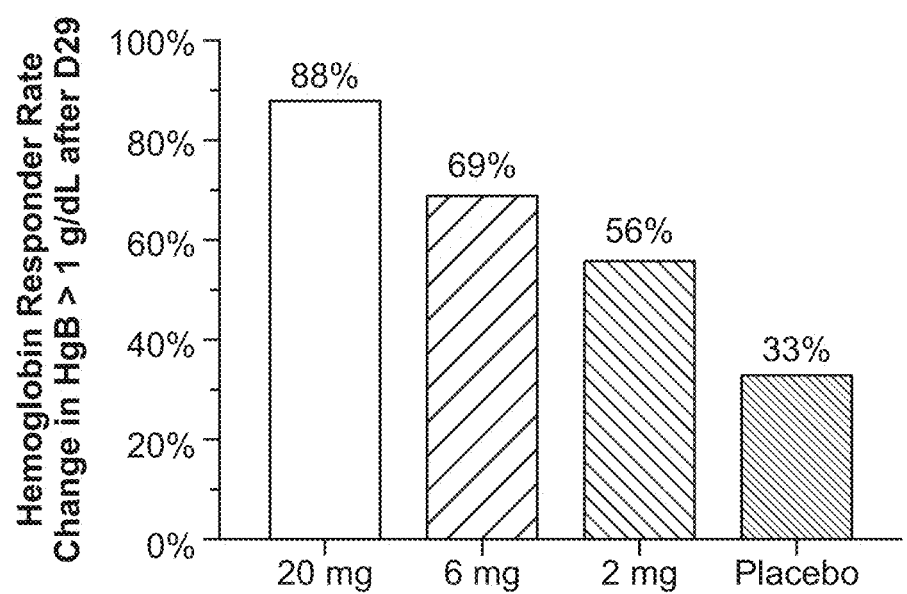
FIG. 4 shows the results of hemoglobin responder analysis after treatment with COR-001 at doses of 2 mg, 6 mg, and 20 mg. Hemoglobin responder was defined as increase by 1 g/dL or more after Day 29. Investigators were not permitted to change ESA dosing until after Day 29.

COR-001 improved a primary indicator of anemia, hemoglobin levels. The hemoglobin responder analysis indicated a dose-dependent hemoglobin responder rate of COR-001 treatment (FIG. 4).

Figure 5:
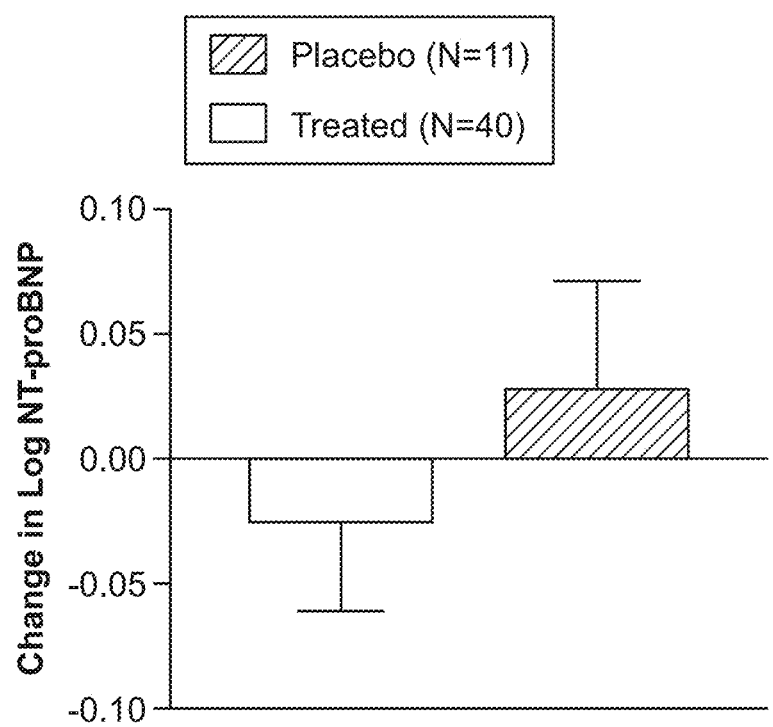
FIG. 5 shows the effect of COR-001 on the diastolic cardiac parameter, NT-proBNP.

The effect of COR-001 on various biomarkers of heart failure was determined. As shown in FIG. 5, COR-001 decreased the level of the N-terminal prohormone of brain natriuretic peptide (NT-proBNP). The result indicates that treatment of COR-001 can reduce heart failure.

Anti-inflammatory therapies in general, and IL-6 inhibitory therapies in particular, create a risk of inducing immune suppression, thereby promoting the emergence of infections, sometimes serious in nature. Immune suppression can be measured by neutrophil counts. The effect of COR-001 on neutrophil counts was determined.

Figure 6A:
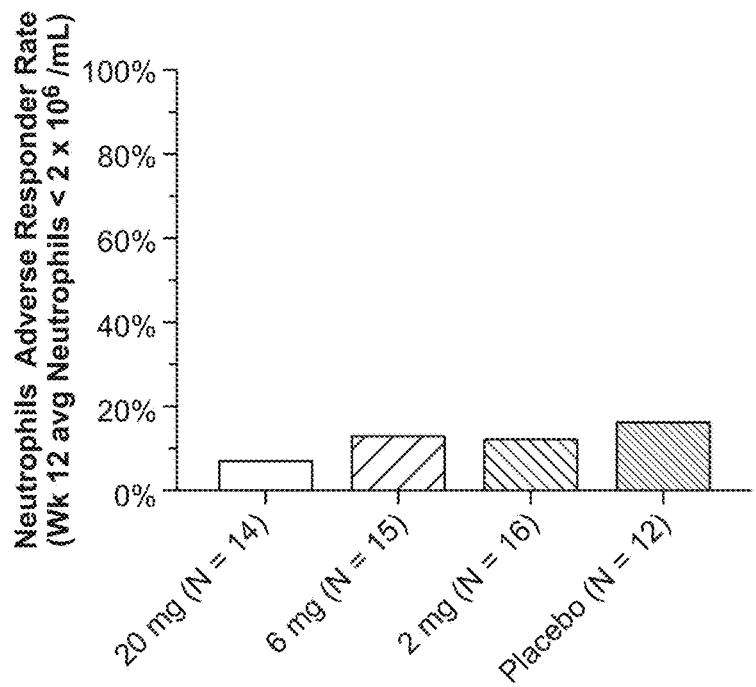
FIGS. 6A and 6B show the adverse responder rate for neutrophils and platelets.

Surprisingly, despite significant reduction in inflammation, as measured by hsCRP levels (FIG. 3A), the absolute neutrophil count of patients treated with COR-001 did not decline to below normal levels. No opportunistic infections were observed during the treatment. As shown in FIG. 6A, the percentages of patients with absolute neutrophil count below $2.0 \times 10^9$/L were not increased with COR-001 at all tested doses as compared to the placebo group. All patients treated with COR-001 at all tested doses had an absolute neutrophil count above $1.5 \times 10^9$/L. The in vivo IC50 concentration of COR-001 for neutrophil count (50% reduction of baseline neutrophil count) is 5540 ng/mL.

Figure 6B:
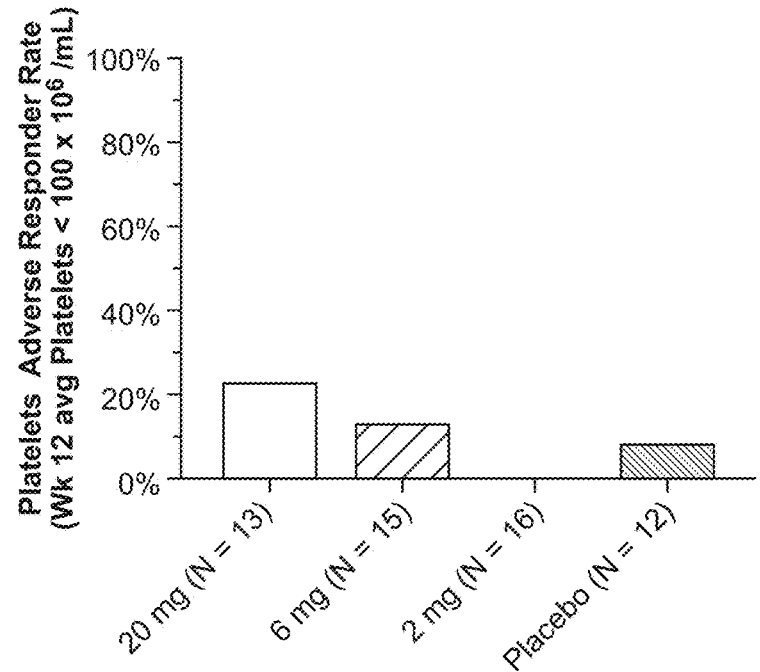

The percentages of patients with platelet count below $100 \times 10^9$/L were less than 30% with COR-001 for all tested doses (FIG. 6B). The in vivo IC50 concentration of COR-001 for platelet count (50% reduction of baseline platelet count) is 13800 ng/mL.

In summary, the clinical data indicate that COR-001 treatment at doses of 2 mg, 6 mg, and 20 mg can reduce inflammation without inducing immune suppression in patients with stage 5 chronic kidney disease (CKD-5) on dialysis, whereas the absolute neutrophil count was not decreased significantly in patients treated with COR-001.

Administration of COR-001 reduced CRP in a dose-dependent matter. In addition, COR-001 increased hemoglobin level in these patients. COR-001 decreased the biomarkers of heart failure NT-proBNP.

4. Incorporation by Reference

All publications, patents, patent applications and other documents cited in this application are hereby incorporated by reference in their entireties for all purposes to the same extent as if each individual publication, patent, patent application or other document were individually indicated to be incorporated by reference for all purposes.

5. Equivalents

While various specific embodiments have been illustrated and described, the above specification is not restrictive. It will be appreciated that various changes can be made without departing from the spirit and scope of the invention(s). Many variations will become apparent to those skilled in the art upon review of this specification.

What is claimed is:

1. A method of treating a patient who has KDOQI stage 3-5 chronic kidney disease (CKD) with inflammation to reduce the risk of cardiovascular morbidity and mortality, comprising: administering a dose of 5-30 mg COR-001 subcutaneously once every 28 days to a patient with KDOQI stage 3-5 CKD and a CRP level greater than 2 mg/L, wherein the dose is sufficient to reduce the CRP level to 2 mg/L or less and does not cause a decrease in absolute neutrophil count (ANC) below 1,500 cells/μL.

2. The method of claim 1, wherein the method comprises administering 5-10 mg COR-001 subcutaneously once every 28 days to the patient.

3. The method of claim 1, wherein the method comprises administering 10-20 mg COR-001 subcutaneously once every 28 days to the patient.

4. The method of claim 1, wherein the method comprises administering 20-30 mg COR-001 subcutaneously once every 28 days to the patient.

5. The method of claim 1, wherein the method comprises administering 15 mg COR-001 subcutaneously once every 28 days to the patient.

6. The method of claim 1, wherein the method comprises administering 30 mg COR-001 subcutaneously once every 28 days to the patient.

7. The method of claim 1, wherein post-treatment low-density lipoprotein (LDL) level is increased by no more than 10% as compared to pre-treatment levels.

8. The method of claim 1, wherein the administration reduces the risk of heart failure and/or cardiovascular death.

9. The method of claim 1, wherein the administration increases cardiac function.

10. The method of claim 1, wherein the administration reduces fibrosis after acute myocardial infarction.

11. The method according to claim 1, wherein the cardiovascular morbidity and mortality is selected from a group consisting of (i) nonfatal myocardial infarction, (ii) nonfatal stroke, and (iii) cardiovascular death.

12. The method according to claim 1, wherein the cardiovascular morbidity and mortality is heart failure.

* * * * *

```
                           SEQUENCE LISTING

<160> NUMBER OF SEQ ID NOS: 14

<210> SEQ ID NO 1
<211> LENGTH: 277
<212> TYPE: PRT
<213> ORGANISM: Homo sapiens

<400> SEQUENCE: 1

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 2
<211> LENGTH: 1201
<212> TYPE: DNA
<213> ORGANISM: Homo sapiens

<400> SEQUENCE: 2
aatattagag tctcaacccc caataaatat aggactggag atgtctgagg ctcattctgc      60
```

```
cctcgagccc accgggaacg aaagagaagc tctatctccc ctccaggagc ccagctatga      120
actccttctc cacaagcgcc ttcggtccag ttgccttctc cctggggctg ctcctggtgt      180
tgcctgctgc cttccctgcc ccagtacccc caggagaaga ttccaaagat gtagccgccc      240
cacacagaca gccactcacc tcttcagaac gaattgacaa acaaattcgg tacatcctcg      300
acggcatctc agccctgaga aggagacat gtaacaagag taacatgtgt gaaagcagca       360
aagaggcact ggcagaaaac aacctgaacc ttccaaagat ggctgaaaaa gatggatgct      420
tccaatctgg attcaatgag gagacttgcc tggtgaaaat catcactggt cttttggagt      480
ttgaggtata cctagagtac ctccagaaca gatttgagag tagtgaggaa caagccagag      540
ctgtgcagat gagtacaaaa gtcctgatcc agttcctgca gaaaaaggca agaatctag       600 atgcaataac caccctgac ccaaccacaa atgccagcct gctgacgaag ctgcaggcac       660
agaaccagtg gctgcaggac atgacaactc atctcattct gcgcagcttt aaggagttcc      720
tgcagtccag cctgagggct cttcggcaaa tgtagcatgg gcacctcaga ttgttgttgt      780
taatgggcat tccttcttct ggtcagaaac ctgtccactg gcacagaac ttatgttgtt       840 ctctatggag aactaaaagt atgagcgtta ggacactatt ttaattattt ttaattttatt     900 aatatttaaa tatgtgaagc tgagttaatt tatgtaagtc atatttatat ttttaagaag     960
taccacttga acattttat gtattagttt tgaaataata atggaaagtg gctatgcagt      1020
ttgaatatcc tttgtttcag agccagatca tttcttggaa agtgtaggct tacctcaaat    1080
aaatggctaa cttatacata ttttttaaaga aatatttata ttgtatttat ataatgtata    1140
aatggttttt ataccaataa atggcatttt aaaaaattca gcaaaaaaa aaaaaaaaaa      1200 a                                                                    1201
```

<210> SEQ ID NO 3
<211> LENGTH: 468
<212> TYPE: PRT
<213> ORGANISM: Homo sapiens

<400> SEQUENCE: 3

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160
```

-continued

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Ala Asn Ile Thr Val
            210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
            290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
            355                 360                 365

Val Ala Gly Gly Ser Leu Ala Phe Gly Thr Leu Leu Cys Ile Ala Ile
            370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
            450                 455                 460

Phe Phe Pro Arg
465

<210> SEQ ID NO 4
<211> LENGTH: 918
<212> TYPE: PRT
<213> ORGANISM: Homo sapiens

<400> SEQUENCE: 4

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
50                  55                  60

```
Ile Val Trp Lys Thr Asn His Phe Thr Ile Pro Lys Glu Gln Tyr Thr
 65                  70                  75                  80

Ile Ile Asn Arg Thr Ala Ser Ser Val Thr Phe Thr Asp Ile Ala Ser
                 85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
        450                 455                 460

Pro Cys Ile Thr Asp Trp Gln Gln Glu Asp Gly Thr Val His Arg Thr
465                 470                 475                 480
```

-continued

Tyr Leu Arg Gly Asn Leu Ala Glu Ser Lys Cys Tyr Leu Ile Thr Val
            485                 490                 495

Thr Pro Val Tyr Ala Asp Gly Pro Gly Ser Pro Glu Ser Ile Lys Ala
        500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
            565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
            645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685

Thr Asp Val Ser Val Val Glu Ile Glu Ala Asn Asp Lys Lys Pro Phe
        690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
            725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
        755                 760                 765

His Gln Val Pro Ser Val Gln Val Phe Ser Arg Ser Glu Ser Thr Gln
        770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
            805                 810                 815

Gln Asn Cys Ser Gln His Glu Ser Ser Pro Asp Ile Ser His Phe Glu
        820                 825                 830

Arg Ser Lys Gln Val Ser Ser Val Asn Glu Glu Asp Phe Val Arg Leu
        835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
            885                 890                 895

Thr Asp Glu Gly Met Pro Lys Ser Tyr Leu Pro Gln Thr Val Arg Gln

Gly Gly Tyr Met Pro Gln
        915

<210> SEQ ID NO 5
<211> LENGTH: 224
<212> TYPE: PRT
<213> ORGANISM: Homo sapiens

<400> SEQUENCE: 5

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220

<210> SEQ ID NO 6
<211> LENGTH: 84
<212> TYPE: PRT
<213> ORGANISM: Homo sapiens

<400> SEQUENCE: 6

Met Ala Leu Ser Ser Gln Ile Trp Ala Ala Cys Leu Leu Leu Leu Leu
1               5                   10                  15

Leu Leu Ala Ser Leu Thr Ser Gly Ser Val Phe Pro Gln Gln Thr Gly
            20                  25                  30

Gln Leu Ala Glu Leu Gln Pro Gln Asp Arg Ala Gly Ala Arg Ala Ser
        35                  40                  45

Trp Met Pro Met Phe Gln Arg Arg Arg Arg Arg Asp Thr His Phe Pro
    50                  55                  60

Ile Cys Ile Phe Cys Cys Gly Cys Cys His Arg Ser Lys Cys Gly Met
65                  70                  75                  80

Cys Cys Lys Thr

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Asn Tyr Met Ile
1               5

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Leu Tyr Tyr Tyr Ala Gly Asp Thr Tyr Tyr Ala Asp Ser Val Lys
1               5                   10                  15

Gly

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Ala Asp Asp His Pro Pro Trp Ile Asp Leu
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Gly Ile Ser Ser Trp Leu Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Ala Ser Thr Leu Glu Ser
1               5

<210> SEQ ID NO 12
<211> LENGTH: 8
<212> TYPE: PRT
<213> ORGANISM: Artificial Sequence
<220> FEATURE:

-continued

<223> OTHER INFORMATION: Description of Artificial Sequence: Synthetic
      peptide

<400> SEQUENCE: 12

Gln Gln Ser Trp Leu Gly Gly Ser
1               5

<210> SEQ ID NO 13
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Ile Ser Ser Asn
                20                  25                  30

Tyr Met Ile Trp Val Arg Gln Ala Pro Gly Lys Gly Leu Glu Trp Val
            35                  40                  45

Ser Asp Leu Tyr Tyr Ala Gly Asp Thr Tyr Tyr Ala Asp Ser Val
50                  55                  60

Lys Gly Arg Phe Thr Met Ser Arg Asp Ile Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Trp Ala Asp Asp His Pro Pro Trp Ile Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Tyr Ile
                245                 250                 255

Thr Arg Glu Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 14
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Trp Leu Gly Gly Ser
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

```
Asn Arg Gly Glu Cys
    210
```